(12) United States Patent
Ott et al.

(10) Patent No.: US 10,624,992 B2
(45) Date of Patent: Apr. 21, 2020

(54) HUMAN AIRWAY STEM CELLS IN LUNG EPITHELIAL ENGINEERING

(71) Applicant: The General Hospital Corporation, Boston, MA (US)

(72) Inventors: Harald C. Ott, Wenham, MA (US); Sarah E. Gilpin, Somerville, MA (US)

(73) Assignee: The General Hospital Corporation, Boston, MA (US)

( * ) Notice: Subject to any disclaimer, the term of this patent is extended or adjusted under 35 U.S.C. 154(b) by 109 days.

(21) Appl. No.: 15/595,464

(22) Filed: May 15, 2017

(65) Prior Publication Data

US 2017/0326273 A1    Nov. 16, 2017

Related U.S. Application Data

(63) Continuation of application No. PCT/US2017/031076, filed on May 4, 2017.
(Continued)

(51) Int. Cl.
     *A61F 2/04*      (2013.01)
     *A61L 27/38*      (2006.01)
     (Continued)

(52) U.S. Cl.
     CPC ............ *A61L 27/3882* (2013.01); *A61F 2/04* (2013.01); *A61L 27/3604* (2013.01);
     (Continued)

(58) Field of Classification Search
     CPC .. A61L 27/3882; A61L 27/36; A61L 27/3604; A61L 27/3886; A61L 27/3683; A61L 27/3808; A61L 27/3834; A61L 27/3895; A61L 27/3891; A61L 2430/22; A61F 2/04; C12N 5/0697; C12N 2501/50; C12N 2502/28; C12N 2502/27; C12N 2533/90; C12N 2501/734; C12N 2501/998

See application file for complete search history.

(56) References Cited

U.S. PATENT DOCUMENTS

| | | |
|---|---|---|
| 4,446,229 A | 5/1984 | Indech |
| 4,598,706 A | 7/1986 | Darowski |
| | (Continued) | |

FOREIGN PATENT DOCUMENTS

| | | |
|---|---|---|
| CA | 2751133 | 2/2009 |
| CN | 1911438 | 2/2007 |
| | (Continued) | |

OTHER PUBLICATIONS

Tomoshi et al, "Ventilation-Based Decellularization System of the Lung" Bioresearch Open Access, (2016) 5(1); 118-126. Published May 1, 2016 (Year: 2016).*

(Continued)

*Primary Examiner* — Brian A Dukert
*Assistant Examiner* — Rebecca Lynee Zimmerman
(74) *Attorney, Agent, or Firm* — Fish & Richardson P.C.

(57) ABSTRACT

Methods of using human airway stem cells in lung epithelial engineering, optionally wherein the cells are contacted with a gamma secretase inhibitor, bioartificial airway organs produced thereby, and the use thereof, e.g., for transplantation. Also methods of treating a bio-artificial matrix with Tenascin-C and/or fibrillin 2.

16 Claims, 50 Drawing Sheets
Specification includes a Sequence Listing.

Related U.S. Application Data

(60) Provisional application No. 62/483,760, filed on Apr. 10, 2017, provisional application No. 62/426,146, filed on Nov. 23, 2016, provisional application No. 62/337,041, filed on May 16, 2016.

(51) Int. Cl.
*C12N 5/071* (2010.01)
*A61L 27/36* (2006.01)

(52) U.S. Cl.
CPC ....... *A61L 27/3683* (2013.01); *A61L 27/3808* (2013.01); *A61L 27/3834* (2013.01); *A61L 27/3886* (2013.01); *A61L 27/3891* (2013.01); *A61L 27/3895* (2013.01); *C12N 5/0688* (2013.01); *C12N 5/0697* (2013.01); *A61L 2430/22* (2013.01); *C12N 2501/165* (2013.01); *C12N 2501/42* (2013.01); *C12N 2501/50* (2013.01); *C12N 2501/734* (2013.01); *C12N 2501/998* (2013.01); *C12N 2501/999* (2013.01); *C12N 2502/27* (2013.01); *C12N 2502/28* (2013.01); *C12N 2513/00* (2013.01); *C12N 2533/54* (2013.01); *C12N 2533/90* (2013.01)

(56) References Cited

U.S. PATENT DOCUMENTS

| | | | |
|---|---|---|---|
| 5,540,225 | A | 7/1996 | Schutt |
| 5,750,329 | A | 5/1998 | Quinn et al. |
| 6,087,552 | A | 7/2000 | Gregory |
| 6,121,042 | A * | 9/2000 | Peterson ............... C12M 41/00 435/284.1 |
| 6,416,995 | B1 | 7/2002 | Wolfinbarger |
| 6,479,064 | B1 | 11/2002 | Atala |
| 7,662,409 | B2 | 2/2010 | Masters |
| 9,005,885 | B2 | 4/2015 | Ott |
| 2002/0172705 | A1 | 11/2002 | Murphy et al. |
| 2002/0182241 | A1 | 12/2002 | Borenstein et al. |
| 2002/0182261 | A1 | 12/2002 | Dai et al. |
| 2003/0087428 | A1 | 5/2003 | Wolfinbarger et al. |
| 2003/0129751 | A1 | 7/2003 | Grikscheit et al. |
| 2003/0166274 | A1 | 9/2003 | Hewitt et al. |
| 2003/0180268 | A1 | 9/2003 | Atala |
| 2005/0107868 | A1 | 5/2005 | Yasuhide et al. |
| 2005/0196423 | A1 | 9/2005 | Batich et al. |
| 2005/0256588 | A1 | 11/2005 | Sawa et al. |
| 2007/0059293 | A1 | 3/2007 | Atala |
| 2007/0244568 | A1 | 10/2007 | Matsuda et al. |
| 2008/0017194 | A1 | 1/2008 | Hassanein et al. |
| 2008/0131473 | A1 | 6/2008 | Brown et al. |
| 2008/0292595 | A1 | 11/2008 | Arbetman et al. |
| 2008/0292677 | A1 | 11/2008 | Cortiella et al. |
| 2009/0035855 | A1 | 2/2009 | Ying et al. |
| 2009/0060961 | A1 | 3/2009 | Naruse et al. |
| 2009/0075282 | A1 | 3/2009 | Mahmood et al. |
| 2009/0142836 | A1 | 6/2009 | Wang et al. |
| 2009/0202977 | A1 | 8/2009 | Ott et al. |
| 2010/0034791 | A1 | 2/2010 | Lelkes et al. |
| 2010/0092433 | A1 | 4/2010 | Levenberg et al. |
| 2012/0064537 | A1 * | 3/2012 | Ross .................. C12N 5/0068 435/6.13 |
| 2012/0141439 | A1 | 6/2012 | Ott |
| 2012/0302499 | A1 * | 11/2012 | Matheny ............. A61L 27/3633 514/8.9 |
| 2013/0084266 | A1 | 4/2013 | Ott et al. |
| 2014/0273220 | A1 | 9/2014 | Gerecht |
| 2015/0182560 | A1 | 7/2015 | Calle et al. |
| 2015/0289501 | A1 | 10/2015 | Raredon et al. |

FOREIGN PATENT DOCUMENTS

| | | |
|---|---|---|
| EP | 1555031 | 7/2005 |
| EP | 2484754 | 8/2012 |
| WO | WO 2002/053193 | 7/2002 |
| WO | WO 2007/025233 | 3/2007 |
| WO | WO 2007/095192 | 8/2007 |
| WO | WO 2010/091188 | 8/2010 |
| WO | WO 2010/141803 | 12/2010 |
| WO | WO 2011/059808 | 5/2011 |
| WO | WO 2013/071096 | 5/2013 |
| WO | WO-2013066802 A2 * | 5/2013 ............. A61K 35/28 |
| WO | WO 2014/110135 | 7/2014 |
| WO | WO 2014/168264 | 10/2014 |
| WO | WO 2014/200340 | 12/2014 |
| WO | WO 2015/108893 | 7/2015 |
| WO | WO 2015/119642 | 8/2015 |
| WO | WO 2015/138999 | 9/2015 |

OTHER PUBLICATIONS

Tsao et al "Y-Secretase Activation of Notch Signaling Regulates the Balance of Proximal and Distal Fates in Progenitor Cells of the Developing Lung" The Journal of Biological Chemistry. (2008) vol. 283, No. 43, pp. 29532-29544 (Year: 2008).*

Albelda et al., "Effects of increased ventilation on lung lymph flow in unanesthetized sheep," J Appl Physiol, Jun. 1986, 60(6):2063-70.

Andrade et al., "Cell-based tissue engineering for lung regeneration," Am J Physiol Lung Cell Mol Physiol, Feb. 2007, 292(2):L510-8.

Au et al., Bone marrow-derived mesenchymal stem cells facilitate engineering of long-lasting functional vasculature, Blood, May 2008, 111: 4551-4558.

Badylak et al., "Whole-organ tissue engineering: decellularization and recellularization of three-dimensional matrix scaffolds," Annual Review of Biomedical Engineering, 2011, 13: 27-53.

Balestrini and Niklason, "Extracellular matrix as a driver for lung regeneration," Annals of Biomedical Engineering, Mar. 2015, 43: 568-576.

Baptista et al., "Whole Organ Decellularization—A Tool for Bioscaffold Fabrication and Organ," Bioengineering, 31st Annual International Conference of the IEEE EMBS, Sep. 2-6, 2009.

Barkauskas et al., "Type 2 alveolar cells are stem cells in adult lung," The Journal of Clinical Investigation, Jul. 2013, 123: 3025-3036.

Bhattacharya et al., "Lung expansion and the perialveolar interstitial pressure gradient," J Appl Physiol, Jun. 1989, 66: 2600-5.

Boasquevisque et al., "Surgical Techniques: Lung Transplant and Lung vol. Reduction," Proceedings of the American Thoracic Society, Jan. 2009, 6:66-78.

Bonvillain et al., "Nonhuman primate lung decellularization and recellularization using a specialized large-organ bioreactor," J Vis Exp, Dec. 2013, (82):e50825.

Booth et al., "Acellular Normal and Fibrotic Human Lung Matrices as a Culture System for In Vitro Investigation," American Journal of Respiratory and Critical Care Medicine, 2012, 186(9):866-76.

Brew et al., "Mechanical Ventilation Injury and Repair in Extremely and Very Preterm Lungs," PLOS One, 2013, 8(5):e63905.

Bribriesco et al., "Experimental models of lung Transplantation," Front Biosci (Elite Ed), Jan. 2013, 5:266-72.

Brudno et al. "Enhancing microvascular formation and vessel maturation through temporal control over multiple pro-angiogenic and pro-maturation factors," Biomaterials, Dec. 2013, 34: 9201-9209.

Camargo et al., "Surgical maneuvers for the management of bronchial complications in lung transplantation," Eur J Cardiothorac Surg., 2008, 34:1206-1209.

Canadian Office Action in Application No. 2,762,590, dated Sep. 11, 2017.

Canadian Office Action in Canadian Application No. 2,762,590, dated Apr. 15, 2016, 13 pages.

Charest et al., "Design and validation of a clinical-scale bioreactor for long-term isolated lung culture," Biomaterials, Jun. 2015, 52: 79-87.

Chen et al., "Formation of lung alveolar-like structures in collagen-glycosaminoglycan scaffolds in vitro," Tissue Eng., Sep.-Oct. 2005, 11(9-10):1436-48.

(56) References Cited

OTHER PUBLICATIONS

Conconi et al., "Tracheal matrices, obtained by a detergent-enzymatic method, support in vitro the adhesion of chondrocytes and tracheal epithelial cells," Transplant International, 2005, 18:727-734.
Cotiella et al., "Tissue-Engineered Lung: An In Vivo and In Vitro Comparison of Polyglycolic Acid and Pluronic F-127 Hydrogel/Somatic Lung Progenitor Cell Constructs to Support Tissue Growth," Tissue Engineering, 2006, 12:1213-1225.
Crosby and Waters, "Epithelial repair mechanisms in the lung," American Journal of Physiology Lung Cellular and Molecular Physiology, 2010, 298: L715-731.
Daley et al., "Extracellular matrix dynamics in development and regenerative medicine," Journal of Cell Science, 2008, 121: 255-264.
Davidson et al., "Murine epithelial cells: isolation and culture," Journal of Cystic Fibrosis, Aug. 2004, 3 Suppl 2: 59-62.
Declaration of Harald C. Ott, M.D. Under 37 CFR 1.131. and Ott, Curriculum Vitae, Apr. 11, 2014, 17 pages.
Desai and Cardoso, "Growth factors in lung development and disease: friends or foe?," Respire. Res., 2002, 3:2.
Desai et al., "Alveolar progenitor and stem cells in lung development, renewal and cancer," Nature, Mar. 2014, 507: 190-194.
Ding et al., "Design of compliance chamber and after-load in apparatus for cultured endothelial cells subjected to stresses," Cell Biology International, 2006, 30:439-444.
Dupuit et al., "Differentiated and functional human airway epithelium regeneration in tracheal xenografts," American Journal of Physiology Lung Cellular and Molecular Physiology, 2000, 278: L165-176.
Erasmus et al., "Normothermic ex vivo lung perfusion of non-heart-beating donor lungs in pigs: from pretransplant function analysis towards a 6-h machine preservation," Transpl Int , Jul. 2006, 19: 589-593.
Evans et al., "Cellular and molecular characteristics of basal cells in airway epithelium," Experimental Lung Research, 2001, 27: 401-415.
Evans et al., "Renewal of alveolar epithelium in the rat following exposure to NO2," The American Journal of Pathology, 1973; 70: 175-198.
Evans et al., "Role of nonciliated cells in renewal of the bronchial epithelium of rats exposed to NO2," The American Journal of Pathology, 1986, 123: 126-133.
First Chinese Office Action in Chinese Application No. 201080032724.4, dated Dec. 4, 2012, 7 pages, (with English translation).
Fulcher and Randell, "Human nasal and tracheo-bronchial respiratory epithelial cell culture," Methods in Molecular Biology, 2013, 945: 109-121.
Gaissert and Patterson, "Surgical Techniques of Single and Bilateral Lung Transplantation," The Transplantation and Replacement of Thoracic Organs, 1996, 457-463.
Gilbert et al., "Decellularization of tissues and organs," Biomaterials, 2006, 27(9) :3675-83.
Gilpin and Ott, "Using Nature's Platform to Engineer Bio-Artificial Lungs," Annals of the American Thoracic Society, 2015, 12 Suppl 1: S45-49.
Gilpin et al., "Enhanced lung epithelial specification of human induced pluripotent stem cells on decellularized lung matrix," Ann Thorac Surg, Nov. 2014, 98(5):1721-9.
Gilpin et al., "Perfusion decellularization of human and porcine lungs: Bringing the matrix to clinical scale," Journal of Heart and Lung Transplantation, Mar. 2014, 33: 298-308.
Godin et al., "Decreased Laminin Expression by Human Lung Epithelial Cells and Fibroblasts Cultured in Acellular Lung Scaffolds from Aged Mice," PloS One, 2016, 11(3):e0150966.
Gomi et al., "Activation of NOTCH1 or NOTCH3 signaling skews human airway basal cell differentiation toward a secretory pathway," PloS one, Feb. 2015, 10: e0116507.
Gordon et al., "Mechanical Allostery: Evidence for a Force Requirement in the Proteolytic Activation of Notch," Developmental Cell, 2015, 33: 729-736.
Granger et al., "Dynamics and control of transmicrovascular fluid exchange," Edema, 1984, 8:189-228.
Groß et al., "Improved generation of patient-specific induced pluripotent stem cells using a chemically-defined and matrigel-based approach," Curr Mol Med., Jun. 2013,13:765-76.
Guseh et al., "Notch signaling promotes airway mucous metaplasia and inhibits alveolar development," Development, May 2009, 136: 1751-1759.
Guyette et al, "Perfusion decellularization of whole organs," Nat Protoc, 2014, 9: 1451-1468.
Hackett et al., "The human airway epithelial basal cell transcriptome," PloS one, May 2011, 6: e18378.
Hoganson et al., "Tissue Engineering and Organ Structure: A Vascularized Approach to Liver and Lung," Pediatric Research, May 2008, 63(5):520-526.
Hong et al., "Basal cells are a multipotent progenitor capable of renewing the bronchial epithelium," The American Journal of Pathology 2004, 164: 577-588.
Hong et al., "In vivo differentiation potential of tracheal basal cells: evidence for multipotent and unipotent subpopulations," American Journal of Physiology Lung Cellular and Molecular Physiology, 2004, 286: L643-649.
Hou et al., "Pluripotent Stem Cells Induced from Mouse Somatic Cells by Small-Molecule Compounds," Science, Jul. 2013, 341:651-654.
Huang et al., The in vitro generation of lung and airway progenitor cells from human pluripotent stem cells, Nature Protocols, Mar. 2015, 10: 413-425.
Ichii et al., Current status of islet cell transplantation, J. Hepatobiliary Pancreat. Surg., 2009, 16:101-112.
Inayama et al., "The differentiation potential of tracheal basal cells," Laboratory Investigation; a Journal of Technical Methods and Pathology, 1988, 58: 706-717.
Ingenito et al., "Design and testing of biological scaffolds for delivering reparative cells to target sites in the lung," J Tissue Eng Regen Med., 2010, 4: 259-272.
International Preliminary Report on Patentability and Written Opinion in International Application No. PCT/US2010/037379, dated Dec. 6, 2011, 8 pages.
International Preliminary Report on Patentability and Written Opinion in International Application No. PCT/US2010/054689, dated May 1, 2012, 9 pages.
International Preliminary Report on Patentability in International Application No. PCT/US2015/020605, dated Sep. 14, 2016.
International Search Report and Written Opinion in International Application No. PCT/US2010/037379, dated Mar. 1, 2011, 9 pages.
International Search Report and Written Opinion in International Application No. PCT/US2010/054689, dated Jul. 11, 2011, 13 pages.
International Search Report and Written Opinion in International Application No. PCT/US2016/051049, dated Dec. 12, 2016, 13 pages.
International Search Report and Written Opinion dated May 26, 2015 in International Application No. PCT/US2015/020605, 13 pgs.
International Search Report in International Application No. PCT/US2010/23213, dated Aug. 12, 2010, 4 pages.
Jain et al., "Plasticity of Hopx(+) type I alveolar cells to regenerate type II cells in the lung," Nature Communications, 2015, 6: 6727.
James et al., "Expansion and maintenance of human embryonic stem cell-derived endothelial cells by TGFbeta inhibition is Id 1 dependent," Nat Biotechnol, Feb. 2010, 28: 161-166.
Japanese Office Action in Japanese Application No. 2012-514170, dated Sep. 16, 2014, 14 pages.
Karp et al., "An in vitro model of differentiated human airway epithelia. Methods for establishing primary cultures," Methods in Molecular Biology, 2002, 188: 115-137.
Kim et al., "Identification of bronchioalveolar stem cells in normal lung and lung cancer," Cell, Jun. 2005, 121: 823-835.
Korean Office Action in Korean Application No. 2012-7000278, dated Jul. 14, 2016, 12 pages (with English translation).

(56) References Cited

OTHER PUBLICATIONS

Kotton and Morrisey, "Lung regeneration: mechanisms, applications and emerging stem cell populations," Nature Medicine, Aug. 2014, 20: 822-832.

Li et al., "A Single Use, Scalable Perfusion Bioreactor System," BioProcess International, Supplement, 2009.

Li et al., "Generation of iPSCs from mouse fibroblasts with a single gene, Oct4, and small molecules," Cell Res., Jan. 2011, 21:196-204.

Liao et al, "Effects of Decellularization on the Mechanical and Structural Properties of the Porcine Aortic Valve Leaflet," Biomaterials, Mar. 2008, 29(8): 1065-74.

Lin and Ying, "Mechanism and method for generating tumor-free iPS cells using intronic microRNA miR-302 induction," Methods Mol Biol., 2013, 936:295-312.

Lin et al., "Biocompatibility of Poly-D2009L-lactic acid (PDLLA) for Lung Tissue Engineering," Journal of Biomaterials Applications, 2006, 21:109-118.

Lin et al., "Homo- and heterotypic fibrillin-1 and -2 interactions constitute the basis for the assembly of microfibrils," J. Biol. Chem, Dec. 2002, 277: 50795-50804.

Liu et al., "ROCK inhibitor and feeder cells induce the conditional reprogramming of epithelial cells," The American Journal of Pathology, Feb. 2012, 180: 599-607.

Longmire et al., "Efficient derivation of purified lung and thyroid progenitors from embryonic stem cells," Cell Stem Cell, 2012, 10: 398-411.

Macchiarini et al., "Clinical transplantation of a tissue-engineered airway," Lancet, 2008, 372:2023-2030.

Maghsoudlou al., "Preservation of micro-architecture and angiogenic potential in a pulmonary acellular matrix obtained using intermittent intra-tracheal flow of detergent enzymatic treatment," Biomaterials, Sep. 2013, 34(28):6638-48.

Malik and Rao, "A Review of the Methods for Human iPSC Derivation," Methods Mol Biol., 2013, 997:23-33.

McBride et al., "Lung growth and airway function after lobectomy in infancy for congenital lobar emphysema," The Journal of Clinical Investigation, Nov. 1980, 66(5):962-70.

Meiners et al., "Hallmarks of the ageing lung," The European Respiratory Journal, Mar. 2015, 45(3):807-27.

Melero-Martin et al., "In vivo vasculogenic potential of human blood-derived endothelial progenitor cells," Blood, Jun. 2007, 109: 4761-4768.

Mercer et al., "Cell number and distribution in human and rat airways," American Journal of Respiratory Cell and Molecular Biology, Jun. 1994, 10: 613-624.

Midwood and Orend, "The role of tenascin-C in tissue injury and tumorigenesis," Journal of Cell Communication and Signaling, Oct. 2009, 3:287-310.

Mondrinos et al., "Engineering Three-Dimensional Pulmonary Tissue Constructs," Tissue Engineering, 2006, 12(4):717-728.

Mou et al., "Generation of multipotent lung and airway progenitors from mouse ESCs and patient-specific cystic fibrosis iPSCs," Cell Stem Cell, 2012, 10: 385-397.

Musah et al., "Repair of tracheal epithelium by basal cells after chlorine-induced injury," Respiratory Research, 2012, 13: 107.

Nichols et al., "Giving new life to old lungs: methods to produce and assess whole human paediatric bioengineered lungs," J Tissue Eng Regen Med, Jan. 2016, 11: 2136-2152.

Nichols et al., "Engineering of a Complex Organ Progress Toward Development of a Tissue-engineered Lung," Proceedings of the American Thoracic Society, 2008, 5:723-730.

Nichols et al., "Production and assessment of decellularized pig and human lung scaffolds," Tissue Eng Part A, Sep. 2013, 19(17-18):2045-62.

Okano et al., "Steps toward safe cell therapy using induced pluripotent stem cells," Circ Res., Feb. 2013, 112(3):523-33.

O'Koren et al., "Loss of basal cells precedes bronchiolitis obliterans-like pathological changes in a murine model of chlorine gas inhalation," American Journal of Respiratory Cell and Molecular Biology, 2013, 49: 788-797.

O'Neill et al., "Decellularization of human and porcine lung tissues for pulmonary tissue engineering," Ann Thorac Surg., Sep. 2013, 96(3): 1046-55.

Ott et al., "Perfusion-decellularized matrix: using nature's platform to engineer a bioartificial heart," Nature Medicine, 2008, 14(2):213-221.

Ott et al., "Regeneration and orthotopic transplantation of a bioartificial lung," Nat Med, Aug. 2010,16(8):927-33.

Park et al., "Reprogramming of human somatic cells to pluripotency with defined factors," Nature, Jan. 2008, 451 :141-146.

Pasque et al., "Standardizing thoracic organ procurement for transplantation," J Thorac Cardiovasc Surg., Jan. 2010, 139(1):13-7.

Petersen et al., "Tissue-Engineered Lungs for in Vivo Implantation," Science, Jul. 2010, 329: 538-541.

Petersen et al., "Bioreactor for the long-term culture of lung tissue," Cell Transplant, 2011, 20(7):1117-26.

Petersen, "In Vitro Development of Engineered Lung Tissue," Duke University Doctoral Dissertation, 2009, 283 pages.

Pezzulo et al., "The air-liquid interface and use of primary cell cultures are important to recapitulate the transcriptional profile of in vivo airway epithelia," American Journal of Physiology Lung Cellular and Molecular Physiology, 2011, 300: L25-31.

Polacheck et al., "Interstitial flow influences direction of tumor cell migration through competing mechanisms," PNAS, 2011, 108: 11115-11120.

Price et al., "Development of a decellularized lung bioreactor system for bioengineering the lung: the matrix reloaded," Tissue Eng Part A, Aug. 2010, 16(8):2581-91.

Rawlins and Hogan, "Epithelial stem cells of the lung: privileged few or opportunities for many?," Development, 2006, 133: 2455-2465.

Reed et al., "Stem cell-derived endothelial cells for cardiovascular disease: a therapeutic perspective," Br J Clin Pharrnacol, Apr. 2013, 75(4):897-906.

Ren et al., "Engineering pulmonary vasculature in decellularized rat and human lungs," Nature Biotechnology, Oct. 2015, 33: 1097-1102.

Rey-Santano et al., "Effect of Surfactant and Partial Liquid Ventilation Treatment on Gas Exchange and Lung Mechanics in Immature Lambs: Influence of Gestational Age," PLOS One, 2013, 8:e56127.

Rimensberger, "Neonatal respiratory failure," Current Opinion in Pediatrics, 2002, 14:315-321.

Rock et al., "Airway basal stem cells: a perspective on their roles in epithelial homeostasis and remodeling," Disease Models & Mechanisms, 2010; 3: 545-556.

Rock et al., "Basal cells as stem cells of the mouse trachea and human airway epithelium," PNAS, 2009, 106: 12771-12775.

Rock et al., "Notch-dependent differentiation of adult airway basal stem cells," Cell Stem Cell, Jun. 2011, 8: 639-648.

Rojanarat et al., "Isoniazid Proliposome Powders for Inhalation—Preparation, Characterization and Cell Culture Studies," International Journal of Molecular Sciences, 2011, 12:4414-4434.

Rosen et al., "Preconditioning allows engraftment of mouse and human embryonic lung cells, enabling lung repair in mice," Nature Medicine, 2015, 21: 869-879.

Sato et al., "Replacement of the left main bronchus with a tissue-engineered prosthesis in a canine model," Ann. Thorac. Surg., 2008, 86:422-428.

Second Chinese Office Action in Chinese Application No. 201080032724.4, dated Sep. 24, 2013, 9 pages (with English translation).

Sharpless and Sherr, "Forging a signature of in vivo senescence," Nature Reviews Cancer, Jul. 2015, 15: 397-408.

Sokocevic et al., "The effect of age and emphysematous and fibrotic injury on the re-cellularization of de-cellularized lungs," Biomaterials, 2013, 34(13):3256-69.

Song and Ott, "Bioartificial lung engineering," Am J Transplant, Feb. 2012,12(2):283-8.

Song et al., "Enhanced in vivo function of bioartificial lungs in rats," Ann Thorac Surg., 2011, 92(3):998-1005.

Song et al., "Organ engineering based on decellularized matrix scaffolds," Trends in Molecular Medicine, 2011, 17(8):424-432.

(56) References Cited

OTHER PUBLICATIONS

Staudt et al., "Airway Basal stem/progenitor cells have diminished capacity to regenerate airway epithelium in chronic obstructive pulmonary disease," American Journal of Respiratory and Critical Care Medicine, 2014, 190: 955-958.
Stripp and Reynolds, "Maintenance and repair of the bronchiolar epithelium," Proceedings of the American Thoracic Society, 2008, 5: 328-333.
Supplementary Search Report in European Application No. 10784139, dated Aug. 29, 2013, 8 pages.
Takahashi et al., "Induction of Pluripotent Stem Cells from Adult Human Fibroblasts by Defined Factors," Cell, Nov. 2007,131 :861-72.
Tapias and Ott, "Decellularized scaffolds as a platform for bioengineered organs," Current Opinion in Organ Transplantation, 2014, 19(2):145-52.
Teebken et al., "Tissue Engineering of Vascular Grafts. Human Cell Seeding of Decellularised Porcine Matrix," Eur. J. Vasc. Endovasc. Surg., Apr. 2000, 19:381-86.
Teixeira et al., "Stochastic homeostasis in human airway epithelium is achieved by neutral competition of basal cell progenitors," eLife, 2013, 2: e00966.
Thannickal et al., "Blue Journal Conference. Aging and Susceptibility to Lung Disease," American Journal of Respiratory and Critical Care Medicine, 2015, 191(3):261-9.
The Decision of Final Rejection of the Application in Chinese Application No. 201080032724.4, dated Jan. 27, 2015, 7 pages (English translation).
Third Chinese Office Action in Chinese Application No. 201080032724.4, dated May 9, 2014, 8 pages (English translation).
Toni et al., "The bioartificial thyroid: a biotechnological perspective in endocrine organ engineering for transplantation replacement," Acta Bio Medica, 2007, 78(Sunn 1):129-155.
Tsao et al., "γ-Secretase Activation of Notch Signaling Regulates the Balance of Proximal and Distal Fates in Progenitor Cells of the Developing Lung," Journal of Biological Chemistry, Oct. 2008, 283: 29532-29544.
U.S. Final Office Action in U.S. Appl. No. 13/375,260, dated Oct. 25, 2013, 15 pages.
U.S. Final Office Action in U.S. Appl. No. 13/504,358, dated Jul. 3, 2014, 10 pages.
U.S. Final Office Action in U.S. Appl. No. 14/559,401, dated Feb. 8, 2017, 11 pages.
U.S. Non-Final Office Action in U.S. Appl. No. 13/375,260, dated Feb. 1, 2013, 11 pages.
U.S. Non-Final Office Action in U.S. Appl. No. 13/504,358, dated Dec. 9, 2013, 13 pages.
U.S. Notice of Allowance in U.S. Appl. No. 13/375,260, dated Nov. 26, 2014, 10 pages.
Vandenbroucke et al., "Regulation of Endothelial Junctional Permeability," Ann. N.Y. Acad. Sci., 2008, 1123:134-145.
Vaughan et al., "Lineage-negative progenitors mobilize to regenerate lung epithelium after major injury", Nature, 2015, 517: 621-625.
Venkateswaran et al., "Measurement of extravascular lung water following human brain death: implications for lung donor assessment and transplantation," Eur J Cardiothorac Surg., Jun. 2013, 43(6):1227-32.
Venkateswaran et al., "The proinflammatory environment in potential heart and lung donors: prevalence and impact of donor management and hormonal therapy," Transplantation, Aug. 2009, 88(4):582-8.
Venuta et al., "Evolving Techniques and Perspectives in Lung Transplantation," Transplantation Proceedings, Jul.-Aug. 2005, 37(6):2682-2683.

Wagner et al., "Comparative decellularization and recellularization of normal versus emphysematous human lungs," Biomaterials, Mar. 2014, 35: 3281-3297.
Wansleeben et al., "Stem cells of the adult lung: their development and role in homeostasis, regeneration, and disease," Wiley Interdisciplinary Reviews Developmental Biology, 2013, 2: 131-148.
Watson et al., "Clonal Dynamics Reveal Two Distinct Populations of Basal Cells in Slow-Turnover Airway Epithelium," Cell Reports, 2015, 12: 90-101.
Whitsett et al., "Human surfactant protein B: structure, function, regulation, and genetic disease," Physiological Reviews, Oct. 1995, 75(4):749-57.
Written Opinion of the International Search Authority in International Application No. PCT/US2010/23213, dated May 24, 2010, 6 pages.
Xu et al., "Notch signaling in lung development and disease," Advances in Experimental Medicine and Biology, 2012, 727: 89-98.
Yang and Conte, "Finer techniques in lung transplantation," Transplantation Proceedings, Nov. 2000, 32(7): 1521-1522.
Yang et al., "Expression of mutant BMPR-II in pulmonary endothelial cells promotes apoptosis and a release of factors that stimulate proliferation of pulmonary arterial smooth muscle cells," Pulmonary Circulation, 2011, 1(1):103-110.
Yates et al., "Skin wound healing and scarring: fetal wounds and regenerative restitution," Birth Defects Research Part C, Embryo Today, Dec. 2012, 96(4):325-33.
Yoshida et al., "Surgical Technique of Experimental Lung Transplantation in Rabbits," Ann Thorac Cardiovasc Surg., Jan. 2005, 11(1):7-11.
Yu et al., "Induced pluripotent stem cell lines derived from human somatic cells," Science, Nov. 2007, 318: 1917-20.
Zahm et al., "Cell migration and proliferation during the in vitro wound repair of the respiratory epithelium," Cell Motility and the Cytoskeleton, 1997, 37: 33-43.
Zhu et al., "Partial liquid ventilation decreases tissue and serum tumor necrosis factor-a concentrations in acute lung injury model of immature piglet induced by oleic acid," Chinese Medical Journal, 2012, 125(1):123-128.
Zhu et al., "Reprogramming of Human Primary Somatic Cells by OCT4 and Chemical Compounds," Cell Stem Cell., Dec. 2010, 7:651-5.
Zuo et al., "p63(+)Krt5(+) distal airway stem cells are essential for lung regeneration," Nature, 2015, 517: 616-620.
Gilpin et al. "Regenerative potential of human airway stem cells in lung epithelial engineering," Biomaterials, Sep. 2016, 108: 111-119.
International Search Report and Written Opinion in International Application No. PCT/US2017/031076, dated Dec. 29, 2017, 11 pages.
EP Extended European Search Report in European Appln. No. 17799867.1, dated Jan. 7, 2020, 12 pages.
Karp et al., "An in Vitro Model of Differentiated Human Airway Epithelia: Methods for Establishing Primary Cultures" Epithelial Cell Culture Protocols, 2002, 115-137.
Lemon et al., "The development of the bio artificial lung," British Medical Bulletin, Jun. 2014, 110(1):35-45.
Mendez et al., "Epithelial Cell Differentiation of Human Mesenchymal Stromal Cells in Decellularized Lung Scaffolds," Tissue Engineering Part A., Jun. 2014, 20(11-12):1735-46.
Schilders et al., "Regeneration of the lung: Lung stem cells and the development of lung mimicking devices", Respiratory Research, Dec. 2016, 17(1):44, 16 pages.
Shojaie et al., "Acellular Lung Scaffolds Direct Differentiation of Endoderm to Functional Airway Epithelial Cells: Requirement of Matrix-Bound HS Proteoglycans", Stem Cell Reports, Mar. 2015, 4(3):419-430.

\* cited by examiner

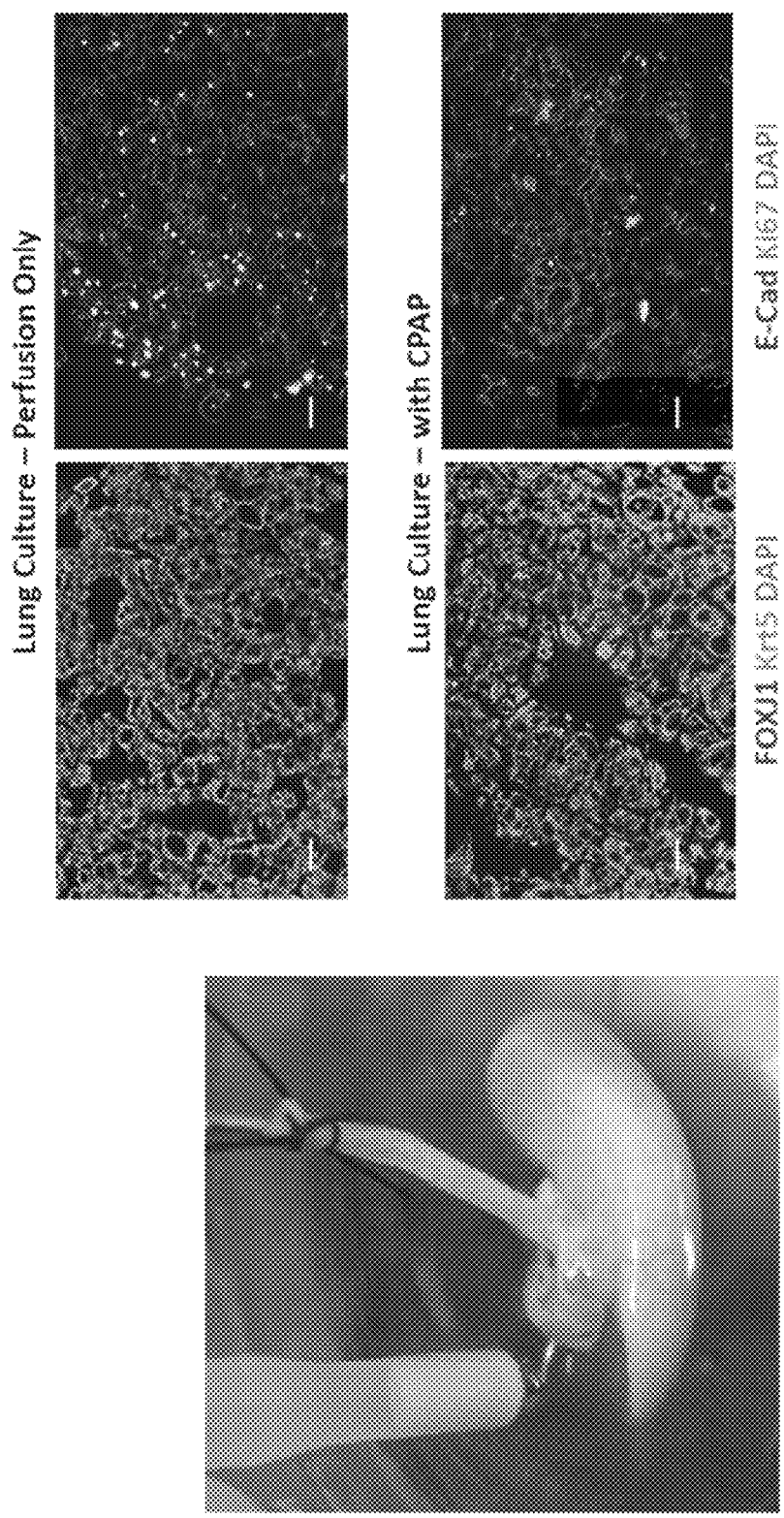

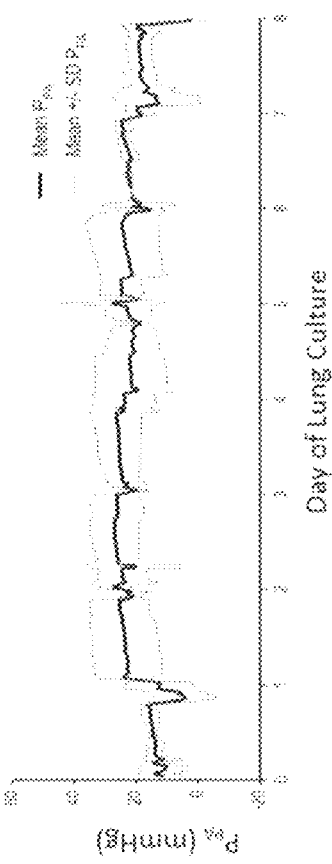
FIG. 5C
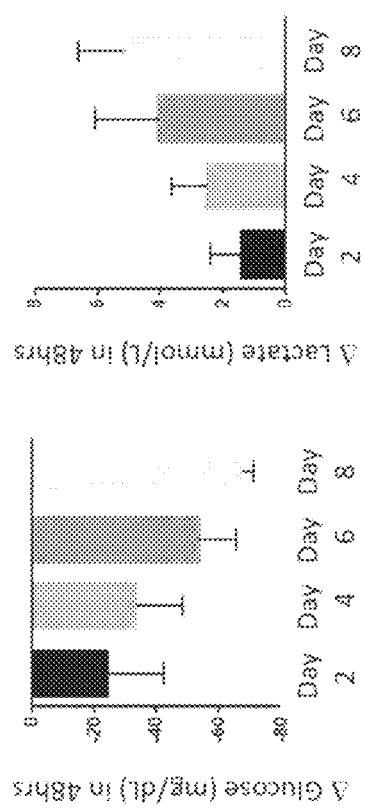
FIG. 5D
FIG. 5E

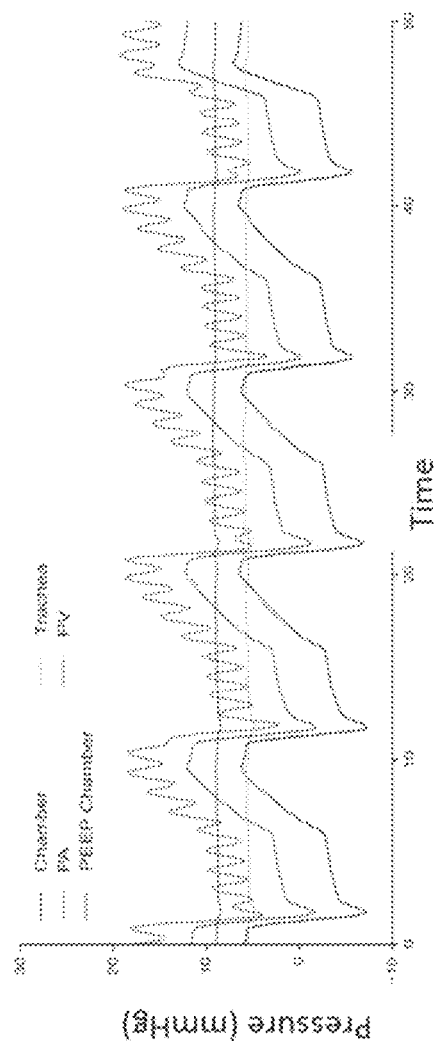
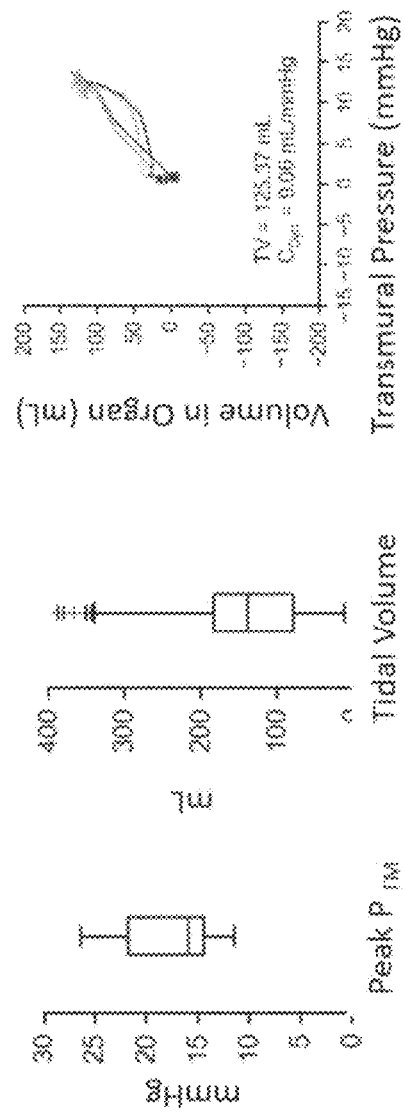
FIG. 5F  FIG. 5G  FIG. 5H  FIG. 5I

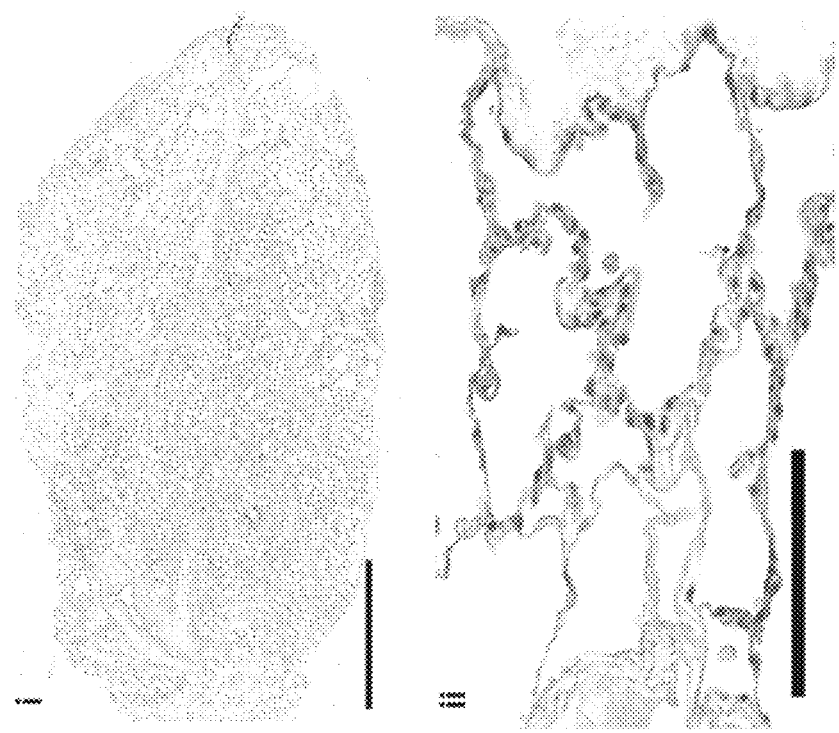
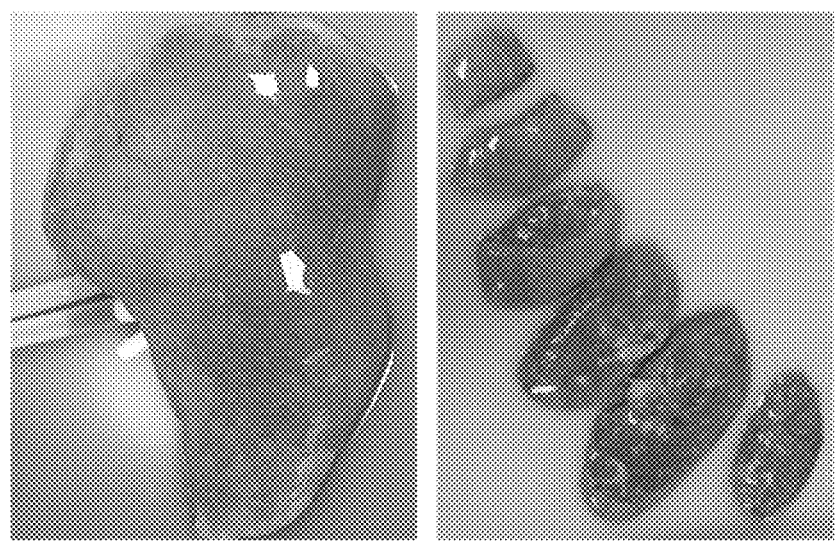
FIG. 6B
FIG. 6A

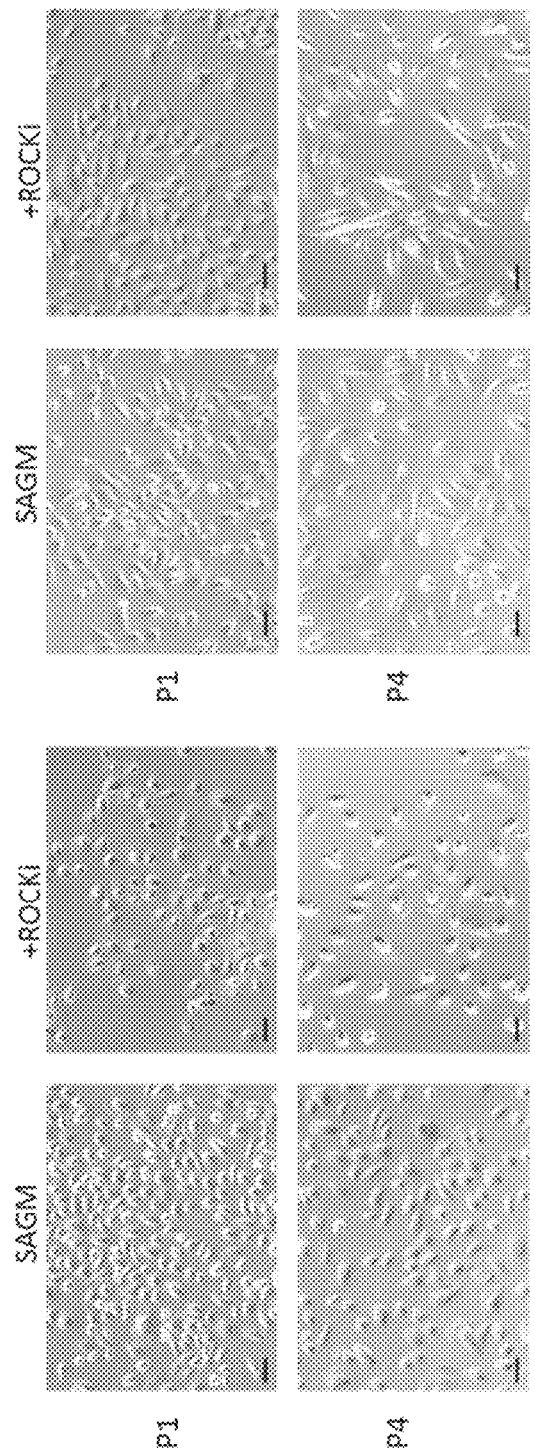

| UniProt Accession | Protein name | Gene name | Matrisome Subcategory | Neonatal/Adult fold change | corrected p-value |
|---|---|---|---|---|---|
| P35625 | Metalloproteinase inhibitor 3 | TIMP3 | ECM Regulators | 0.001 | 2.6E-02 |
| P02760 | Protein AMBP | AMBP | ECM Regulators | 0.017 | 2.6E-02 |
| P51888 | Prolargin | PRELP | Proteoglycans | 0.019 | 2.5E-02 |
| P55107 | Bone morphogenetic protein 3B | GDF10 | Secreted Factors | 0.028 | 5.4E-03 |
| P35858 | Insulin-like growth factor-binding protein complex acid labile subunit | IGFALS | ECM Glycoproteins | 0.040 | 4.6E-05 |
| P04085 | Platelet-derived growth factor subunit A | PDGFA | Secreted Factors | 0.101 | 2.0E-03 |
| P02746 | Complement C1q subcomponent subunit B | C1QB | ECM-affiliated Proteins | 0.221 | 3.0E-03 |
| Q9NT22 | EMILIN-3 | EMILIN3 | ECM Glycoproteins | 2.290 | 2.1E-01 |
| P07942 | Laminin subunit beta-1 | LAMB1 | ECM Glycoproteins | 2.392 | 1.3E-01 |
| P24821 | Tenascin | TNC | ECM Glycoproteins | 2.639 | 4.1E-01 |
| Q5H8C1 | FRAS1-related extracellular matrix protein 1 | FREM1 | ECM-affiliated Proteins | 3.320 | 2.4E-02 |
| Q14031 | Collagen alpha-6(IV) chain | COL4A6 | Collagens | 3.461 | 1.5E-01 |
| Q9Y4K0 | Lysyl oxidase homolog 2 | LOXL2 | ECM Regulators | 9.918 | 2.1E-01 |
| Q6ZWJ8 | Kielin/chordin-like protein | KCP | ECM Glycoproteins | 11.040 | 6.5E-02 |
| Q86XX4 | Extracellular matrix protein FRAS1 | FRAS1 | ECM Glycoproteins | 16.558 | 2.6E-01 |
| P02458 | Collagen alpha-1(II) chain | COL2A1 | Collagens | 22.579 | 4.2E-01 |
| Q75N90 | Fibrillin-3 | FBN3 | ECM Glycoproteins | 59.812 | 3.5E-02 |
| P35556 | Fibrillin-2 | FBN2 | ECM Glycoproteins | 202.742 | 2.8E-02 |
| Q5SZK8 | FRAS1-related extracellular matrix protein 2 | FREM2 | ECM-affiliated Proteins | 367.195 | 2.1E-01 |

FIG. 14B

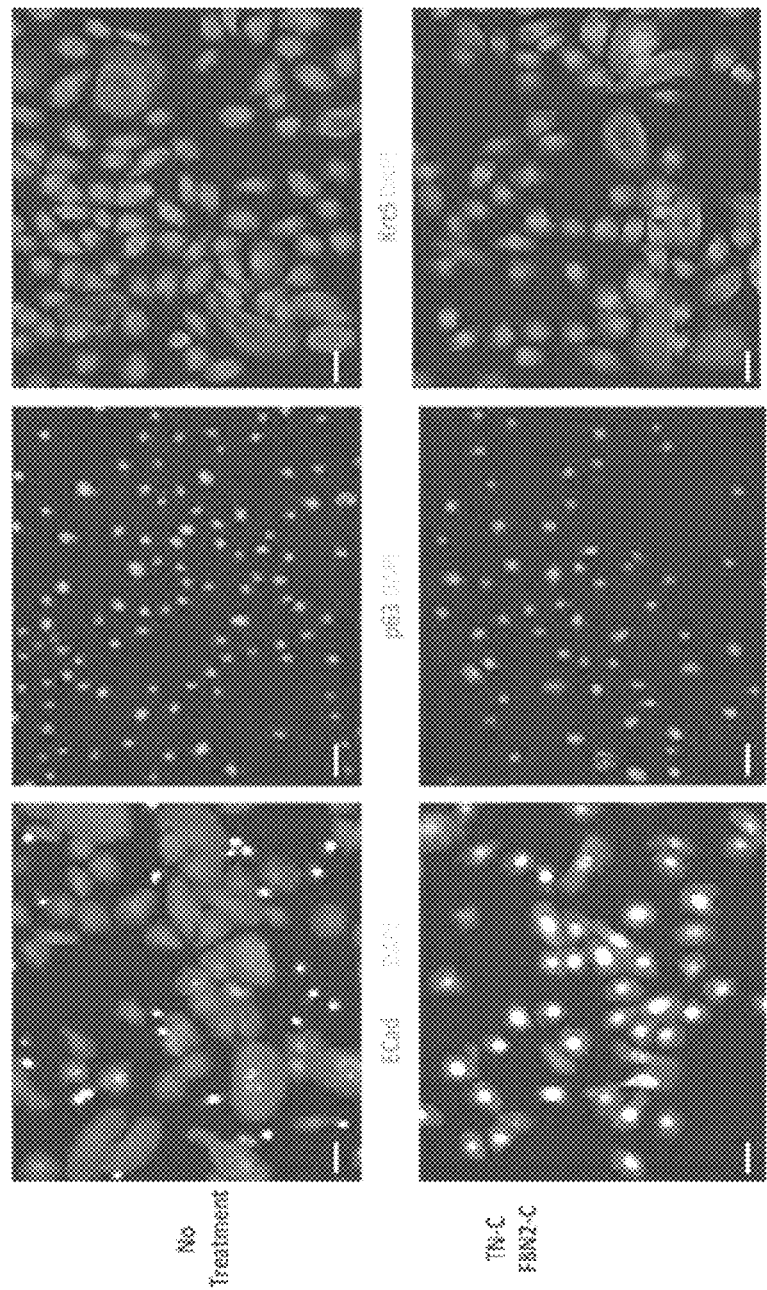

HUMAN AIRWAY STEM CELLS IN LUNG EPITHELIAL ENGINEERING

CLAIM OF PRIORITY

This application is a continuation of PCT/US2017/031076, filed May 4, 2017, which claims the benefit of U.S. Provisional Patent Application Ser. Nos. 62/337,041, filed on May 16, 2016; 62/426,146, filed on Nov. 23, 2016; and 62/483,760, filed on Apr. 10, 2017. The entire contents of the foregoing are hereby incorporated by reference.

FEDERALLY SPONSORED RESEARCH OR DEVELOPMENT

This invention was made with Government support under Grant Nos. OD008749 and HL108678 awarded by the National Institutes of Health. The Government has certain rights in the invention.

TECHNICAL FIELD

Provided herein are methods of using human airway stem cells in lung epithelial engineering, optionally wherein the cells are contacted with a gamma secretase inhibitor, bioartificial airway organs produced thereby, and the use thereof, e.g., for transplantation.

BACKGROUND

Lung transplants represent a final hope for many patients experiencing conditions typified by lung failure, e.g., chronic obstructive pulmonary disease (COPD), cystic fibrosis, pulmonary hypertension, lung cancers, and congenital lung diseases. Typical wait time for a lung transplant can be two years or more, resulting in a 30% mortality rate for those on the waiting list. The development of techniques to engineer organs for transplantation may ultimately provide a solution for end-stage organ failure without the risk of rejection.

SUMMARY

Building upon the process of whole organ perfusion decellularization, the present inventors aimed to utilize primary human donor lung tissue-derived cells to repopulate and regenerate native lung scaffolds.

As shown herein, a proliferative basal epithelial stem cell population was isolated and expanded in culture, and robust recellularization of both rodent and human lung extracellular matrix (ECM) was achieved. Differentiation toward a ciliated airway epithelial phenotype was demonstrated both in vitro and in ex vivo whole rodent lung recellularization and biomimetic culture. Induction of a distal epithelial phenotype was achieved by inhibition of the Notch pathways through γ-secretase. Increased surfactant protein-B and C expression was demonstrated by mRNA analysis in vitro, in human ECM slice culture, and in whole rodent lung culture. Recellularization of isolated human lung lobes, coupled with extended ex vivo biomimetic culture, further confirmed the regenerative capacity of this cell population. Functional analysis of the recellularized lung constructs verified cell viability and metabolic activity throughout culture, as well as dynamic organ compliance and gas exchange. On final tissue analysis, extensive re-epithelialization with physiologic tissue architecture and morphology was observed.

These results demonstrate the regenerative potential and bi-lineage capacity of human airway stem cells, which are useful in whole lung tissue bioengineering and ex vivo organ culture.

In addition, the behavior of basal epithelial stem cells (BESCs) isolated from adult human lung tissue cultured on acellular ECM derived from neonatal (aged<1 week) or adult lung donors (n=3 donors per group) was evaluated. A significant difference in cell proliferation and survival was found. In-depth proteomic analysis of the lung scaffolds was performed to quantify proteins significantly enriched in the neonatal ECM, and identified the glycoproteins Fibrillin-2 (FBN-2) and Tenascin-C (TN-C) as potential mediators of the observed effect. BESCs cultured on Collagen Type IV coated plates, supplemented with FBN-2 and/or TN-C demonstrated significantly increased proliferation and decreased cellular senescence; (note that this difference was also found when compared to untreated plates (no Collagen IV coating). No significant increase in epithelial-to-mesenchymal transition was observed. In vitro wound closure was also increased on FBN-2 and/or TN-C. Decellularized lung scaffolds pre-treated with FBN-2 and/or TN-C prior to re-epithelialization supported greater epithelial proliferation and tissue remodeling. BESC distribution, matrix alignment, and overall tissue morphology was improved on treated lung scaffolds, after 3 and 7 days of ex vivo lung culture. These results demonstrate that scaffold re-epithelialization is enhanced on neonatal lung ECM, and that supplementation of FBN-2 and TN-C to the native scaffold is a valuable tool in lung tissue regeneration.

Thus, provided herein are methods for providing a bioartificial lung organ. The methods include providing a population of proliferative basal stem cells from a human donor wherein the cells are Krt5$^+$p63$^+$ cells, preferably obtained from the airway of the donor; optionally maintaining and expanding the cells in culture for up to five passages (e.g., wherein cells were passaged at 60-100%, e.g., 80%, confluency), optionally in the absence of a ROCK inhibitor; providing a (cell-free) lung tissue matrix including an airway and substantial vasculature; seeding the lung tissue matrix with the stem cells through the airway, and with endothelial cells through the vasculature; and maintaining the matrix under conditions sufficient for the formation of a functional epithelium in the airways and functional vasculature, wherein maintaining the matrix comprises providing the lung tissue matrix with wet ventilation using a liquid media comprising a notch inhibitor, e.g., a gamma secretase inhibitor, for a time sufficient for a first desired degree of organ maturation to occur to produce a wet-matured organ; and optionally maintaining a substantially constant fluid level in the organ chamber during wet ventilation.

In some embodiments, the organ chamber comprises a chamber pressure sensor and a bi-directional drainage chamber pump each controlled by a control module that controls the bi-directional drainage pump in response to data transmitted by the chamber pressure sensor.

In some embodiments, the methods include preventing a transpulmonary pressure gradient by equilibrating a pressure level in the venous line with a pressure level in a media reservoir.

In some embodiments, the organ chamber further comprises a pneumatic pressure control module connected to the organ chamber, wherein the pneumatic pressure control module: generates negative pressure in the organ chamber during an inspiration phase; maintains the organ chamber pressure for a plateau phase; and generates positive pressure in the organ chamber during an expiration phase.

In some embodiments, wet ventilation comprises connecting the tracheal line to a media reservoir, in which the tracheal line includes a bi-directional tracheal pump connected to the controller; inflating the lung tissue matrix with media using the bi-directional tracheal pump; and deflating the lung tissue matrix using the bi-directional tracheal pump to withdraw media from the lung tissue matrix, wherein the media is continuously refreshed during wet ventilation.

In some embodiments, the wet ventilation comprises connecting the tracheal line to a media reservoir, in which the tracheal line includes a first pump and a second pump each connected to the controller; inflating the lung tissue matrix with media using the first pump; and deflating the lung tissue matrix using the second pump to withdraw media from the lung tissue matrix, wherein the media is continuously refreshed during wet ventilation. In some embodiments, the controller controls the bi-directional tracheal pump in response to data transmitted by a tracheal pressure sensor connected to the tracheal line.

In some embodiments, the methods include providing wet ventilation using a liquid media comprising a notch inhibitor for at least 2, 5, 7, or 10 days, optionally followed by additional wet ventilation using a liquid media not comprising a notch inhibitor.

In some embodiments, the lung tissue matrix comprises tenascin-c (TN-C), e.g., supplemental tenascin-c in addition to any tenascin-c that may be naturally present in a matrix derived from a decellularized organ scaffold; the methods can include contacting the lung tissue matrix with tenascin-c prior to cell seeding, e.g., delivery of a solution comprising Tenascin-c, e.g., about 0.5-10 ug/ml Tenascin-C, to the lung tissue matrix scaffold airway.

In some embodiments, the lung tissue matrix comprises Fibrillin-2 (FBN-2), e.g., supplemental FBN-2 in addition to any FBN-2 that may be naturally present in a matrix derived from a decellularized organ scaffold; the methods can include contacting the lung tissue matrix with FBN-2 prior to cell seeding, e.g., delivery of a solution comprising FBN-2, e.g., about 0.1 to 100 ug/ml FBN-2, e.g., 0.5-50, 1-20, 5-15, 5-20, 10-20 ug/ml FBN-2, to the lung tissue matrix scaffold airway.

In some embodiments, the lung tissue matrix comprises both TN-C and FBN-2.

Also provided herein are functional lungs produced by a method described herein. In some embodiments, the organ is a full lung or a vascularized portion thereof.

Also provided herein are methods for treating a subject having impaired or reduced lung capacity that include transplanting a functional lung produced by a method described herein into the subject.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

The patent or application file contains at least one drawing executed in color. Copies of this patent or patent application publication with color drawing(s) will be provided by the Office upon request and payment of the necessary fee.

FIGS. 2A-F. Differentiation toward ciliated airway epithelium by air-liquid interface culture. (A) Primary human lung epithelial stems cells at Air-Liquid Interface (ALI), Day 21. Induction of ciliogenesis is observed by Haematoxyalin and Eosin staining. Scale bar=25 μm. (B) Immunofluorescent images demonstrate preservation of the basal stem cell population (Krt5/p63+), functional ciliogenesis (FOXJ1 and Acetylated α Tubulin) and tight junction formation (E-Cadherin) at ALI. Scale bar=25 μm. (C) Air-liquid interface on decellularized lung matrix by continuous positive airway pressure (CPAP) model (20 mmHg airway pressure for 7 days following 7 days of vascular perfusion-only culture). (D) Immunofluorescent images demonstrate maintenance of basal stem cell population (Krt5), induction of FOXJ1 expression, enhanced tight junction formation (E-Cadherin), and decrease in proliferation (Ki67) compared to lung prior to CPAP (Day 7 vs Day 14). Scale bar=50 μm. (E) Western blot analysis of E-Cadherin protein levels at day 14 in lung tissue +CPAP or −CPAP (vascular perfusion-only). (F) Quantitative PCR analysis of gene expression in recellularized lungs following recellularization and vascular perfusion only for 7 days, compared to lungs at Day 14 (additional 7 days of CPAP or perfusion only). Data from 3 independent recellularized lungs is shown. n=3 independent tissue samples analyzed per lung, per time point, in experimental triplicates. Normalized to β-actin expression and relative to normal cadaveric lung tissue control. All error bars represent standard deviation. Analyzed by 1-way ANOVA with Tukey's multiple comparisons post-test.

FIGS. 6A-H. Analysis of lung tissue recellularization following biomimetic culture. (A) Perfusion of Resazurin containing media to assay cell viability on day 7 of biomimetic culture. Viable cell metabolism of the blue dye is visualized by transition to a pink color, demonstrating extensive cell retention, distribution, and viability after culture. (B) Representative scan of H&E section of recellularized lung tissue (i) scale bar=5 mm and (ii) scale bar=100 µm. (C) Immunofluorescent image of continued E-Cadherin+ epithelial cell proliferation (Ki67+) on Day 7 of culture. Scale bar=50 µm. (D) Quantification of cell proliferation in recellularized lung tissue by Ki67+ staining. Three representative areas were analyzed per lung, with 4 images quantified per area. Error bars represent the standard deviation. Analyzed by 1-way ANOVA, with no significance identified. (E) Immunofluorescent images of recellularized lungs at Day 7 of culture confirming the maintenance of Krt5+p63+ basal cell population and the rare observance of non-adhered proSP-B+ cells. (F) Cell retention and repopulation of large airways following culture, demonstrated by Krt5+, p63+ and E-cadherin+ epithelial cells in recellularized (i-ii) rat and (iii) human lungs. (G) Localization of and organization of CD31+ cells in the vascular capillary compartment of the lung scaffold. Scale bars=50 µm. (H) Quantitative PCR analysis of gene expression of lung tissue on Day 7 or 10 (final day) of culture. Data from 3 independent recellularized lungs cultures is shown, with n=4 unique tissue samples analyzed per lung, in experimental duplicate. Expression normalized to β-actin and relative to normal cadaveric lung tissue control. Gene expression level for cells maintained in vitro is shown for reference. All error bars represent standard deviation. Analyzed by 1-way ANOVA, with no significance identified.

FIGS. 8A-C: Effect of ROCK Inhibitor on Cell Phenotype and Senescence. (A) Gene expression analysis of n=3 individual cell lines at passage 1 and passage 4, with or without the addition of ROCK inhibitor Y27632 (10 Error bars represent standard deviation. No significant differences between untreated and treated (+ROCK) were found by t-test at each passage. (B) Representative image of cells at passage 1 and passage 4, with or without ROCK inhibitor, with Trypan Blue added to culture media. (C) Representative image of cells at passage 1 and passage 4, with or without ROCK inhibitor, stained for senescence-associated β-galactosidase activity at pH 6. Scale bars=50 μm.

FIGS. 14A-B. Quantitative comparison of the matrix proteins in adult and neonatal lung scaffolds. (A) Volcano plot of detected matrix proteins. (B) Details of proteins highlighted in (A).

FIGS. 15A-E. In vitro analysis of BESC response to FBN-2 and TN-C. (A) Gene expression analysis, normalized to β-Actin, and expressed relative to normal adult lung tissue. (B) Immunofluorescent staining (C) Ki67+ quantification (n=3 tissues/group). Scale bar=50 μm (D) In vitro migration assay, representative image and quantification of change in cell-free area over 180 min. Scale bar=100 μm. (E) Expression of Focal Adhesion Kinase (FAK) by BESCs on each coating. Gene expression analysis, normalized to β-Actin, and expressed relative to normal adult lung tissue.

DETAILED DESCRIPTION

Figure 1A:
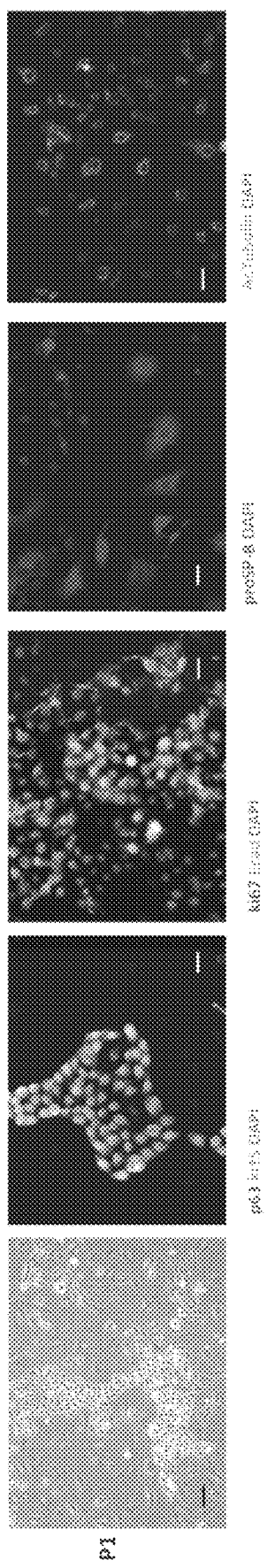
FIGS. 1A-E. Characterization of primary human lung epithelial stem cell expansion in vitro. Bright-field and immunofluorescent images of (A) Passage 1 (P1) and (B) Passage 4 (P4) primary human epithelial cells in vitro, illustrating colony outgrowth with an enrichment of Krt5+ p63+ basal stem cells. Scale bar=100 μm (C) Quantification of Ki67 positive cells in vitro by passage. n=3 images quantified per passage (P1-P4). 1-Way ANOVA compared to Passage 1 (P1), with Dunnet post-test. All error bars represent standard deviation. (D) Flow cytometric quantification of epithelial cell markers at P1 and P4. 2×10$^4$ events collected. Populations gated to exclude doublets and autofluorescent cells. n=3 cell lines per passage (E) Quantitative PCR analysis of gene expression by cell passage. Box plots represent median, plus the first and third quartile. Whiskers represent the 2.5-97.5% data range. n=3 cell lines per passage. Normalized to β-actin expression and relative to normal cadaveric lung tissue control.

Solid organ bioengineering based on native extracellular matrix scaffolds has fueled recent enthusiasm for regenerative medicine approaches to end organ failure (1). The main approach involves combining regenerative cell populations with corresponding biological matrices to form living, functional grafts. To this end, native solid organ extracellular matrix (ECM) scaffolds can be readily generated by perfusion decellularization with specific detergents, rendering a biocompatible framework as a foundation for regeneration (2-7).

Clinically relevant organ recellularization presents significant challenges, both in terms of identifying a cell source and in the establishment of functional biomimetic organ culture conditions to support organ maturation prior to transplantation (8).

An optimal cell source would be easily obtained and expanded in vitro, and would ideally possess the capacity for multi-lineage differentiation. While directed differentiation of induced pluripotent stem cells through key developmental stages presents a promising option for obtaining lung-specified cell populations (9-11), the length of in vitro culture and limited cell numbers restricts their current utility for large-scale organ engineering. While largely quiescent, adult lung tissue has a remarkable capacity for regeneration, owing to a number of facultative stem/progenitor cell populations that become activated in response to tissue damage (12). Airway basal cells, identified by the transcription factor p63 and expression of cytokeratin 5 (Krt5), function as multipotent stem cells of the airway epithelium, and are critical for maintaining airway homeostasis during physiological cell turnover and regeneration (13, 14). This essential cell population comprises 30% of the cells in human airway epithelium (15), and early studies of airway regeneration demonstrated the ability for isolated basal cells to recapitulate a fully differentiated airway epithelium when seeded onto denuded mouse tracheas (16). In response to injury, basal epithelial stem cells can rapidly proliferate and give rise to both ciliated and club cell progeny, confirming their important function in tissue homeostasis and injury repair (17). Lung basal cells can be readily isolated from lung tissue (18, 19) and propagated in culture (20), which makes them a useful target population for tissue engineering applications. The in vitro cultivation of this primary stem cell population also provides an important tool for studying basic biology and tissue regeneration (13), particularly given their capacity for multi-lineage differentiation (21, 22).

Described herein is the isolation of a highly proliferative basal stem cell population from an easily accessible tissue source and demonstrated over 100-fold expansion in vitro. This cell population, identified by $Krt5^+p63^+$ expression, has been studied in animal models of lung repair (23-25) and in human disease (26).

Within the $Krt5^+p63^+$ population, additional distinct subpopulations of basal stem cells may exist, each with a unique role in tissue homeostasis and repair. This includes the recently reported lineage-negative epithelial progenitor (LNEP) cells within normal distal lung, which can specifically proliferate following injury (27). It is unclear whether these rare cellular subsets can act in isolation, or if they require combined signaling and action of other cells in the injured tissue milieu. Mathematical models support a heterogeneous basal stem cell population, proposing approximately equal numbers of multipotent stem cells and committed precursors (28). The role of injury, including source, intensity, and duration, is also an important determinant of cell activation and fate. The origin of the cell population studied, considering age and species as two examples, can also contribute to the regenerative capacity and cell fate. Embryonic lungs at the canalicular stage of development have been recently shown to possess distinct niches enriched with epithelial progenitors surrounded by mesenchymal cells and blood cells, and these cells can be transplanted to injured lungs and differentiation to multiple lineages (29).

Following lung injury, the re-establishment of an intact epithelium is critical to restore lung homeostasis (30). In the present model of lung repair, the decellularized lung scaffold serves as the provisional matrix for epithelial cell migration, recapitulating (at least in part) the processes activated in vivo to cover and repair denuded airway and gas exchange surfaces (31). The physiologic role of basal cells, to help anchor epithelial cells to the matrix and protect the underlying stroma, is aided by their expression of abundant cytoskeletal, junctional and adhesive proteins, which supports their demonstrated utility in re-epithelialization of native lung ECM (32).

Rodent models of airway injury have established a timeline of epithelial repair. After epithelial injury, cell spreading and migration occurs as the primary repair mechanisms in the first 12-24 hours, with proliferation beginning after 24 hours and continuing for several weeks (33). This timeline aligns with the present model of lung repair in ex vivo culture and regeneration. The next step in the repair mechanism would be reestablishment of a pseudostratified epithelium, which can take several weeks to establish (34). The present model of air-liquid interface culture on whole rat lung scaffolds demonstrated the initial upregulation of FOXJ1 and increased tight junction formation at 7 days. Extended bioreactor culture may be required to fully mature the reconstituted epithelium, as in vitro ALI models require 3-4 weeks to recapitulate the mature airway biology (35). Following recellularization and ex vivo culture, no significant pneumocyte lineages were identified within the present reconstituted epithelium. Longer regeneration time, combined with modulation of signaling pathways is likely required to induce committed pneumocyte differentiation from the delivered stem cell population, with animal models demonstrating distal lung regeneration required 50-90 days (27, 36).

Notch signaling plays an essential and complex role in lung epithelial development and homeostasis, and Notch ligands are expressed at very high levels in the lung (37). Lung development requires the precise patterning of multiple cell lineages, of which many fate choices are controlled by direct cell-to-cell communication. During embryonic alveolar development, constitutive over-expression of Notch inhibits the development of distal epithelium, instead promoting cyst formation mainly lacking alveolar markers (38). The requirement for Notch signaling in early lung proximal-distal cell fate decision was also shown following Notch inhibition by DAPT, resulting in an accumulation of $Nk\times2.1^+$ distal lung progenitor cell population (38). As also shown herein, pharmacological inhibition of the Notch pathway through $\gamma$-secretase can induce global transitional toward a type II pneumocyte phenotype in vitro and in ex vivo lung scaffold culture. This confirms a report of 3-D sphere culture of mouse basal stem cells (27). There was also a loss of CCSP-expression observed following Notch inhibition, further highlighting the essential role for Notch activation in basal cell differentiation towards the secretory lineage (39, 40). For organ engineering, precise control of these signals may require pharmaceutical activation or inhibition of the Notch pathway to achieve optimal cell patterning. Further development of advanced bioengineering procedures will be required to specifically deliver these biochemical signals to the specific proximal or distal lung compartment in a dose and time-controlled manner. Mechanical forces also contribute to the activation of Notch signaling exposing the metalloprotease cleavage site and facilitating the subsequent change from the auto-inhibited conformation (41). These mechanical considerations may be of additional significance to cell-cell signaling in 3-dimensional whole organ biomimetic culture vs. traditional 2-D culture. Shear fluid forces resulting from biomimetic organ perfusion may further direct cell organization along the scaffold during culture. Epithelial cells have been shown to migrate along fluid flow streamlines in vitro, which may be directed by paracrine chemokine fields in the local microenvironment (42).

The present model of lung scaffold recellularization and ex vivo regeneration provides a unique and easily accessible tool to further investigate epithelial repair in a systematic manner.

Organ regeneration based on decellularized scaffolds is perhaps the ultimate model of injury and test of cellular repair potential. Given the isolated environment, coupled with the biomimetic stimulus provided by the ex vivo culture of the regenerating organ, it is possible to directly assess the ability of specific cell populations to regenerate native tissue. In the present study, by employing systematic building-blocks approach, a critical step forward is made by demonstrating that a primary isolated airway stem cell population can accomplish extensive tissue regeneration on an acellular lung scaffold, and can be directed toward both proximal and distal epithelial lineages.

This document relates to methods and materials involved in airway organ generation and preservation. Described are methods, devices, cells, and compositions configured to generate functional lung tissue that can be used to provide a more realistic environment for growth of functional airway organs ready for transplantation into humans and other animals. The lung tissue is generated over a given matrix, e.g., an artificial or decellularized lung tissue matrix. The present invention is further based on the use of this realistic environment for the preservation, repair, and modification of donor organs over prolonged periods of time in order to provide more, improved, and individualized grafts for transplantation.

As used herein, a "functional" lung tissue performs most or all of the functions of a normal healthy lung, e.g., allows for transportation of oxygen from the air into the bloodstream, and the release of carbon dioxide from the bloodstream into the air. It can humidify inhaled air, produce surfactant to decrease surface tension in the alveoli, and/or produce and transport mucus to remove inhaled particulate matter from the distal to the proximal airway.

As used herein, the terms "decellularized" and "acellular" are used or defined as the complete or near complete absence of detectable intracellular matter, endothelial cells, epithelial cells, and nuclei in histologic sections using standard histological staining procedures. Preferably, but not necessarily, residual cell debris also has been removed from the decellularized organ or tissue.

Decellularized Tissue/Organ Matrices

In some embodiments of the present methods, lung tissue is generated over a decellularized matrix. Methods and materials for a preparing a decellularized lung tissue matrix are known in the art, as discussed below. Any appropriate materials can be used to prepare such a matrix. In a preferred embodiment, a tissue matrix can be an acellular tissue scaffold developed from decellularized lung tissue. For example, tissue such as a human lung, e.g., one or a pair of human lungs or portions thereof, e.g., human, porcine, bovine, primate, or ovine cadaveric lungs or portions thereof, can be decellularized by an appropriate method to remove native cells from the tissue while maintaining morphological integrity and vasculature of the tissue or tissue portion and preserving extracellular matrix (ECM) proteins (see Tapias L F, and Ott H C. Decellularized scaffolds as a platform for bioengineered organs. *Current opinion in organ transplantation*. 2014; 19(2):145-52). Methods for decellularizing mammalian lung tissues are described, e.g., in O'Neill J D et al., Decellularization of human and porcine lung tissues for pulmonary tissue engineering. *Ann Thorac Surg*. 2013 September; 96(3):1046-55; Nichols J E et al., Production and assessment of decellularized pig and human lung scaffolds, *Tissue Eng Part A*. 2013 September; 19 (17-18):2045-62; Gilpin S E et al., Perfusion decellularization of human and porcine lungs: Bringing the matrix to clinical scale. *Journal of Heart and Lung Transplantation*. 2014; 33: 298-308; Song J J et al., Bioartificial lung engineering. *Am J Transplant*. 2012 February; 12(2):283-8; and Ott H C et al., Regeneration and orthotopic transplantation of a bioartificial lung. *Nat Med*. 2010 August; 16(8):927-33. Exemplary decellularization methods can include subjecting tissue (e.g., lung tissue) to repeated freeze-thaw cycles, for example using liquid nitrogen. In other cases, a tissue can be subjected to an anionic or ionic cellular disruption medium such as sodium dodecyl sulfate (SDS), polyethylene glycol (PEG), or TritonX. The tissue can also be treated with a nuclease solution (e.g., ribonuclease, deoxyribonuclease) and washed in sterile phosphate buffered saline with mild agitation. Exemplary methods are known in the art e.g., O'Neill J D et al., Decellularization of human and porcine lung tissues for pulmonary tissue engineering. *Ann Thorac Surg*. 2013 September; 96(3):1046-55. In some cases, decellularization can be performed by flushing the vessels, ducts, and/or cavities of the organ or tissue using methods and materials known in the art. For example, as described in Maghsoudlou et al., Preservation of micro-architecture and angiogenic potential in a pulmonary acellular matrix obtained using intermittent intra-tracheal flow of detergent enzymatic treatment. *Biomaterials*. 2013 September; 34(28):6638-48. Following the flushing step, the organ or tissue can be perfused via the line with a cellular disruption medium as described above for example 1% SDS in deionized water. Perfusion through the tissue can be anterograde or retrograde, and directionality can be alternated to improve perfusion efficiency. Depending upon the size and weight of an organ or tissue and the particular anionic or ionic detergent(s) and concentration of anionic or ionic detergent(s) in the cellular disruption medium, a tissue generally is perfused from about 2 to about 12 hours per gram of tissue with cellular disruption medium. Including washes, an organ may be perfused for up to about 12 to about 72 hours per gram of tissue. Perfusion generally is adjusted to physiologic conditions including flow rate and pressure, e.g., pressure between 5-100 mmHg, and flow rate between 0.1-10 times the physiologic cardiac output of the source organism or individual.

In another exemplary method, a decellularization method includes perfusing a detergent, e.g., (1) 0.1% SDS (2) 2%, sodium deoxycholate (SDC), or (3) 8 mmol/liter (3)3-[(3-cholamidopropyl)dimethylammonio]-1-propanesulfonate (CHAPS) (pH12) detergent, through the pulmonary artery at a constant pressure of 30 cm $H_2O$. The protocol for all 3 detergents includes:

1. a 10-minute initial antegrade wash with phosphate-buffered saline (PBS),
2. detergent perfusion for the time required to visualize an opaque translucent matrix (indicative of decellularization) plus an additional 20% of that initial time (e.g., 70 minutes+ 14 minutes),
3. 15-minute deionized $H_2O$ wash, and
4. an additional 172-hour PBS wash with added antibiotics and antimycotics.

This decellularization method, e.g., can include an additional wash of 1% Triton-X following the deionized $H_2O$. The SDC protocol can include a 0.1% Triton-X perfusion before SDC and a 1 mol/liter NaCl wash after SDC.

Similarly, porcine and human lung decellularization methods can include perfusion of a detergent or other decellularization agent though the pulmonary artery at constant pressure, followed by sequential washing with $H_2O$, 1% Triton-X solution, and PBS. Similar to rat lungs, decellularization can be deemed complete upon visual inspection and the appearance of an opaque translucent matrix. Variability in the starting organ, mainly due to extensiveness of pre-flushing during harvest and any resulting clots can contribute to the required length of perfusion. In general, the time of decellularization perfusion can vary e.g., from 4 to 7 days.

Decellularized tissue can consist essentially (e.g., at least: 85% pure, 90% pure, 92% pure, 95% pure, 96% pure, 97% pure, 98% pure, and 99% pure by weight) of the extracellular matrix (ECM) component of all or most regions of the tissue, including ECM components of the vascular tree. ECM components can include any or all of the following: fibronectin, fibrillin, laminin, elastin, members of the collagen family (e.g., collagen I, III, and IV), glycosaminoglycans, ground substance, reticular fibers and thrombospondin, which can remain organized as defined structures such as the basal lamina. In a preferred embodiment, decellularized lung tissue matrix retains an intact vasculature. Preserving a substantially intact vasculature enables connection of the tissue matrix to a subject's vascular system upon transplantation. In addition, a decellularized tissue matrix can be further treated with, for example, irradiation (e.g., UV, gamma) to reduce or eliminate the presence of any type of microorganism remaining on or in a decellularized tissue matrix.

Methods for obtaining decellularized tissue matrices using physical, chemical, and enzymatic means are known in the art, see, e.g., Liao et al, *Biomaterials* 29(8):1065-74 (2008); Gilbert et al., *Biomaterials* 27(9):3675-83 (2006); Teebken et al., *Eur. J. Vasc. Endovasc. Surg.* 19:381-86 (2000). See also U.S. Pat. Publication Nos. 2009/0142836; 2005/0256588; 2007/0244568; and 2003/0087428.

Artificial Organ Matrices

In some embodiments of the present methods, lung tissue is generated over an artificial organ matrix. Methods and materials for a preparing an artificial organ matrix are known in the art. Any appropriate materials can be used to prepare such a matrix. In a preferred embodiment, an artificial organ matrix can be a scaffold developed from porous materials such as, for example, polyglycolic acid, Pluronic F-127 (PF-127), Gelfoam sponge, collagen-glycosaminoglycan (GAG), fibrinogen-fibronectin-vitronectin hydrogel (FFVH), and elastin. See, e.g., Ingenito et al., *J Tissue Eng Regen Med.* 2009 Dec. 17; Hoganson et al., *Pediatric Research*, May 2008, 63(5):520-526; Chen et al., *Tissue Eng.* 2005 September-October; 11(9-10):1436-48. In some cases, an artificial organ matrix can have porous structures similar to alveolar units. See Andrade et al., *Am J Physiol Lung Cell Mol Physiol.* 2007 February; 292(2):L510-8. In some cases, an implanted artificial organ matrix can express organ-specific markers (e.g., lung-specific markers for Clara cells, pneumocytes, and respiratory epithelium). In some cases, an implanted artificial organ matrix can organize into identifiable structures (e.g., structures similar to alveoli and terminal bronchi in an artificial lung matrix). For example, an implanted artificial lung maxtrix made using FFVH can promote cell attachment, spreading and extracellular matrix expression in vitro and apparent engraftment in vivo, with evidence of trophic effects on the surrounding tissue. See Ingenito et al., supra. See also U.S. Pat. Nos. 7,662,409 and 6,087,552; United States Patent Publication Nos. 2010/0034791; 2009/0075282; 2009/0035855; 2008/0292677; 2008/0131473; 2007/0059293; 2005/0196423; 2003/0166274; 2003/0129751; 2002/0182261; 2002/0182241; and 2002/0172705.

Treatment with Tenascin-C and/or Fibrillin-2

The optimal scaffold for lung organ engineering would not only provide the necessary structure, but would additionally guide the organization and function of new lung tissue. The ECM is a complex entity that participates in many biological processes, including tissue development and repair (Balestrini and Niklason, Annals of biomedical engineering. 2015; 43(3):568-76). When considering the ECM in whole organ regeneration, the source of native lung tissue used to prepare the scaffold can have a direct impact on subsequent regeneration. Several studies have shown that underlying lung pathologies can cause changes in the ECM that are retained following decellularization, and can perpetuate during tissue repair (Burgess et al., The Journal of pathology. 2016; 240(4):397-409). This has been demonstrated for both pulmonary fibrosis and emphysema (Booth et al. American journal of respiratory and critical care medicine. 2012; 186(9):866-76; Sokocevic et al. Biomaterials. 2013; 34(13):3256-69). Age of the lung can also contribute important differences to the decellularized scaffold. It has been shown that growth on aged ECM can lead to significantly lower cellular expression of laminin $\alpha 3$ and $\alpha 4$ chains, which recapitulates the laminin deficiency that is observed in aged lung ECM. These data further highlight the deep biological information that is contained in the lung scaffold, and the feedback loops that can exist between reparative cell populations and the underlying protein matrix (Godin et al., PloS one. 2016; 11(3):e0150966).

Lung development actively continues following birth, and ECM remodeling is an essential component in the post-natal process of alveolarization. This mechanism functions to dramatically increase the gas exchange surface area, as the lung further refines the immature alveolar structure and undertakes secondary septation to generate a greater number of smaller sized alveoli (Whitsett et al., Physiological reviews. 1995; 75(4):749-57). The consequences of this process and the specific differences in ECM composition have not been well studied in the context of ex vivo tissue regeneration. Fetal wounds repair at a faster rate than adults, with little or no scarring (Yates et al., Birth defects research Part C, Embryo today: reviews. 2012; 96(4):325-33). Regrowth of lung is possible after lobectomy in infancy, with restoration of airway function and total recovery of lung volume (McBride et al., The Journal of clinical investigation. 1980; 66(5):962-70). Conversely, dysregulation of the ECM is an important driving factor for ageing, and age-related alterations in the ECM can be directly communicated to the surrounding cells, contributing to the development of chronic lung diseases such as emphysema and pulmonary fibrosis (Meiners et al., The European respiratory journal. 2015; 45(3):807-27). Another consequence of aging is the phenomenon of stem cell dysfunction and exhaustion, where the multipotent pool of progenitors progressively declines and becomes increasing senescent (Thannickal et al., American journal of respiratory and critical care medicine. 2015; 191(3):261-9). These interactions between the stem cell and the niche, including ECM, can contribute to this decrease in regenerative capacity.

The present study investigated the differences in ECM from neonatal lungs actively undergoing alveolarization, compared to adult lung donors, and evaluated the consequences of these differences on ex vivo lung epithelial repair. There was an increase in developmentally associated proteins Fibrillin-3 (FBN-3), Fibrillin-2 (FBN-2), and Tenascin-C (TN-C) in the neonatal human lung ECM, and report that supplementation of these two proteins both in vitro and in ex vivo lung regeneration on acellular lung scaffolds can enhance epithelial proliferation, decrease senescence, aid cell attachment and migration, and ultimately improve regenerated tissue morphology and structure.

In some embodiments, the lung tissue matrix, e.g., decellularized lung tissue matrix or artificial lung matrix, is pre-treated with a solution comprising Tenascin-C (e.g., 0.5-10 ug/ml, e.g., about 1-3 ug/ml) and/or Fibrillin-2 (e.g., whole or N and C fragments) (e.g., 0.5-10 ug/ml, e.g., about 1-3 ug/ml), e.g., in a 15 ml total volume for a rat lung matrix, prior to cell seeding. In these methods, the Tenascin-C and/or Fibrillin-2 are exogenous, i.e., are added to a solution in which the matrix is incubated (either before or during contact with the matrix), and are in addition to any Tenascin-C and/or Fibrillin-2 already present in the matrix (or already present in any serum present in the solution). In some embodiments, the methods include delivery of a solution comprising Tenascin-c and/or Fibrillin-2, e.g., about 0.5-10 ug/ml Tenascin-C and/or about 0.5-10 ug and/or Fibrillin-2, to the scaffold airways (e.g., by gravity pressure), e.g., and incubating the matrix in the presence of the Tenascin-C and/or Fibrillin-2, e.g., at 37° C. for about 1 hour. In some embodiments, the cells are seeded in a solution comprising Tenascin-C and/or Fibrillin-2. As an alternative to or in addition to Fibrillin-2, Fibrillin-3 can be used.

Exemplary sequences for human Tenascin-C precursor are in GenBank at NM_002160.3 (nucleic acid) and NP_002151.2 (protein). An exemplary protein sequence is as follows:

```
                                                           (SEQ ID NO: 1)
   1  mgamtqllag vflaflalat eggvlkkvir hkrqsgvnat lpeenqpvvf nhvyniklpv
  61  gsqcsvdles asgekdlapp sepsesfqeh tvdgenqivf thriniprra cgcaaapdvk
 121  ellsrleele nlvsslreqc tagagcclqp atgrldtrpf csgrgnfste gcgcvcepgw
 181  kgpncsepec pgnchlrgrc idgqcicddg ftgedcsqla cpsdcndqgk cvngvcicfe
 241  gyagadcsre icpvpcseeh gtcvdglcvc hdgfagddcn kplclnncyn rgrcvenecv
 301  cdegftgedc selicpndcf drgrcingtc yceegftged cgkptcphac htqgrceegq
 361  cvcdegfagv dcsekrcpad chnrgrcvdg rcecddgftg adcgelkcpn gcsghgrcvn
 421  gqcvcdegyt gedcsqlrcp ndchsrgrcv egkcvceggf kgydcsdmsc pndchqhgrc
 481  vngmcvcddg ytgedcrdrq cprdcsnrgl cvdgqcvced gftgpdcael scpndchgqg
 541  rcvngqcvch egfmgkdcke grcpsdchgq grcvdgqcic hegftgldcg qhscpsdcnn
 601  lgqcvsgrci cnegysgedc sevsppkdlv vtevteetvn lawdnemrvt eylvvytpth
 661  egglemqfry pgdqtstiiq elepgveyfi rvfailenkk sipvsarvat ylpapeglkf
 721  ksiketsvev ewdpldiafe tweiifrnmn kedegeitks lrrpetsyrq tglapgqeye
 781  islhivknnt rgpglkrvtt trldapsqie vkdvtdttal itwfkplaei dgieltygik
 841  dvpgdrttid ltedenqysi gnlkpdteye vslisrrgdm ssnpaketft tgldaprnlr
 901  rvsqtdnsit lewrngkaai dsyrikyapi sggdhaevdv pksqqattkt tltglrpgte
 961  ygigvsavke dkesnpatin aateldtpkd lqvsetaets ltllwktpla kfdryrinys
1021  lptgqwvgvq lprnttsyvl rglepgqeyn vlltaekgrh kskparvkas tegapelenl
1081  tvtevgwdgl rinwtaadqa yehfiiqvqe ankveaarnl tvpgslravd ipglkaatpy
1141  tvsiygviqg yrtpvlsaea stgetpnlge vvvaevgwda lklnwtapeg ayeyffiqvq
1201  eadtveaaqn ltvpgglrst dlpglkaath ytitirgvtq dfsttplsve vlteevpdmg
1261  nitvtevswd alrinwttpd gtydgftiqv qeadqveeah nitvpgslrs meipglragt
1321  pytvtlhgev rghstrplav evvtedlpql gdlaysevgw dglrinwtaa dnayehfviq
1381  vqevnkveaa qnitlpgslr avdipgleaa tpyrvsiygv irgyrtpvls aeastakepe
1441  ignlnvsdit pesfnlswma tdgifetfti eiidsnrlle tveynisgae rtahisglpp
1501  stdfivylsg lapsirtkti satattealp llenitisdi npygftvswm asenafdsfl
1561  vtvvdsgkll dpqeftlsgt qrklelrgli tgigyevmvs gftqghqtkp lraeivteae
1621  pevdnllvsd atpdgfrlsw tadegvfdnf vlkirdtkkg sepleitlla pertrditgl
1681  reateyeiel ygiskgrrsq tvsaiattam gspkevifsd itensatvsw raptaqvesf
1741  rityvpitgg tpsmvtvdgt ktqtrlvkli pgveylvsii amkgfeesep vsgsfttald
1801  gpsglvtani tdsealarwq paiatvdsyv isytgekvpe itrtvsgntv eyaltdlepa
1861  teytlrifae kgpqksstit akfttdldsp rdltatevqs etalltwrpp rasvtgyllv
1921  yesvdgtvke vivgpdttsy sladlspsth ytakigalng plrsnmigti fttigllypf
1981  pkdcsqamln gdttsglyti ylngdkaeal evfcdmtsdg ggwivflrrk ngrenfyqnw
2041  kayaagfgdr reefwlgldn lnkitaggqy elrvdlrdhg etafavydkf svgdaktryk
2101  lkvegysgta gdsmayhngr sfstfdkdtd saitncalsy kgafwyrnch rvnlmgrygd
2161  nnhsqgvnwf hwkghehsiq faemklrpsn frnlegrrkr a
```

As amino acids 1-22 appear to be a signal sequence, in some embodiments, the mature Tenascin-C protein can be used, e.g., amino acids 23-2201 of SEQ ID NO:1. Alternatively, a fragment comprising amino acids 23 to 625 can be used.

Exemplary sequences for the human fibrillin-2 precursor are in GenBank at NM_001999.3 (nucleic acid) and NP_001990.2 (protein). An exemplary protein sequence for human fibrillin-2 precursor is as follows:

(SEQ ID NO: 2)

```
   1  mgrrrrlclq lyflwlgcvv lwaggtaggp qppppkpprp qpppqqvrsa tagseggfla
  61  peyreegaav asrvrrrgqq dvlrgpnvcg srfhsyccpg wktlpggnqc ivpicrnscg
 121  dgfcsrpnmc tcssggisst cgsksiqqcs vrcmnggtca ddhcqcqkgy igtycgqpvc
 181  engcqnggrc igpnrcacvy gftgpqcerd yrtgpcftqv nnqmcqgqlt givctkticc
 241  atigrawghp cemcpaqpqp crrgfipnir tgacqdvdec gaipgicqgg ncintvgsfe
 301  crcpaghkgs ettqkcedid ecsiipgice tgecsntvgs yfcvcprgyv tstdgsrcid
 361  grtgmcfsgl vngrcagelp grmtkmgccc epgrcwgigt ipeacpvrgs eeyrrlcmdg
 421  lpmggipgsa gsrpggtggn gfapsgngng ygpggtgfip ipggngfspg vggagvgagg
 481  qgpiitglti lnqtidickh hanlclngrc iptvssyrce cnmgykqdan gdcidvdect
 541  snpctngdcv ntpgsyyckc hagfqrtptk qacidideci qngvlckngr cvntdgsfqc
 601  icnagfeltt dgkncvdhde ctttnmclng mcinedgsfk cickpgfvla pngryctdvd
 661  ecqtpgicmn ghcinsegsf rcdcppglav gmdgrvcvdt hmrstcyggi kkgvcvrpfp
 721  gavtkseccc anpdygfgep cqpcpaknsa efhglcssgv gitvdgrdin ecaldpdica
 781  ngicenlrgs yrcncnsgye pdasgrncid ideclvnrll cdnglcrntp gsysctcppg
 841  yvfrtetetc edinecesnp cvngacrnnl gsfncecspg sklsstglic idslkgtcwl
 901  niqdsrcevn ingatlksec catlgaawgs pcerceldta cprglarikg vtcedvnece
 961  vfpgvcpngr cvnskgsfhc ecpegltldg tgrvcldirm eqcylkwded ecihpvpgkf
1021  rmdacccavg aawgteceec pkpgtkeyet lcprgagfan rgdvltgrpf ykdineckaf
1081  pgmctygkcr ntigsfkcrc nsgfaldmee rnctdidecr ispdlcgsgi cvntpgsfec
1141  ecfegyesgf mmmkncmdid ecernpllcr ggtcvntegs fqcdcplghe lspsredcvd
1201  inecslsdnl crngkcvnmi gtyqcscnpg yqatpdrqgc tdidecmimn ggcdtqctns
1261  egsyecscse gyalmpdgrs cadidecenn pdicdggqct nipgeyrcic ydgfmasmdm
1321  ktcidvnecd lnsnicmfge centkgsfic hcglgysvkk gttgctdvde ceigahncdm
1381  hasclnipgs fkcscregwi gngikcidld ecsngthqcs inaqcvntpg syrcacsegf
1441  tgdgftcsdv decaeninlc enggclnvpg ayrcecemgf tpasdsrscq didecsfqni
1501  cvfgtcnnlp gmfhcicddg yeldrtggnc tdidecadpi ncvnglcvnt pgryecncpp
1561  dfqlnptgvg cvdnrvgncy lkfgprgdgs lscnteigvg vsrssccccsl gkawgnpcet
1621  cppvnsteyy ticpggegfr pnpitiiled idecgelpgl cqggncintf gsfqcecpqg
1681  yylsedtric edidecfahp gvcgpgtcyn tlgnytcicp peymqvnggh ncmdmrksfc
1741  yrsyngttce nelpfnvtkr mccctynvgk awnkpcepcp tpgtadfkti cgnipgftfd
1801  ihtgkavdid eckeipgica ngvcingigs frcecptgfs yndlllvced idecsngdnl
1861  cqrnadcins pgsyrcecaa gfklspngac vdrnecleip nvcshglcvd lqgsyqcich
1921  ngfkasqdqt mcmdvdecer hpcgngtckn tvgsyncicy pgfelthnnd cldidecssf
1981  fgqvcrngrc fneigsfkcl cnegyeltpd gkncidtnec valpgscspg tcqnlegsfr
2041  cicppgyevk sencidinec dedpniclfg sctntpggfq cicppgfvls dngrrcfdtr
2101  gsfcftnfen gkcsvpkafn ttkakcccsk mpgegwgdpc elcpkddeva fqdlcpyghg
2161  tvpslhdtre dvneclespg icsngqcint dgsfrcecpm gynldytgvr cvdtdecsig
```

```
-continued
2221   npcgngtctn  vigsfecncn  egfepgpmmn  cedinecaqn  pllcafrcmn  tfgsyectcp 2281   igyalredqk  mckdldecae  glhdcesrgm  mcknligtfm  cicppgmarr  pdgegcvden 2341   ecrtkpgice  ngrcvniigs  yrcecnegfq  ssssgtecld  nrqglcfaev  lgticgmass 2401   srnlvtksec  ccdggrgwgh  qcelcplpgt  aqykkicphg  pgyttdgrdi  deckvmpnlc 2461   tngqcintmg  sfrcfckvgy  ttdisgtsci  dldecsqspk  pcnyicknte  gsyqcscprg 2521   yvlqedgktc  kdldecqtkq  hncqflcvnt  lggftckcpp  gftqhhtaci  dnnecgsgps 2581   lcgakgicqn  tpgsfscecq  rgfsldatgl  ncedvdecdg  nhrcqhgcqn  ilggyrcgcp 2641   ggyighyqwn  qcvdenecsn  pnacgsascy  ntlgsykcac  psgfsfdqfs  sachdvnecs 2701   ssknpcnygc  snteggylcg  cppgyyrvgq  ghcvsgmgfn  kgqylsldte  vdeenalspe 2761   acyeckingy  skkdsrqkrs  ihepdptave  qislesvdmd  spvnmkfnls  hlgskehile 2821   lrpaigpinn  hiryvisqgn  ddsvfrihqr  nglsylhtak  kklmpgtytl  eitsiplykk 2881   kelkkleesn  eddyllgelg  ealrmrlqiq  ly
```

As amino acids 1-28 appear to be a signal sequence, in some embodiments, the mature Fibrillin-2 protein can be used, e.g., amino acids 29-2912 of SEQ ID NO:2. In some embodiments, the Fibrillin-2 is made as two separate peptides, e.g., N and C fragments, e.g., an N-terminal half rFBN2-N (amino acids 1-1732) and a C-terminal half rFBN2-C (amino acids 1531-2771), e.g., produced in human 293 cells. See, e.g., Lin et al., J. Biol. Chem. 277: 50795-50804 (2002).

Exemplary sequences for the human fibrillin-3 precursor are in GenBank at NM_001321431.1 (nucleic acid) and NP_001308360.1 (protein), or NM_032447.4 (nucleic acid) and NP_115823.3 (amino acid).

Preferably the sequence of the protein used is at least 80% identical (e.g., at least 90%, 95%, or 99% identical) to the mature reference sequence provided above, and has an activity described herein. To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 80% of the length of the reference sequence, and in some embodiments is at least 90% or 100%. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. For example, the percent identity between two amino acid sequences can determined using the Needleman and Wunsch ((1970) J. Mol. Biol. 48:444-453) algorithm that has been incorporated into the GAP program in the GCG software package (available on the world wide web at gcg.com), using the default parameters, e.g., a Blossum 62 scoring matrix with a gap penalty of 12, a gap extend penalty of 4, and a frameshift gap penalty of 5.

Any form of TNC or FBN-2 can be used, e.g., protein produced recombinantly (e.g., expressed and isolated from cells, e.g., prokaryotic or eukaryotic, preferably mammalian (more preferably human) cells, or from a transgenic animal producing the protein, or transcribe and translated in a cell free system in vitro) or protein isolated from natural sources. Although human proteins are preferred, other mammalian species can also be used, e.g., bovine, caprine, porcine, equine, or ovine.

Although the present disclosure exemplifies the use of TNC and/or FBN-2 with some cell types, others can also be used.

Cell Seeding

In some of the methods described herein, a lung tissue matrix, e.g., decellularized lung tissue matrix or artificial lung matrix, is seeded with cells, e.g., differentiated or regenerative cells.

Any appropriate regenerative cell type, such as naïve or undifferentiated cell types, can be used to seed the lung tissue matrix. The cells may be seeded at a variety of stages including, but not limited to, stem cell stage (e.g., after induction), progenitor cell stage, hemangioblast stage, or differentiated stage (e.g., CD 31+, vWF+). As used herein, regenerative cells can include, without limitation, progenitor cells, precursor cells, and "adult"-derived stem cells including umbilical cord cells (e.g., human umbilical vein endothelial cells) and fetal stem cells. Regenerative cells also can include differentiated or committed cell types. Stem cells appropriate for the methods and materials provided herein can include human induced pluripotent stem cells (iPSC) (e.g., undifferentiated, differentiated endoderm, anteriolized endoderm, TTF-1 positive lung progenitors), human mesenchymal stem cells, human umbilical vein endothelial cells, multipotent adult progenitor cells (MAPC), iPS derived mesenchymal cells, or embryonic stem cells. In some cases, regenerative cells derived from other tissues also can be used. For example, regenerative cells derived from skin, bone, muscle, bone marrow, synovium, or adipose tissue can be used to develop stem cell-seeded tissue matrices.

In some cases, a lung tissue matrix provided herein can be alternatively or further seeded with differentiated cell types such as (preferably human) epithelial cells and endothelial cells. For example, a lung matrix can be seeded with endothelial cells via the vasculature (e.g. through the arterial line or the venous line), and seeded with the proliferative basal stem cells from a human donor wherein the cells are Krt5+p63+ cells, via the airway (e.g., through the tracheal line). The lung matrix can also be seeded with one or more cell types (e.g., one or more of types of epithelial and mesenchymal cells, adult peripheral blood derived epithelial cells, cord blood-derived epithelial cells, iPS derived epithelial cells, progenitor stage cells (e.g., smooth muscle), adult lung derived cell mixture (e.g., rat human), commercially available small airway epithelial cells or alveolar epithelial cells, Embryonic Stem (ES) cell-derived epithelial cells, and/or human umbilical vein endothelial cells (HU-VEC).

Any type of appropriate commercially available media and/or media kits may be used for the seeding and culture of cells. For example, SAGM media may be used for small airway cells (e.g., SAGM BulletKit by Lonza) and EGM-2 kits may be used for endothelial cells (e.g., EGM-2 BulletKit by Lonza). Media customized to the seeded endothelial cell type may be used (e.g., by increasing or decreasing growth factors such as VEGF) as described in, for example, Brudno Y et al. *Biomaterials* 34 (2013) 9201-9209. In the case of endothelial cells, a sequence of different media compositions may be used to induce different phases of seeding, expansion, engraftment, and maturation of cells. For example, in a first phase, a cell seeded constructs may be perfused with an 'angiogenic media' for 2-30 days to increase endothelial cell expansion, migration, and metabolism. This media is characterized by high concentration of cytokines, e.g., VEGF at 5-100 ng/ml and bFGF at 5-100 ng/ml, and the presence of phorbol myristate acetate (PMA), e.g., 5-100 ng/ml PMA, which activates the angiogenic pathway through activation of protein kinase C, and Ang-1, which stimulates endothelial cell sprouting. In a second phase, a cell seeded construct can then be perfused with 'tightening media' that supports endothelial maturation and the formation of tight junctions. Tightening media has lower levels of cytokines, with the same basic composition as the angiogenic media but with decreased levels of VEGF, bFGF and PMA (0.1-5 ng/ml VEGF, FGF, and PMA). Hydrocortisone, which promotes tight junction formation and has been shown to reduce pulmonary edema, can be further added to the tightening media to promote vascular maturation. Further promaturation factors such as PDGF and Ang-2 may be added to the tightening media to enhance vessel formation. Concentrations of these factors may be titrated to support different vessel sizes. Media changes can be performed gradually to avoid detrimental effects of sudden cytokine changes. Similar to endothelial cell supporting media, sequential media changes can be used to guide epithelial cell fate. Initial media may contain, for example, Activin A at 10-200 ng/ml and Pi3K inhibitors such as ZSTK 474 at 0.01-1 uM to induce definite endoderm, subsequently TGF-beta inhibitors such as A-8301 at 01-10 uM and BMP4 antagonists such as DMH-1 at 0.05-1 uM to induce anteriorized endoderm, and finally BMP4 at 1-100 ug/ml, FGF2 at 10-500 ng/ml, GSK-3beta inhibitor such as CHIR 99021 at 10-500 nM, a PI3K inhibitor such as PIK-75 at 1-100 nM and methotrexate at 1-100 nM to induce the generation of lung progenitor cells.

Any appropriate method for isolating and collecting cells for seeding can be used. For example, induced pluripotent stem cells generally can be obtained from somatic cells "reprogrammed" to a pluripotent state by the ectopic expression of transcription factors such as Oct4, Sox2, Klf4, c-MYC, Nanog, and Lin28. See Takahashi et al., *Cell* 131:861-72 (2007); Park et al., *Nature* 451:141-146 (2008); Yu et al., *Science* 318:1917-20 (2007); Zhu et al., *Cell Stem Cell.* 7:651-5 2010; and Li et al., *Cell Res.* 21:196-204 (2011); Malik and Rao, Methods Mol Biol. 2013; 997:23-33; Okano et al., Circ Res. 2013 Feb. 1; 112(3):523-33; Lin and Ying, Methods Mol Biol. 2013; 936:295-312. Peripheral blood-derived mononuclear cells can be isolated from patient blood samples and used to generate induced pluripotent stem cells. In other examples, induced pluripotent stem cells can be obtained by reprogramming with constructs optimized for high co-expression of Oct4, Sox2, Klf4, c-MYC in conjunction with small molecule such as transforming growth factor β (SB431542), MEK/ERK (PD0325901) and Rho-kinase signaling (Thiazovivin). See Groβ et al., *Curr Mol Med.* 13:765-76 (2013) and Hou et al., *Science* 341:651:654 (2013). Methods for generating endothelial cells from stem cells are reviewed in Reed et al., Br J Clin Pharmacol. 2013 April; 75(4):897-906. Cord blood stem cells can be isolated from fresh or frozen umbilical cord blood. Mesenchymal stem cells can be isolated from, for example, raw unpurified bone marrow or ficoll-purified bone marrow. Epithelial and endothelial cells can be isolated and collected from living or cadaveric donors, e.g., from the subject who will be receiving the bioartificial lung, according to methods known in the art. For example, epithelial cells can be obtained from a skin tissue sample (e.g., a punch biopsy), and endothelial cells can be obtained from a vascular tissue sample.

In some embodiments, proteolytic enzymes are perfused into the tissue sample through a catheter placed in the vasculature. Portions of the enzymatically treated tissue can be subjected to further enzymatic and mechanical disruption. The mixture of cells obtained in this manner can be separated to purify epithelial and endothelial cells. In some cases, flow cytometry-based methods (e.g., fluorescence-activated cell sorting) can be used to sort cells based on the presence or absence of specific cell surface markers. Furthermore, lung cells (epithelial, mesenchymal, and endothelial) can be obtained from lung biopsies, which can be obtained via transbronchial and endobronchial biopsies or via surgical biopsies of lung tissue. In cases where non-autologous cells are used, the selection of immune type-matched cells should be considered, so that the organ or tissue will not be rejected when implanted into a subject.

Isolated cells can be rinsed in a buffered solution (e.g., phosphate buffered saline at pH 7.4) and resuspended in a cell culture medium. Standard cell culture methods can be used to culture and expand the population of cells. Once obtained, the cells can be used to seed the tissue matrix, e.g., introduced into the matrix via the arterial or venous lines (endothelial cells) or through the airway (tracheal) line (epithelial cells). For example, a tissue matrix can be seeded with at least one cell type in vitro at any appropriate cell density. For example, cell densities for seeding a matrix can be at least $1 \times 10^3$ cells/gram matrix. Cell densities can range between about $1 \times 10^5$ to about $1 \times 10^{10}$ cells/gram matrix (e.g., at least 100,000, 1,000,000, 10,000,000, 100,000,000, 1,000,000,000, or 10,000,000,000 cells/gram matrix) can be used.

In some cases, a decellularized or artificial lung tissue matrix, as provided herein, can be seeded with the cell types and cell densities described above, e.g., by gravity flow or perfusion seeding. For example, a flow perfusion system can be used to seed the decellularized lung tissue matrix via the vascular system preserved in the tissue matrix (e.g., through the arterial line). In some cases, automated flow perfusion systems can be used under the appropriate conditions. Such perfusion seeding methods can improve seeding efficiencies and provide more uniform distribution of cells throughout the composition. Quantitative biochemical and image analysis techniques can be used to assess the distribution of seeded cells following either static or perfusion seeding methods.

In some cases, a tissue matrix can be impregnated or perfused with one or more growth factors to stimulate differentiation of the seeded regenerative cells. For example, a tissue matrix can be impregnated or perfused with growth factors appropriate for the methods and materials provided herein, for example, vascular endothelial growth factor (VEGF), TGF-β growth factors, bone morphogenetic proteins (e.g., BMP-1, BMP-4), platelet-derived growth factor (PDGF), basic fibroblast growth factor (b-FGF), e.g., FGF-10, insulin-like growth factor (IGF), epidermal growth factor (EGF), or growth differentiation factor-5 (GDF-5). See, e.g., Desai and Cardoso, Respire. Res. 3:2 (2002). These growth factors can be encapsulated to control temporal release. Different parts of the scaffold can be enhanced with different growth factors to add spatial control of growth factor stimulation. In the present methods, the cells seeding the airway can be perfused with a notch inhibitor, e.g., a gamma secretase inhibitor.

Seeded tissue matrices can be incubated for a period of time (e.g., from several hours to about 14 days or more) post-seeding to improve adhesion and penetration of the cells in the tissue matrix. The seeded tissue matrix can be maintained under conditions in which at least some of the regenerative cells can multiply and/or differentiate within and on the acellular tissue matrix. Such conditions can include, without limitation, the appropriate temperature (35-38 degree centigrade) and/or pressure (e.g., atmospheric), electrical and/or mechanical activity (e.g., ventilation via positive or negative pressure with positive end expiratory pressure from 1-20 cmH2O, mean airway pressure from 5-50 cmH2O, and peak inspiratory pressure from 5-65 cmH2O), the appropriate gases, e.g., O2 (1-100% FiO2) and/or $CO_2$ (0-10% FiCO2), an appropriate amount of humidity (10-100%), and sterile or near-sterile conditions. Such conditions can also include wet ventilation, wet to dry ventilation and dry ventilation. In some cases, nutritional supplements (e.g., nutrients and/or a carbon source such as glucose), exogenous hormones, or growth factors can be added to the seeded tissue matrix. In preferred embodiments, a notch inhibitor, e.g., a gamma secretase inhibitor, is added to the cells seeded through the airway. Histology and cell staining can be performed to assay for seeded cell retention and propagation. Any appropriate method can be performed to assay for seeded cell differentiation. In general, the methods described herein will be performed in an airway organ bioreactor apparatus, e.g., as described herein.

Thus, the methods described herein can be used to generate a transplantable bioartificial lung tissue, e.g., for transplanting into a human subject. As described herein, a transplantable tissue will preferably retain a sufficiently intact vasculature that can be connected to the patient's vascular system.

The bioartificial lung tissues described herein can be combined with packaging material to generate articles of manufacture or kits. Components and methods for producing articles of manufacture are well known. In addition to the bioartificial tissues, an article of manufacture or kit can further can include, for example, one or more anti-adhesives, sterile water, pharmaceutical carriers, buffers, and/or other reagents for promoting the development of functional lung tissue in vitro and/or following transplantation. In addition, printed instructions describing how the composition contained therein can be used can be included in such articles of manufacture. The components in an article of manufacture or kit can be packaged in a variety of suitable containers.

Notch/Gamma-Secretase Inhibitors

Gamma secretase inhibitors useful in the present methods include, e.g., RO4929097; DAPT (N-[(3,5-Difluorophenyl) acetyl]-L-alanyl-2-phenyl]glycine-1,1-dimethylethyl ester); L-685458 ((5S)-(t-Butoxycarbonylamino)-6-phenyl-(4R) hydroxy-(2R)benzylhexanoyl)-L-leu-L-phe-amide); BMS-708163 (Avagacestat); BMS-299897 (2-[(1R)-1-[[(4-Chlorophenyl)sulfonyl](2,5-difluorophenyl)amino]ethyl-5-fluorobenzenebutanoic acid); MK-0752; YO-01027; MDL28170 (Sigma); LY411575 (N-2((2S)-2-(3,5-difluorophenyl)-2-hydroxyethanoyl)-N1-((7S)-5-methyl-6-oxo-6,7-dihydro-5H-dibenzo[b,d]azepin-7-yl)-1-alaninamide, see U.S. Pat. No. 6,541,466); ELN-46719 (2-hydroxy-valeric acid amide analog of LY411575 (where LY411575 is the 3,5-difluoro-mandelic acid amide) (U.S. Pat. No. 6,541, 466)); PF-03084014 ((S)-2-((S)-5,7-difluoro-1,2,3,4-tetrahydronaphthalen-3-ylamino)-N-(1-(2-methyl-1-(neopentylamino)propan-2-yl)-1H-imidazol-4-yl)pentanamide, Samon et al., Mol Cancer Ther 2012; 11:1565-1575); and Compound E ((2S)-2-{[(3,5-Difluorophenyl)acetyl]amino}-N-[(3S)-1-methyl-2-oxo-5-phenyl-2,3-dihydro-1H-1,4-benzodiazepin-3-yl]propanamide; see WO 98/28268 and Samon et al., Mol Cancer Ther 2012; 11:1565-1575; available from Alexis Biochemicals)), or pharmaceutically acceptable salts thereof.

In some embodiments, suitable gamma secretase inhibitors include: semagacestat (also known as LY450139, (2S)-2-hydroxy-3-methyl-N-[(1S)-1-methyl-2-oxo-2-[[(1S)-2,3, 4,5-tetrahydro-3-methyl-2-oxo-1H-3-benzazepin-1-yl] amino]ethyl]butanamide, available from Eli Lilly; WO 02/47671 and U.S. Pat. No. 7,468,365); LY411575 (N-2 ((2S)-2-(3,5-difluorophenyl)-2-hydroxyethanoyl)-N1-((7S)-5-methyl-6-oxo-6,7-dihydro-5H-dibenzo[b,d]azepin-7-yl)-L-alaninamide, available from Eli Lilly, Fauq et al., Bioorg Med Chem Lett 17: 6392-5, 2007); begacestat (also known as GSI-953, U.S. Pat. No. 7,300,951); arylsulfonamides (A S, Fuwa et al., Bioorg Med Chem Lett. 16(16):4184-4189, 2006); N—[N-(3,5-difluorophenacetyl)-L-alanyl]-(S)-phenylglycine t-butyl ester (DAPT, Shih and Wang, Cancer Res. 67: 1879-1882, 2007); N—[N-3,5-Difluorophenacetyl]-L-alanyl-S-phenylglycine Methyl Ester (also known as DAPM, gamma-Secretase Inhibitor XVI, available from EMD Millipore); Compound W (3,5-bis(4-Nitrophenoxy) benzoic acid, available from Tocris Bioscience); L-685,458 ((5S)-(tert-Butoxycarbonylamino)-6-phenyl-(4R)-hydroxy-(2R)-benzylhexanoyl)-L-leucy-L-phenylalaninamide, available from Sigma-Aldrich, Shearmen et al., Biochemistry 39, 8698-8704, 2000); BMS-289948 (4-chloro-N-(2,5-difluorophenyl)-N-((1R)-{4-fluoro-2-[3-(1H-imidazol-1-yl)propyl] phenyl}ethyl)benzenesulfonamide hydrochloride, available from Bristol Myers Squibb); BMS-299897 (4-[2-((1R)-1-{[(4-chlorophenyl)sulfonyl]-2,5-difluoroanilino}ethyl)-5-fluorophenyl]butanoic acid, available from Bristol Myers Squibb, see Zheng et al., Xenobiotica 39(7):544-55, 2009); avagacestat (also known as BMS-708163, (R)-2-(4-chloro-N-(2-fluoro-4-(1,2,4-oxadiazol-3-yl)benzyl)phenylsulfonamido)-5,5,5-trifluoropentanamide, available from Bristol Myers Squibb, Albright et al., J Pharmacol. Exp. Ther. 344(3):686-695, 2013); MK-0752 (3-(4-((4-chlorophenyl) sulfonyl)-4-(2,5-difluorophenyl)cyclohexyl)propanoic acid, available from Merck); MRK-003 ((3'R,6R,9R)-5'-(2,2,2-trifluoroethyl)-2-((E)-3-(4-(trifluoromethyl)piperidin-1-yl)

prop-1-en-1-yl)-5,6,7,8,9,10-hexahydrospiro[6,9-methano-benzo[8]annulene-11,3'-[1,2,5]thiadiazolidine] 1',1'-dioxide, available from Merck, Mizuma et al., Mol Cancer Ther. 11(9):1999-2009, 2012); MRK-560 (N-[cis-4-[(4-Chlorophenyl)sulfonyl]-4-(2,5-difluorophenyl)cyclohexyl]-1,1,1-trifluoro-methanesulfonamide, Best et. al., J Pharmacol Exp Ther. 317(2):786-90, 2006); RO-4929097 (also known as R4733, (S)-2,2-dimethyl-N1-(6-oxo-6,7-dihydro-5H-dibenzo[b,d]azepin-7-yl)-N3-(2,2,3,3,3-pentafluoropropyl)malonamide, available from Hoffman-La Roche Inc., Tolcher et al., J Clin. Oncol. 30(19):2348-2353, 2012); JLK6 (also known as 7-Amino-4-chloro-3-methoxyisocoumarin, available from Santa Cruz Biotechnology, Inc., Petit et al., Nat. Cell. Biol. 3: 507-511, 2001); Tarenflurbil (also known as (R)-Flurbiprofen, (2R)-2-(3-fluoro-4-phenylphenyl)propanoic acid); ALX-260-127 (also known as Compound 11, described by Wolfe et al., J. Med. Chem. 41: 6, 1998); Sulindac sulfide (SSide, Takahashi et al., J Biol Chem. 278(20): 18664-70, 2003); 1,1,1-trifluoro-N-(4-[5-fluoro-2-(trifluoromethyl)phenyl]-4-{[4 (trifluoromethyl)phenyl] sulfonyl}cyclohexyl)methanesulfonamide (described in US20110275719); N-[trans-3-[(4-chlorophenyl)sulfonyl]-3-(2,5-difluorophenyl)cyclobutyl]-1,1,1-trifluoromethanesulfonamide (described in US20110263580); N-[cis-3-[(4-chlorophenyl)sulfonyl]-3-(2,5-difluorophenyl)cyclobutyl]-1,1,1-trifluoromethanesulfonamide (described in US2011-0263580); N-[cis-3-[(4-chlorophenyl)sulfonyl]-3-(2-cyano-5-fluorophenyl)cyclobutyl]-1,1,1-trifluoromethanesulfonamide (described in US20110263580); N-[cis-3-[(4-chlorophenyl)sulfonyl]-3-(2,5-dichlorophenyl)cyclobutyl]-1,1,1-trifluoromethanesulfonamide (described in US2011-0263580); N-(cis-3-(2,5-difluorophenyl)-3-{[4-(trifluoromethyl)phenyl]sulfonyl}cyclobutyl)-1,1,1-trifluoromethanesulfonarnide (described in US20110263580); N-{cis-3-(5-chloro-2-fluorophenyl)-3-[(4-chlorophenyl)sulfonyl]cyclobutyl}-1,1,1-trifluoromethanesulfonamide (described in US20110263580); N-{cis-3-(2, 5-difluorophenyl)-3-[(4-fluorophenyl)sulfonyl]cyclobutyl}-1,1,1-trifluoromethanesulfonamide (described in US20110263580); N-{cis-3-(2,5-difluorophenyl)-3-[(3,4-difluorophenyl)sulfonyl]cyclobutyl}-1,1,1-trifluoromethanesulfonamide (described in US20110263580); N-[cis-3-[(4-cyanophenyl)sulfonyl]-3-(2,5-difluorophenyl)cyclobutyl]-1,1,1-trifluoromethanesulfonamide (described in US20110263580); 4-{[cis-3-[(4-chlorophenyl)sulfonyl]-3-(2,5-difluorophenyl)cyclobutyl] [trifluoromethyl) sulfonyl]amino}butanoic acid (described in US20110263580); N-[cis-3-[(4-chlorophenyl)sulfonyl]-3-(2,5-difluorophenyl)cyclobutyl]-1,1,1-trifluoro-N-[2-(tetrahydro-2-pyran-2-yloxy)ethyl]methanesulfonamide (described in US20110263580); Methyl{[cis-3-[(4-chlorophenyl)sulfonyl]-3-(2,5-difluorophenyl)cyclobutyl][(trifluoromethyl)sulfonyl]amino}acetate (described in US2011-0263580); N-[3-[(4-chlorophenyl)sulfonyl]-3-(2,5-difluorophenyl)cyclobutyl]-1,1,1-trifluoro-N-methylmethanesulfonamide (described in US20110263580); N-[3-[(4-chlorophenyl)sulfonyl]-3-(2,5-difluorophenyl)cyclobutyl]-1,1,1-trifluoro-N-methylmethanesulfonamide (described in US20110263580); Methyl 4-{[cis-3-[(4-chlorophenyl)sulfonyl]-3-(2,5-difluorophenyl)cyclobutyl] [(trifluoro-methyl) sulfonyl]amino}butanoate (described in US20110263580); N-[cis-3-[(4-chlorophenyl)sulfonyl]-3-(2,5-difluorophenyl) cyclobutyl]-N-[(trifluoromethyl)sulfonyl]glycine (described in US20110263580); N-[cis-3-[(4-chlorophenyl)sulfonyl]-3-(2,5-difluorophenyl)-1-methylcyclobutyl]-1,1,1-trifluoromethanesulfonamide (described in US20110263580); N-(cis-3-(2,5-difluorophenyl)-1-methyl-3-{[4-(trifluoromethyl)phenyl]sulfonyl}cyclobutyl)-1,1,1-trifluoromethanesulfonamide (described in US20110263580); N-[cis-3-[(4-chlorophenyl)sulfonyl]-3-(2,5-difluorophenyl)cyclobutyl]-1,1,1-trifluoro-N-[(trifluoromethyl)sulfonyl]methanesulfonamide (described in US20110263580); Sodium[cis-3-[(4-chlorophenyl)sulfonyl]-3-(2,5-difluorophenyl)cyclobutyl] [(trifluoromethyl)sulfonyl]azanide (described in US20110-263580); Potassium[cis-3-[(4-chlorophenyl)sulfonyl]-3-(2, 5-difluorophenyl)cyclo butyl] [(trifluoromethyl)sulfonyl] azanide (described in US20110263580); N-[cis-3-[(4-trifluoromethoxyphenyl)sulfonyl]-3-(2,5-difluorophenyl)cyclobutyl]-1,1,1-trifluoromethanesulfonamide (described in US20110263580); 1,1,1-trifluoro-N-(4-[5-fluoro-2-(trifluoromethyl)phenyl]-4-{[4-(trifluoromethyl)phenyl]sulfonyl}-cyclohexyl)methanesulfonamide (described in US2011-0263580); gamma-Secretase Inhibitor I (also known as Z-Leu-Leu-Nle-CHO, benzyloxycarbonyl-leucyl-leucyl-norleucinal, available from Calbiochem); gamma-secretase inhibitor II:

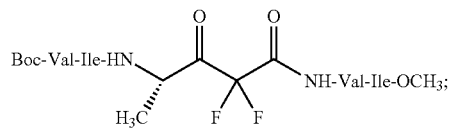

(MOL)(CDX) (available from Calbiochem); gamma secretase inhibitor III, (N-Benzyloxycarbonyl-Leu-leucinal, available from Calbiochem); gamma secretase inhibitor IV, (N-(2-Naphthoyl)-Val-phenylalaninal, available from Calbiochem); gamma-secretase inhibitor V (also known as Z-LF-CHO, N-Benzyloxycarbonyl-Leu-phenylalaninal, available from EMD Millipore); gamma-secretase inhibitor VI (1-(S)-endo-N-(1,3,3)-Trimethylbicyclo[2.2.1]hept-2-yl)-4-fluorophenyl Sulfonamide, available from EMD Millipore); gamma secretase inhibitor VII, (also known as Compound A, MOC-LL-CHO, Menthyloxycarbonyl-LL-CHO, available from Calbiochem); gamma secretase inhibitor X, ({1S-Benzyl-4R-[1-(1S-carbamoyl-2-phenethylcarbamoyl)-1S-3-methylbutylcarbamoyl]-2R-hydroxy-5-phenylpentyl}carbamic acid tert-butyl ester, available from Calbiochem); gamma secretase inhibitor XI, (7-Amino-4-chloro-3-methoxyisocoumarin, available from Calbiochem); gamma secretase inhibitor XII, (also known as Z-Ile-Leu-CHO, Shih and Wang, Cancer Res. 67: 1879-1882, 2007); gamma secretase inhibitor XIII, (Z-Tyr-Ile-Leu-CHO, available from Calbiochem); gamma secretase inhibitor XIV, (Z-Cys(t-Bu)-Ile-Leu-CHO, available from Calbiochem); gamma secretase inhibitor XVII, (also known as WPE-III-31C),

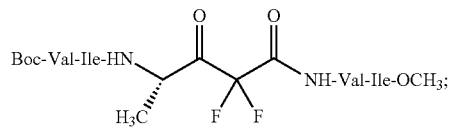

(MOL)(CDX) (available from Calbiochem); gamma secretase inhibitor XIX, (also known as benzodiazepine, (2S,3R)-3-(3,4-Difluorophenyl)-2-(4-fluorophenyl)-4-hydroxy-N-((3S)-2-oxo-5-phenyl-2,3-dihydro-1H-benzo[e][1,4]diazepin-3-yl)-butyramide, Churcher et al., J Med Chem. 46(12): 2275-8, 2003); gamma secretase inhibitor XX, (also known as dibenzazepine, (S,S)-2-[2-(3,5-Difluorophenyl)acetylamino]-N-(5-methyl-6-oxo-6,7-dihydro-5H-dibenzo[b,d] azepin-7-yl)propionamide,

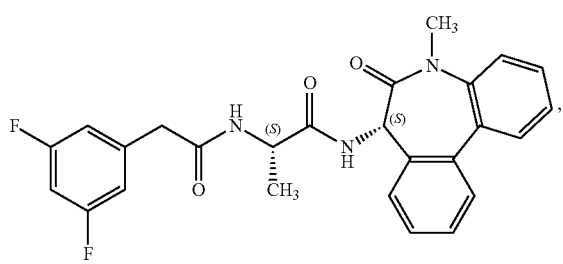

(MOL)(CDX) (Weihofen et al., Science 296: 2215-2218, 2002, available from Calbiochem); gamma secretase inhibitor XXI, ((S,S)-2-[2-(3,5-Difluorophenyl)-acetylamino]-N-(1-methyl-2-oxo-5-phenyl-2,3-dihydro-1H-benzo[e][1,4]diazepin-3-yl)-propionamide, available from Calbiochem); 5-methyl-2-propan-2-ylcyclohexyl)N-[4-methyl-1-[(4-methyl-1-oxopentan-2-yl)amino]-1-oxopentan-2-yl]carbamate (available from HDH Pharma Inc.); N-trans-3,5-Dimethoxycinnamoyl-Ile-leucinal (available from Calbiochem); N-tert-Butyloxycarbonyl-Gly-Val-Valinal; isovaleryl-V V-Sta-A-Sta-OCH3 (available from Calbiochem); diethyl-(5-phenyl-3H-azepin-2-yl)-amine (described in U.S. Pat. No. 8,188,069); diethyl-(5-isopropyl-3H-azepin-2-yl)-amine (described in U.S. Pat. No. 8,188,069); diethyl-(4-phenyl-3H-azepin-2-yl)-amine (described in U.S. Pat. No. 8,188,069); diethyl-(6-phenyl-3H-azepin-2-yl)-amine (described in U.S. Pat. No. 8,188,069); 5-phenyl-1,3-dihydro-azepin-2-one (described in U.S. Pat. No. 8,188,069); 5-Isopropyl-1,3-dihydro-azepin-2-one (described in U.S. Pat. No. 8,188,069); 4-phenyl-1,3-dihydro-azepin-2-one (described in U.S. Pat. No. 8,188,069); 6-phenyl-1,3-dihydro-azepin-2-one (described in U.S. Pat. No. 8,188,069); 2-butoxy-5-phenyl-3H-azepine (described in U.S. Pat. No. 8,188,069); 1-methyl-5-phenyl-1,3-dihydro-azepin-2-one (described in U.S. Pat. No. 8,188,069); 5-isopropyl-1-methyl-1,3-dihydro-azepin-2-one (described in U.S. Pat. No. 8,188,069); 1-methyl-4-phenyl-1,3-dihydro-azepin-2-one (described in U.S. Pat. No. 8,188,069); 1-methyl-6-phenyl-1,3-dihydro-azepin-2-one (described in U.S. Pat. No. 8,188,069); 1-methyl-5-phenyl-1H-azepine-2,3-dione-3-oxime (described in U.S. Pat. No. 8,188,069); 5-isopropyl-1-methyl-1H-azepine-2,3-dione-3-oxime (described in U.S. Pat. No. 8,188,069); 1-methyl-6-phenyl-1H-azepine-2,3-dione-3-oxime (described in U.S. Pat. No. 8,188,069); 1-methyl-4-phenyl-1H-azepine-2,3-dione-3-oxime (described in U.S. Pat. No. 8,188,069); 3-amino-1-methyl-5-phenyl-1,3-dihydro-azepin-2-one (described in U.S. Pat. No. 8,188,069); 3-amino-5-isopropyl-1-methyl-1,3-dihydro-azepin-2-one (described in U.S. Pat. No. 8,188,069); 3-amino-1-methyl-4-phenyl-1,3-dihydro-azepin-2-one (described in U.S. Pat. No. 8,188,069); 3-amino-1-methyl-6-phenyl-1,3-dihydro-azepin-2-one (described in U.S. Pat. No. 8,188,069); (S)-[1-(1-methyl-2-oxo-5-phenyl-2,3-dihydro-1H-azepin-3-ylcarbamoyl)-ethyl]-carbamic acid tert-butyl ester (described in U.S. Pat. No. 8,188,069); [(S)-1-(5-isopropyl-1-methyl-2-oxo-2,3-dihydro-1H-azepin-3-ylcarbamoyl)-ethyl]carbamic acid tert-butyl ester (described in U.S. Pat. No. 8,188,069); [(S)-1-(1-methyl-2-oxo-4-phenyl-2,3-dihydro-1H-azepin-3-ylcarbamoyl)-ethyl]carbamic acid tert-butyl ester (described in U.S. Pat. No. 8,188,069); [(S)-1-(1-methyl-2-oxo-6-phenyl-2,3-dihydro-1H-azepin-3-ylcarbamoyl)-ethyl]-carbamic acid tert-butyl ester (described in U.S. Pat. No. 8,188,069); (S)-2-amino-N-(1-methyl-2-oxo-5-phenyl-2,3-dihydro-1H-azepin-3-yl)-propionamide (described in U.S. Pat. No. 8,188,069); (S)-2-amino-N-(5-isopropyl-1-methyl-2-oxo-2,3-dihydro-1H-azepin-3-yl)propionamide (described in U.S. Pat. No. 8,188,069); (S)-2-Amino-N-(I-methyl-2-oxo-6-phenyl-2,3-dihydro-1H-azepin-3-yl)propionamide hydrochloride (described in U.S. Pat. No. 8,188,069); (S)-2-Amino-N-(I-methyl-2-oxo-4-phenyl-2,3-dihydro-1H-azepin-3-yl)propionamide hydrochloride (described in U.S. Pat. No. 8,188,069); (S)-2-fluoro-3-methyl-butyric acid (described in U.S. Pat. No. 8,188,069); (S)-2-hydroxy-3-methyl-N—[(S)-1-((S)-1-methyl-2-oxo-5-phenyl-2,3-dihydro-1H-azepin-3-yl-carbamoyl)-ethyl]-butyramide (described in U.S. Pat. No. 8,188,069); (S)-2-fluoro-3-methyl-N—[(S)-1-(1-methyl-2-oxo-5-phenyl-2,3-dihydro-1H-azepin-3-ylcarbamoyl)-ethyl]-butyramide (described in U.S. Pat. No. 8,188,069); (S)-2-hydroxy-N—[(S)-1-(5-isopropyl-1-methyl-2-oxo-2,3-dihydro-1H-azepin-3-ylcarbamoyl)ethyl]-3-methyl-butyramide (described in U.S. Pat. No. 8,188,069); (S)-2-hydroxy-3-methyl-N—[(S)-1-(1-methyl-2-oxo-4-phenyl-2,3-dihydro-1H-azepin-3-ylcarbamoyl)-ethyl]-butyramide (described in U.S. Pat. No. 8,188,069); (S)-2-hydroxy-3-methyl-N—[(S)-1-(1-methyl-2-oxo-6-phenyl-2,3-dihydro-1H-azepin-3-ylcarbamoyl)-ethyl]-butyramide (described in U.S. Pat. No. 8,188,069); and(S)-2-fluoro-3-methyl-N—[(S)-1-(1-methyl-2-oxo-6-phenyl-2,3-dihydro-1H-azepin-3-ylcarbamoyl)-ethyl]-butyramide (described in U.S. Pat. No. 8,188,069), or pharmaceutically acceptable salts thereof.

Additional examples of gamma-secretase inhibitors are disclosed in U.S. Patent Application Publication Nos. 2004/0029862, 2004/0049038, 2004/0186147, 2005/0215602, 2005/0182111, 2005/0182109, 2005/0143369, 2005/0119293, 2007/0190046, 2008/008316, 2010/0197660 and 2011/0020232; U.S. Pat. Nos. 6,756,511; 6,890,956; 6,984,626; 7,049,296; 7,101,895; 7,138,400; 7,144,910; 7,183,303; 8,188,069; and International Publication Nos. WO 1998/28268; WO 2001/70677, WO 2002/049038, WO 2004/186147, WO 2003/093253, WO 2003/093251, WO 2003/093252, WO 2003/093264, WO 2005/030731, WO 2005/014553, WO 2004/039800, WO 2004/039370, WO 2009/023453, EP 1720909, EP 2178844, EP 2244713.

The entire disclosures of all of the foregoing are hereby incorporated by reference herein.

Methods for Using Bioartificial Lungs

This document also provides methods and materials for using bioartificial lung tissues and, in some cases, promoting lung function. In some embodiments, the methods provided herein can be used to restore some lung function in patients having diseases that impair or reduce lung capacity (e.g., cystic fibrosis, COPD, emphysema, lung cancer, asthma, pulmonary hypertension, lung trauma, or other genetic or congenital lung abnormalities, e.g., bronchogenic cyst, pulmonary agenesis and hypoplasia, polyalveolar lobe, alveolocapillary dysplasia, sequestration including arteriovenous malformation (AVM) and scimitar syndrome, pulmonary lymphangiectasis, congenital lobar emphysema (CLE), and cystic adenomatoid malformation (CAM) and other lung cysts). The methods provided herein also include those wherein the subject is identified as in need of a particular stated treatment, e.g., increased lung function, or increased or improved lung capacity.

Bioartificial lung tissues (e.g., whole organs or portions thereof) can be generated according to the methods provided herein. In some embodiments, the methods comprise transplanting a bioartificial lung tissue as provided herein to a subject (e.g., a human patient) in need thereof. In some embodiments, a bioartificial lung tissue is transplanted to the site of diseased or damaged tissue. For example, bioartificial lung tissues can be transplanted into the chest cavity of a subject in place of (or in conjunction with) a non-functioning or poorly-functioning lung; methods for performing lung transplantation are known in the art, see, e.g., Boasquevisque et al., *Proceedings of the American Thoracic Society* 6:66-78 (2009); Camargo et al., *Eur J Cardiothorac Surg* 2008; 34:1206-1209 (2008); Yoshida et al., *Ann Thorac Cardiovasc Surg.* 11(1):7-11 (2005); Venuta et al., Transplantation Proceedings 37(6):2682-2683 (2005); Yang and Conte, *Transplantation Proceedings* 32(7):1521-1522 (2000); Gaissert and Patterson, "Surgical Techniques of Single and Bilateral Lung Transplantation," in The Transplantation and Replacement of Thoracic Organs, 2d ed. Springer Netherlands (1996).

The methods can include transplanting a bioartificial lung or portion thereof as provided herein during a surgical procedure to partially or completely remove a subject's lung and/or during a lung resection. The methods can also include harvesting a lung or a portion thereof from a live donor or cadaver and preserving or regenerating the lung in a bioreactor described herein. In some cases, the methods provided herein can be used to replace or supplement lung tissue and function in a subject, e.g., a human or animal subject.

Any appropriate method(s) can be performed to assay for lung function before or after transplantation. For example, methods can be performed to assess tissue healing, to assess functionality, and to assess cellular in-growth. In some cases, tissue portions can be collected and treated with a fixative such as, for example, neutral buffered formalin. Such tissue portions can be dehydrated, embedded in paraffin, and sectioned with a microtome for histological analysis. Sections can be stained with hematoxylin and eosin (H&E) and then mounted on glass slides for microscopic evaluation of morphology and cellularity. For example, histology and cell staining can be performed to detect seeded cell propagation. Assays can include functional evaluation of the transplanted tissue matrix or imaging techniques (e.g., computed tomography (CT), ultrasound, or magnetic resonance imaging (e.g., contrast-enhanced MRI)). Assays can further include functional tests under rest and physiologic stress (e.g., body plethysmography, lung function testing). Functionality of the matrix seeded with cells can be assayed using methods known in the art, e.g., histology, electron microscopy, and mechanical testing (e.g., of volume and compliance). Gas exchange can be measured as another functionality assay. To assay for cell proliferation, thymidine kinase activity can be measured by, for example, detecting thymidine incorporation. In some cases, blood tests can be performed to evaluate the function of the lungs based on levels of oxygen in the blood.

To facilitate functionality assays during culture, any line of the bioreactor apparatus' described herein may include sampling ports to allow for single or real-time measurements of functionality parameters (e.g., pH, glucose, lactate, Na, K, Ca, Cl, bicarb, $O_2$, $CO_2$, sat). Metabolites may also be used to monitor cell number and viability using colorimetric assays, and biochemical assays may be used to monitor cell maturation (e.g., measuring surfactant protein, etc.) For example, an increased concentration of surfactant can indicate that the culture lung possesses sufficient epithelial cells to withstand dry ventilation. In some cases, endothelial barrier function may be used as a marker of vascular maturity. Lungs can be perfused with different sizes of molecules (such as dextrans of defined sizes and albumin), and microbeads (increasing sizes from 0.2 to 5 um), as well as isolated red blood cells. Bronchoalveolar lavage fluid can then be sampled to assess leakage of these markers into the alveolar space. For example, 500-kDa dextran can be used in combination with a Bronchoalvelar lavage assay to determine the percentage of dextran retained within the vascular compartment. An increase in the percentage of dextran retained indicates an improvement in the barrier function because barrier function to dextran is dependent on viable and functional endothelium, while dextran will diffuse across a denuded vascular basement membrane (e.g., in an acellular lung) over time during constant perfusion. For example, a cadaveric lung may retain substantially all of the dextran within the vascular compartment while acellular lungs may retain a small percentage of the dextran (e.g., 10.0%±8.0%). Leakage of these markers into the alveolar space greater than a tolerated minimum (for example >10% of 4 um microbeads, or greater than 20% of 0.2 um microbeads) can be used to indicate that the lung is not sufficiently mature to withstand dry ventilation.

In some cases, molecular biology techniques such as RT-PCR can be used to quantify the expression of metabolic (e.g. surfactant protein, mucin-1) and differentiation markers (e.g. TTF-1, p63, surfactant protein C). Any appropriate RT-PCR protocol can be used. Briefly, total RNA can be collected by homogenizing a biological sample (e.g., tendon sample), performing a chloroform extraction, and extracting total RNA using a spin column (e.g., RNeasy® Mini spin column (QIAGEN, Valencia, Calif.)) or other nucleic acid-binding substrate. In other cases, markers associated with lung cells types and different stages of differentiation for such cell types can be detected using antibodies and standard immunoassays.

Airway Organ Bioreactor Apparatus

An exemplary airway organ bioreactor and methods of use thereof are described in WO 2015/138999, which is incorporated herein by reference in its entirety. Other exemplary bioreactors are described in Charest et al., Biomaterials. 2015 June; 52:79-87; Gilpin et al., Ann Thorac Surg. 2014 November; 98(5):1721-9; discussion 1729; Price et al., Tissue Eng Part A 2010; 16(8):2581-91; Petersen et al., Cell Transplant 2011; 20(7):1117-26; Bonvillain et al., J Vis Exp 2013; (82):e50825; Nichols et al., J Tissue Eng Regen Med. 2016 Jan. 12. doi: 10.1002/term.2113.

Figure 19:
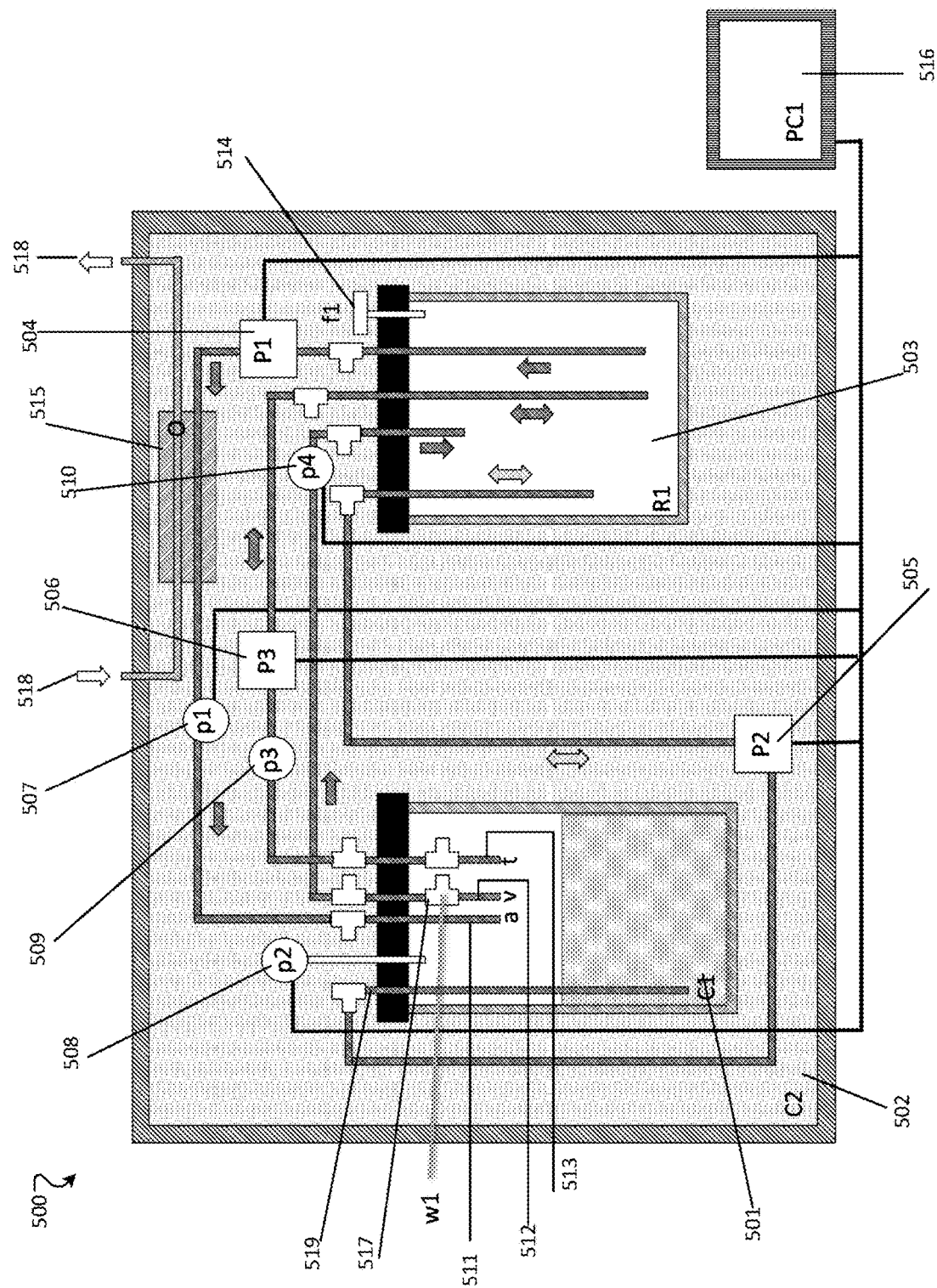
FIG. 19. A schematic diagram of an exemplary lung bioreactor.

For example, referring to FIG. 19, components of a bioreactor 500 as described in WO 2015/138999, include a lung chamber 501, an incubator chamber 502, a media reservoir 503, an arterial perfusion pump 504, a drainage pump 505, a wet ventilation pump 506, an arterial pressure sensor 507, a chamber pressure sensor 508, a tracheal pressure sensor 509, a venous pressure sensor 510, an arterial line 511, a venous line 512, a tracheal line 513, a sterile filter 514, an oxygenator 515, a control module 516, and a venous valve 517. Lung chamber 501 holds a lung matrix (not shown). Similar to the bioreactors 100, 200, and 400 as described in WO 2015/138999, the pulmonary artery of lung is connected to the arterial line 511, the pulmonary vein of the lung is connected to venous line 512, and the trachea of the lung is connected to the tracheal line 513. In addition to the features of the bioreactor 200 as described in WO 2015/138999, the bioreactor 500 further includes the wet ventilation pump 506 connected to the tracheal line 513. The wet ventilation pump 506 enables positive pressure liquid ventilation. Wet ventilation pump 506 draws fresh media from the media reservoir 503 and pumps the media through the tracheal line 513 thereby inflating the lung with liquid (e.g., media). The wet ventilation pump 506 is bi-directional and aspirates liquid from the tracheal line thereby deflating the lung.

Because the wet ventilation pump draws directly from the media reservoir 503, the lung matrix is continuously inflated with fresh media. The control module 516 controls the operation (e.g., duration, direction, and speed) of the wet ventilation pump 506 based on the pressure readings transmitted by the tracheal pressure sensor 509. For example, a positive inspiratory pressure of 5 to 45 cm $H_2O$ is applied during inspiration, while an expiratory pressure of 5 to −15 cm $H_2O$ is applied during expiration. During wet ventilation and dry ventilation modes, ventilation can be pressure controlled (PC) or volume controlled (VC). In a pressure-controlled mode, the pump provides a defined inspiratory pressure and a defined expiratory pressure for a defined period (inspiratory time, expiratory time) with the possibility of positive, neutral, and negative pressure plateaus, at a defined rate. In a volume controlled ventilation mode, the pump generates a defined inspiratory pressure until a certain volume has been inspired, then holds a defined plateau, then generates an expiratory pressure until a certain defined volume is exhaled, or until a certain defined target pressure has been reached, then the pump may hold at a neutral pressure or a defined exhaled plateau pressure. Volume movements may be measured by a variety of flow meters (e.g., heat based, differential pressure-based or ultrasonic). These flow meters have to be attached to the tracheal line near the lung chamber to provide most accurate flow measurements.

As described with respect to the bioreactor 200 as described in WO 2015/138999, any fluid shift from the lung tissue to graft chamber 501 is drained automatically back to the media reservoir 503 using the bi-directional drainage pump 505. The control module 516 activates drainage pump 505 based on data gathered from the chamber pressure sensor 508.

EXAMPLES

The invention is further described in the following examples, which do not limit the scope of the invention described in the claims.

Example 1. Regenerative Potential of Human Airway Stem Cells in Lung Epithelial Engineering Conventionally, a restrictive lineage concept in lung epithelial maintenance and repair has been held. Basal epithelial cells are relatively undifferentiated and characteristically express the transcription factor Trp-63 (p63) and cytokeratins 5 and 14 (Krt5/14), and function as stems cells for the lung airway during repair (32). This was demonstrated in a model of denuded airway repair in vivo (43). Basal lung epithelial cells have been classified as multipotent adult tissue stem cells, which have the ability to generate basal (self-renewal), ciliated and Clara (club) cells following injury (21, 44). The traditional model of lineage hierarchy in the distal alveolar epithelium defines Type 2 pneumocytes as the progenitor cell for the terminally differentiated Type 1 pneumocyte (45, 46). Examples of new paradigms in lung epithelial lineage capacity include bronchioalveolar stem cells (BASCs), a proposed progenitor cell population for both bronchiolar club cells and alveolar cells (47). A bipotent alveolar progenitor cell has been reported in developing lungs that can transition to a mature type II pneumocyte progenitor after birth (48). The classical alveolar type II/type I differentiation hierarchy has also been challenged and a novel, bi-directional potential reported (49). Following influenza injury, delivery of Krt5$^+$ airways stem cells revealed distal lung incorporation and contribution to both type 1 and type II pneumocyte lineages (36). These studies highlight the evolving understanding of traditional cellular hierarchy and identity. Notch signaling is also fundamental in in epithelial fate decisions following injury (27). Low level Notch signaling is present in steady-state lung epithelium and increases following airway injury, driving differentiation of basal stem cells to a secretory lineage (39). A more nuanced understanding of both the magnitude and timing of Notch signaling in epithelial repair and distal pneumocyte cell differentiation is developing.

The present experiments aimed to exploit the capacity of this easily accessible and expandable basal stem cell population to respond to injury, and re-establish epithelial integrity and functional organisation (13, 44), in the context of whole organ engineering. The architectural and biological niches retained within the native extracellular matrix provide a valid template to guide cell engraftment and investigate mechanisms of lung tissue repair (50, 51), and in combination with extended biomimetic culture provide an important platform for the regeneration of human lung constructs.

Methods

The following materials and methods were used in the Examples below.

Study Approval

Donor lungs otherwise unsuitable for transplantation were obtained from the New England Organ Bank, following informed consent. Experiments were approved by the MGH IRB and Animal Utilization Protocol.

TABLE 1

Lung Donor Information

| Donor ID | Age (yrs) | Gender | BMI | DCD/DBD |
|---|---|---|---|---|
| HL55 | 34 | M | 36 | DBD |
| HL54 | 49 | M | 17 | DBD |
| HL52 | 51 | M | 22 | DCD |
| HL51 | 64 | F | 48 | DBD |
| HL49 | 30 | F | 27 | DBD |
| HL46 | 1 | F | 12 | DBD |
| HL45 | 35 | F | 32 | DBD |
| HL44 | 49 | M | 25 | DCD |
| HL43 | 49 | F | 28 | DCD |
| HL42 | 51 | M | 30 | DCD |
| HL39 | 47 | M | 21 | DBD |
| HL35 | 48 | F | 27 | DBD |
| HL33 | 64 | F | 23 | DBD |
| HL31 | 23 | M | 22 | DBD |
| HL30 | 58 | F | 25 | DCD |
| HL29 | 37 | M | 27 | DBD |
|  | 43.5 ± 15.6 | 8 Male: 8 Female | 26.4 ± 7.8 | 5 DCD: 11 DBD |

Data represents the age (years), gender (male (M) or female (F)), Body Mass Index (BMI), and donor status (Donation after Cardiac Death (DCD) or Donation after Brain Death (DBD)). Age and BMI are presented with the summarized mean±standard deviation.

Cell Isolation and Expansion

Figure 7A:
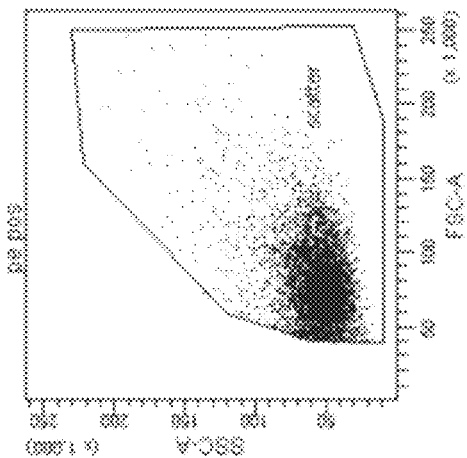
FIGS. 7A-B: Primary Endothelial Cell isolation and Culture. (A) Primary lung endothelial cells were isolated from large vessels and cultured for 5 days in EGM2 media prior to sorting for CD31+ population. Gating strategy demonstrates the exclusion of doublets and dead deals (Pacific Blue+), and the isolation of CD31+ population. Representative example presented. (B) Immunofluorescent staining of the sorted population in culture on gelatin-coated flasks, demonstrating endothelial purity. Scale bar=100 µm
Figure 7A:
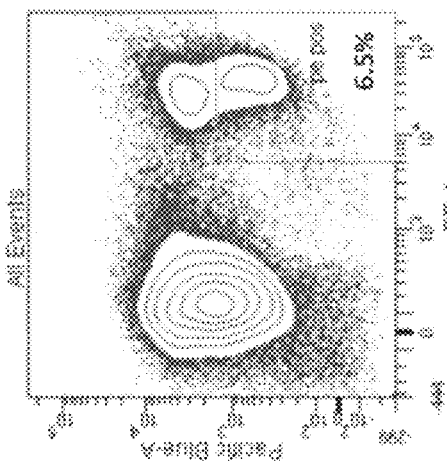
Figure 7A:
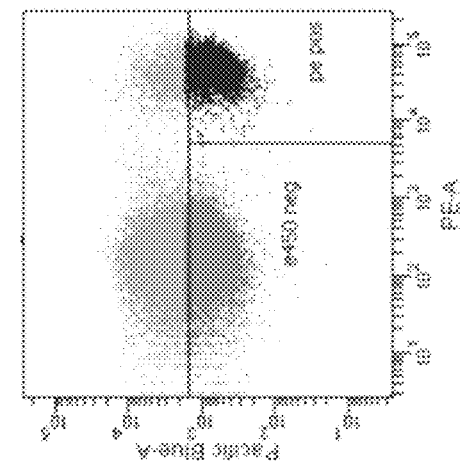
Figure 7B:
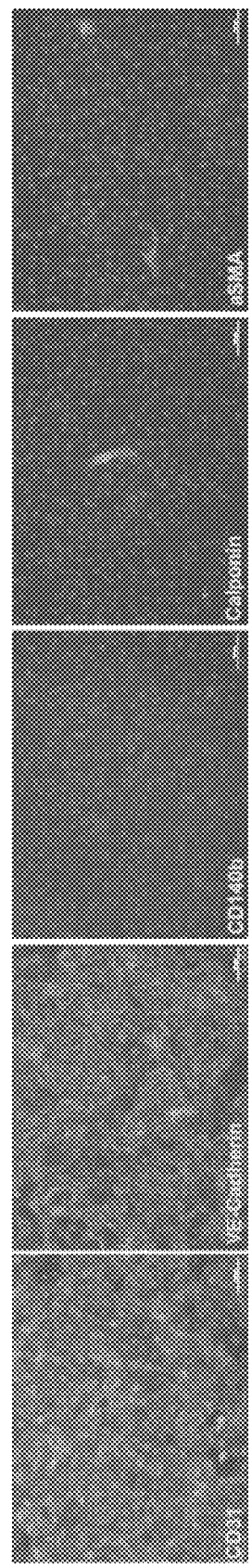

Donor lung peripheral tissue (1-inch cubed) was washed in αMEM and then chopped into ~¼ inch pieces with scissors and digested in 0.1 mg/ml DNAse (Sigma) and 1.4 mg/ml Pronase (Roche, 11459643001) for 24 hours/4° C. (52). Digested tissue was plated onto uncoated culture flasks in SAGM for 30 minutes/37° C., then non-adherent cells transferred and adhered to human Collagen-IV (Sigma-Aldrich C7521)-coated flasks. Epithelial cells were maintained in SAGM (Lonza, CC-3118) and passaged at 80% confluent (approximately 3-5 days/passage). For cells treated with γ-secretase inhibitors (1) 3-Isobutyl-1-methylxanthine (100 µg/ml IBMX, Sigma-Aldrich, 15879) and (2) N-[(3,5-Difluorophenyl)acetyl]-L-alanyl-2-phenyl]glycine-1,1-dimethylethyl ester (50 µg/ml DAPT, Selleck Chemicals, S2215), media was changed daily. Primary endothelial cells were isolated from the large vessels of donor lungs using the same digestion protocol. The endothelial population was sorted for CD31$^+$ purity by flow cytometry, and maintained and expanded on Gelatin coated flasks in EGM2 (Lonza, CC-3162) until utilized for human lung recellularization (See FIGS. 7A-B).

Air-Liquid Interface Culture

Primary epithelial cells at passage 3 were plated onto 0.4 µM Transwell inserts coated with collagen IV and maintained in submerged culture with SAGM for 5 days. Media was replaced with PneumaCult™-ALI medium (Stemcell Technologies, 05001) in the basal chamber only, and maintained for 21 days at Air-Liquid interface, with alternate day media changes.

3-Dimensional Sphere Assay

Primary epithelial cells at passage 3 were filtered through a 40 µm mesh to remove any cell clumps then transfer onto a 0.4 µM Transwell insert at a density of 5000 cells/90 uL of a 50:50 matrigel-to-SAGM substrate, following a previously published protocol (46). Single cell suspension was confirmed by light microscopy (40×). Cultures were maintained with SAGM in the basal chamber only for 7 days.

Lung Decellularization

Rat and human donor lungs were decellularized as previously described (2, 6).

Matrix Slice Culture Assay

Human lung matrix slices were prepared as previously describe (6). Primary epithelial cells (passage 3) were seeded to the matrix at 50,000 cells/slice and maintained with SAGM for 5 days.

Rat Lung Recellularization and Culture

Primary lung epithelial cells (passage 3) were harvested from 2-D culture, counted, and re-introduced to the scaffold airways in solution (20 ml) by gravity. Continuous media perfusion through the pulmonary artery was maintained at 4 ml/min by peristaltic pump and changed daily.

For continuous positive airway pressure (CPAP) rat lung culture, following epithelial recellularization and 7 days of constant perfusion culture with SAGM, media was changed to PneumaCult™-ALI (Stemcell Technologies, 05001) and CPAP was initiated at 20cmH$_2$O. Positive airway pressure by connecting the trachea to a secondary reservoir chamber, which was continuously pressurized to 20cmH$_2$O.

Human Lung Recellularization and Biomimetic Culture

Single lobes were surgically isolated from intact decellularized human lungs and cannulae were placed in the pulmonary artery, pulmonary vein, and bronchus. Lobes were sterilized by soaking in 0.1% peracetic acid in 4% Ethanol for 60 minutes/25° C., followed by 3×PBS washes, and then exposed to 10,000 Rad of γ-irradiation over 2 hrs. Isolated lobes were aseptically mounted in the bioreactor and tissue primed by SAGM perfusion overnight.

A total of 160-240×10$^6$ primary donor-derived CD31$^+$ endothelial cells were first delivered to the vasculature via the pulmonary artery by pump at a constant pressure of 50 mmHg. After 90 minutes, a total of 220-280×10$^6$ epithelial cells (passage 4) were delivered to the main airway in solution (500 ml total media) by pump at 50 ml/min. A total of n=4 independent lobes were recellularized, in separate experiments.

Constant perfusion of SAGM with 40 ng/ml VEGF was maintained for 7 (n=3) or 10 (n=1) days at 20-40 ml/min. Perfusion pressure was continuously monitored and maintained within physiologic range (mean=21.39±4.53 mmHg, see FIG. 5C). Negative pressure ventilation was generated via chamber pressure oscillations to achieve a breath rate of 6 breath cycles/minute. Ventilation was initiated on day 3 of culture and maintained for 2-hours/day. Media samples from the pulmonary artery, pulmonary vein, and chamber were tested by iSTAT cartridge (CG4+/CG8+, Abbott) daily.

Positive pressure ventilation challenge was performed on the final day of culture. Volume-controlled ventilation was applied using a Drager Evita 4 ventilator, with a tidal volume of 150-200 mL, a PEEP of 5 mmHg, and a respiratory rate of 12 breaths/min. Samples were analyzed after 10 minutes of ventilation with a FiO$_2$ of 21% and again after 10 minutes with and FiO$_2$ of 100%, using a GC3+ iSTAT cartridge.

On the final day of culture, a 0.05 mM Resazurin solution was circulated for 90 minutes at a constant flow of 30 ml/min, then tissue was inspected visually for metabolic conversion of dye colour. Tissue samples were then fixed in 5% formalin, or saved in RNAlater (Qiagen) for subsequent analysis.

Quantitative PCR

RNA was isolated using the RNEasy Plus (Qiagen). cDNA was transcribed using the Superscript III kit (Invitrogen). Quantitative gene expression was analyzed using Taqman probes and the OneStep Plus system (Applied Biosystems). Expression was normalized to β-Actin expression and relative to cadaveric lung tissue control samples.

Immunostaining

Primary Antibodies (1:100): p63 (Santa Cruz, sc-25268), Krt5 (Abcam, ab24647), E-cadherin (BD, 610181), Surfactant Protein-B (Millipore, AB3430), pro-Surfactant Protein-C (Abcam, ab3786), Aquaporin-5 (Abcam, ab92320), Acetylated α-Tubulin (Abcam, ab24610), $\alpha_2\beta_1$ integrin (Abcam, ab24697), $\alpha_3\beta_1$ integrin (Abcam, ab24696), and CD31 (Daki, M082301-2). Secondary antibodies (1:400): Alexafluor 488 and 594 (Life Technologies).

Results

Figure 1B:
Figures 1C, 1D:
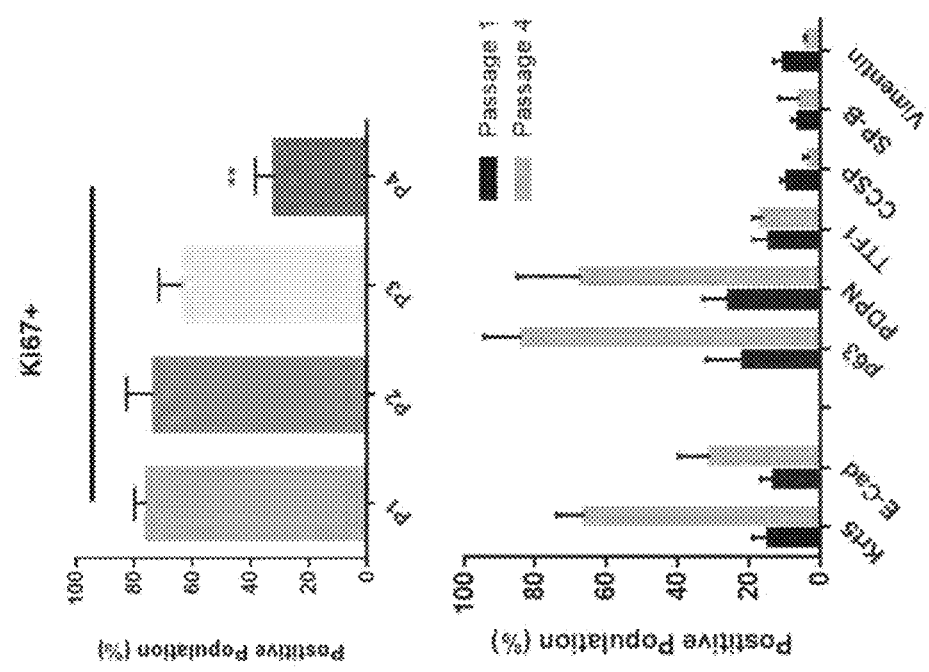
Figure 1E:
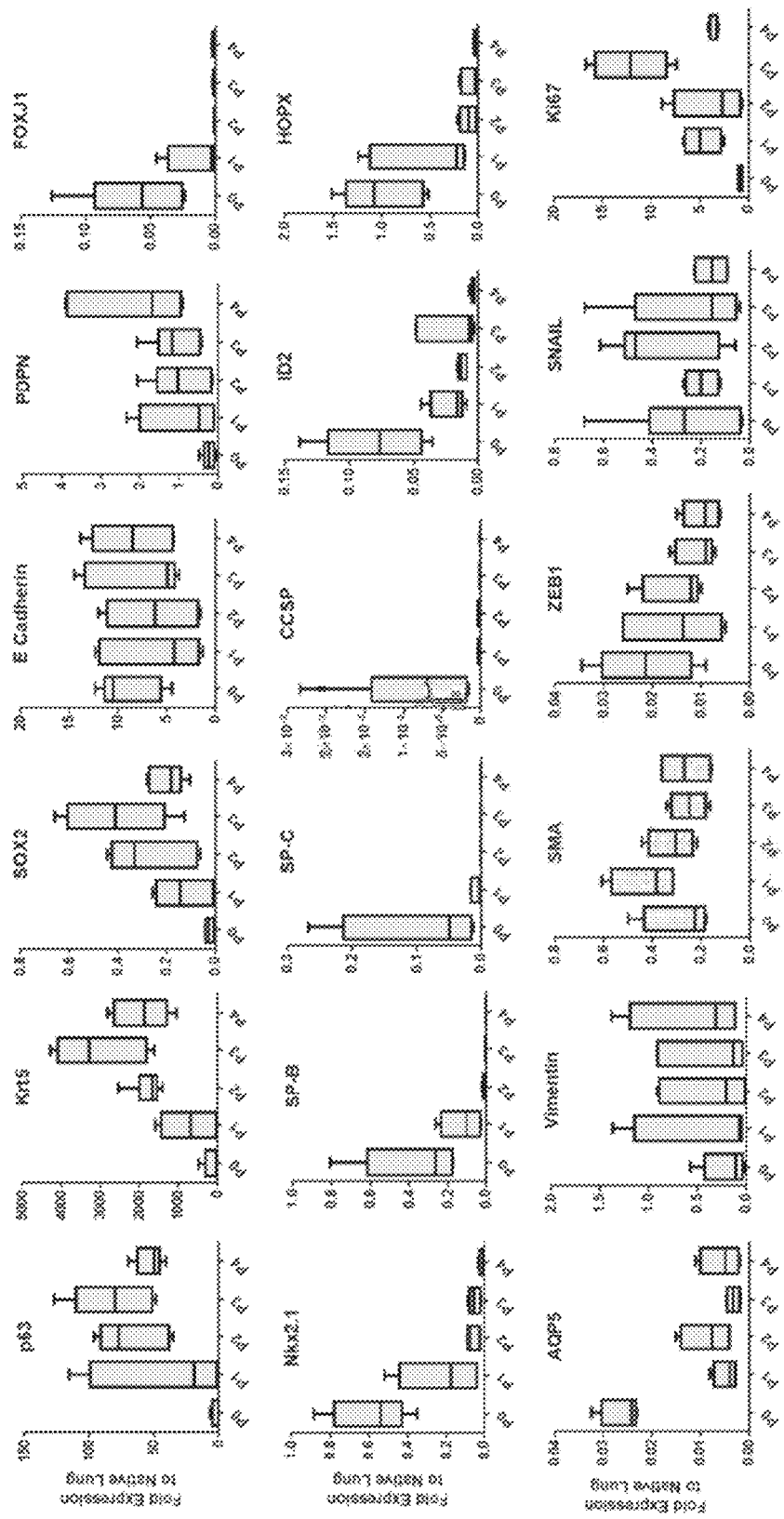
Figure 8A:
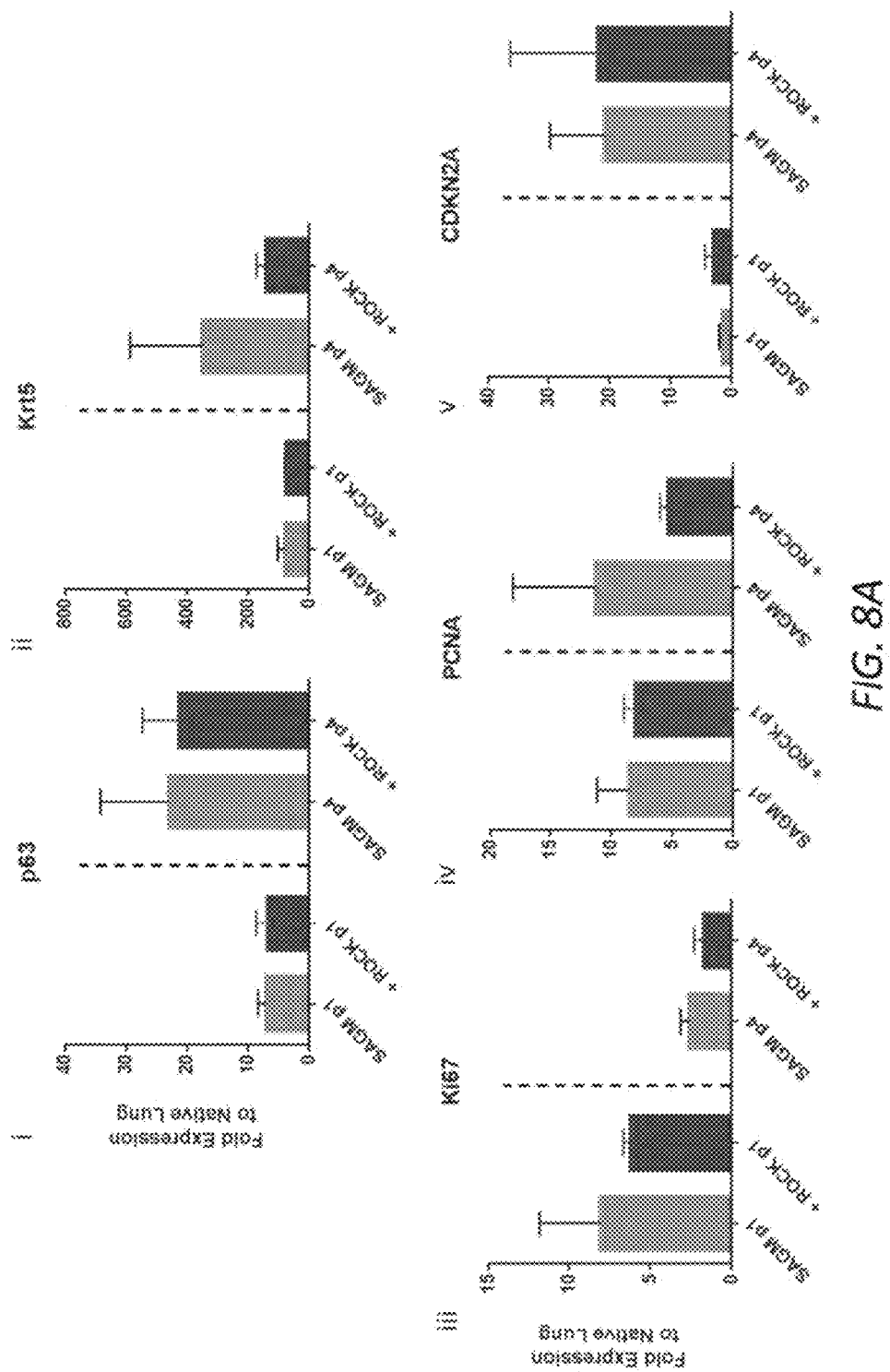

First a highly proliferative cell population was isolated from human cadaveric peripheral lung tissue. A robust expansion of the Krt5$^+$p63$^+$ basal stem cell population was reproducibly observed over serial passages in culture (FIGS. 1A-B). The proliferative capacity of the isolated cell population was maintained through 3 passages (Ki67$^+$ cells by staining, 63.4±8.08%), which began to decline by passage 4 (FIG. 1C). Phenotypic stability was further examined by flow cytometric analysis of passage 1 and passage 4 cells, confirming the expansion of the Krt5$^+$p63$^+$ basal stem cell lineage (FIG. 1D). Gene expression was longitudinally profiled (FIG. 1E), additionally confirming the enrichment of the airway stem cell population, with a parallel loss of type 1 and type 2 pneumocytes, and CCSP$^+$ secretory cells. No increase in expression of mesenchymal genes vimentin or smooth muscle actin (SMA) was measured during cell expansion, and no increase in the expression of epithelial-to-mesenchymal transition associated transcription factors ZEB1 and SNAIL. Maximal cell proliferation at passage 3 was also confirmed by gene expression of Ki67. In the present experiments, use of ROCK inhibitor Y-27632 (53) during cell isolation and passage did not enhance the basal cell population, or alter proliferation (Ki67, PCNA) or senescence (senescence-associated cyclin-dependent kinase inhibitor 2A, CDKN2A) (54) (FIGS. 8A-C) and was not used for in vitro expansion.

Figure 2A:
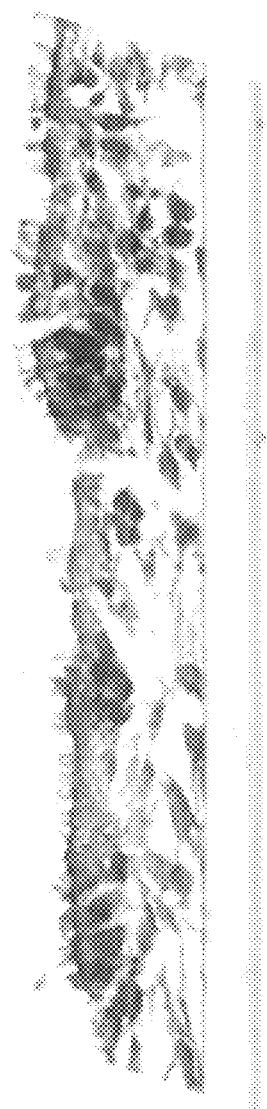
Figure 2B:
Figure 2E:
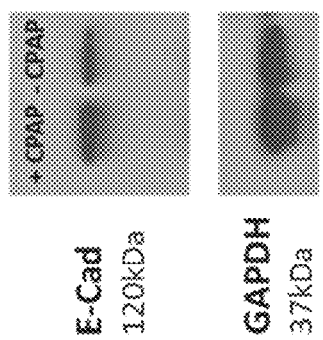
Figure 2F:
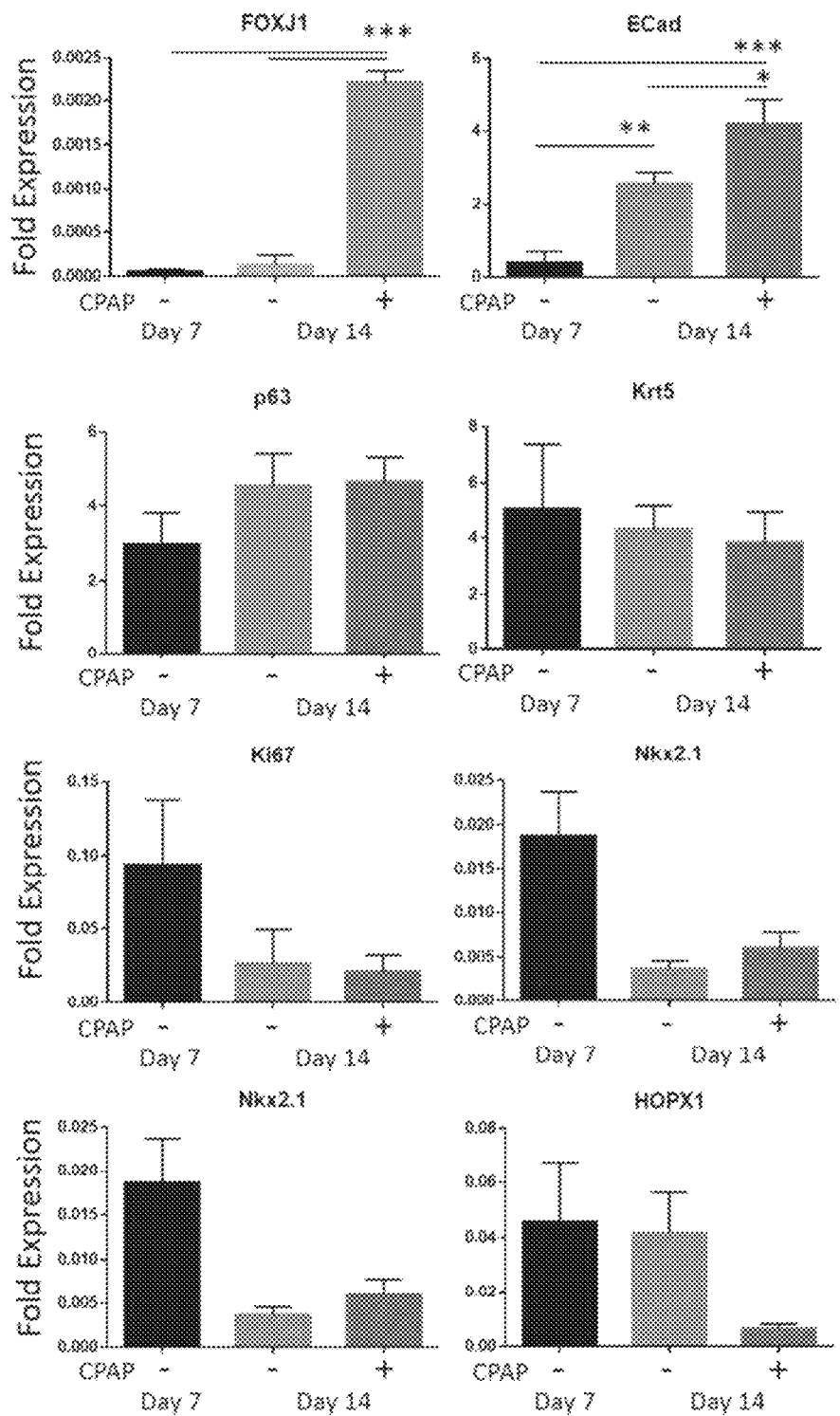

Successful formation of a functional epithelium on acellular lung scaffolds would require re-establishment of complex tissue containing multiple cell lineages. Therefore, the regenerative potential of the isolated and expanded cells was tested by confirming their capacity for ciliogenesis when cultured at air-liquid interface (ALI) in vitro (FIG. 2A). A pseudostratified epithelium was observed including an acetylated α-tubulin⁺ ciliated upper layer, a basal Krt5⁺p63⁺ cell layer, the nuclear expression of Forkhead box protein-J1 (FOXJ1), and cell-to-cell tight junction formation (E-cadherin), together indicating the preservation of phenotypical diversity, differentiation potential, and capacity for physiologic self-organization (FIG. 2B). To test this potential in whole organ recellularization, re-epithelialized rat lungs were maintained for 7-days under constant media perfusion, then transitioned to a continuous positive airway pressure (CPAP) model for an additional 7 days to recapitulate ALI on the lung scaffold, or maintained with vascular perfusion only, for a total of 14 days ex vivo culture (FIG. 2C). Extensive basal cell (Krt5⁺) repopulation was maintained following CPAP culture, lining the airway and alveolar architecture. Induction of FOXJ1 expression, increase in E-Cadherin intensity, and a decrease in proliferation (Ki67) was observed (FIG. 2D-E). This early induction toward a ciliated epithelial phenotype was confirmed by gene expression quantification, revealing a significant increase in FOXJ1 and E-Cadherin expression in CPAP lungs versus vascular perfusion-only lungs at day 7 and 14 of culture (FIG. 2F).

Figure 3A:
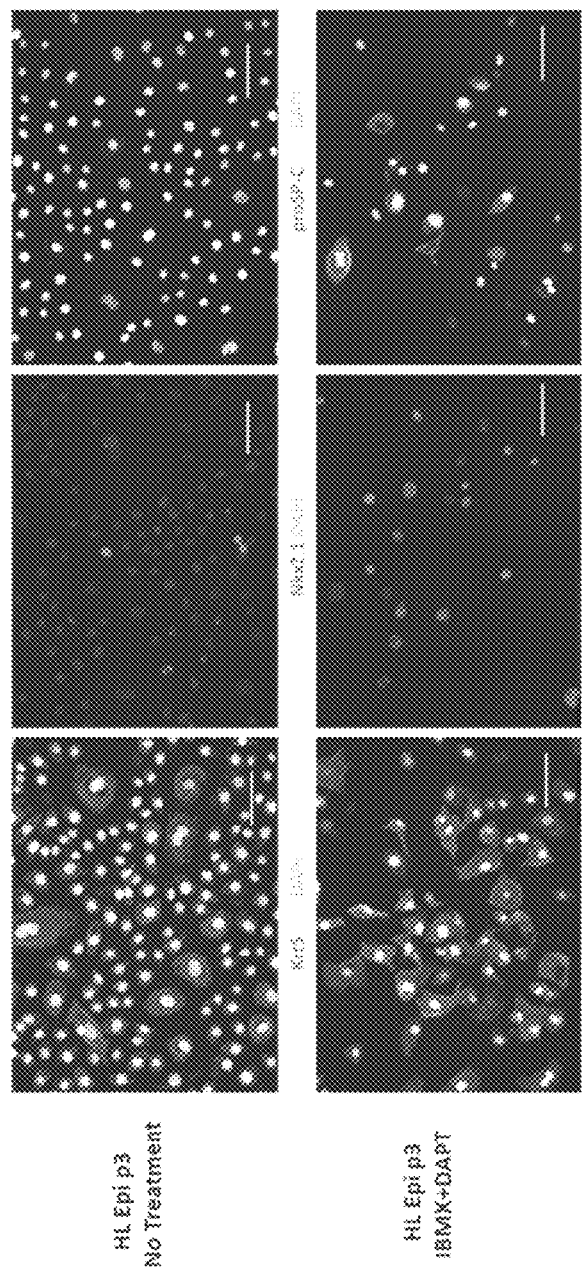
FIGS. 3A-H. Induction of a distal Type II pneumocyte phenotype by Notch inhibition. (A) Immunofluorescent images of primary epithelial basal cells in vitro (passage 3) treated with Notch inhibitors 3-isobutyl-1-methylxanthine (IBMX), a phosphodiesterase inhibitor, and N—[N-(3,5-Difluorophenacetyl-L-alanyl)]-(S)-phenylglycine t-butyl ester (DAPT, also known as GSI IX, a gamma secretase inhibitor) for 5 days, demonstrating the increase in surfactant protein-B (SP-B) positive cells. Scale bars=100 μm. (B) Quantitative PCR analysis of gene expression of cells treated with IBMX (100 DAPT (50 μM), or combination IBMX+DAPT for 5 days in vitro, demonstrating an increase in SP-B and SP-C expression. n=3 experimental replicates are shown. 1-way ANOVA with Dunnet post-test compared to No Treatment (NT). Although in this experiment DAPT and IBMX were ineffective alone, in other replicates they showed some activity. 3-dimensional culture assay demonstrating sphere formation. (C) Immunofluorescent images of spheres demonstrating a predominance of a Krt5+p63+ phenotype in 3D sphere culture. Scale bar=50 µm. (D) Haematoxylin and Eosin stained spheres demonstrating luminal development by day 7. (E) Bright field images of spheres in both untreated and Notch inhibited (IBMX+DAPT) cells on Day 7. Scale bar=100 µm. (F) Quantification of sphere number as a percentage of total cell number initially seeded, demonstrating a decrease in sphere formation in IBMX+DAPT treated cells. n=3 independent cultures quantified in experimental triplicate. Analyzed by T-test. (G) Quantitative PCR analysis of gene expression of sphere cultures on day 7, with or without Notch inhibition (IBMX+DAPT). Data from 3 independent cultures is shown, analyzed in experimental duplicate. Normalized to β-actin expression and relative to normal cadaveric lung tissue control. (H) SP-C protein could also be measured by ELISA in the conditioned media of BESCs (at passage 4, p4) following treatment with DAPT+IBMX, in vitro for 5 days. All error bars represent standard deviation, analyzed by t-test.
Figure 3B:
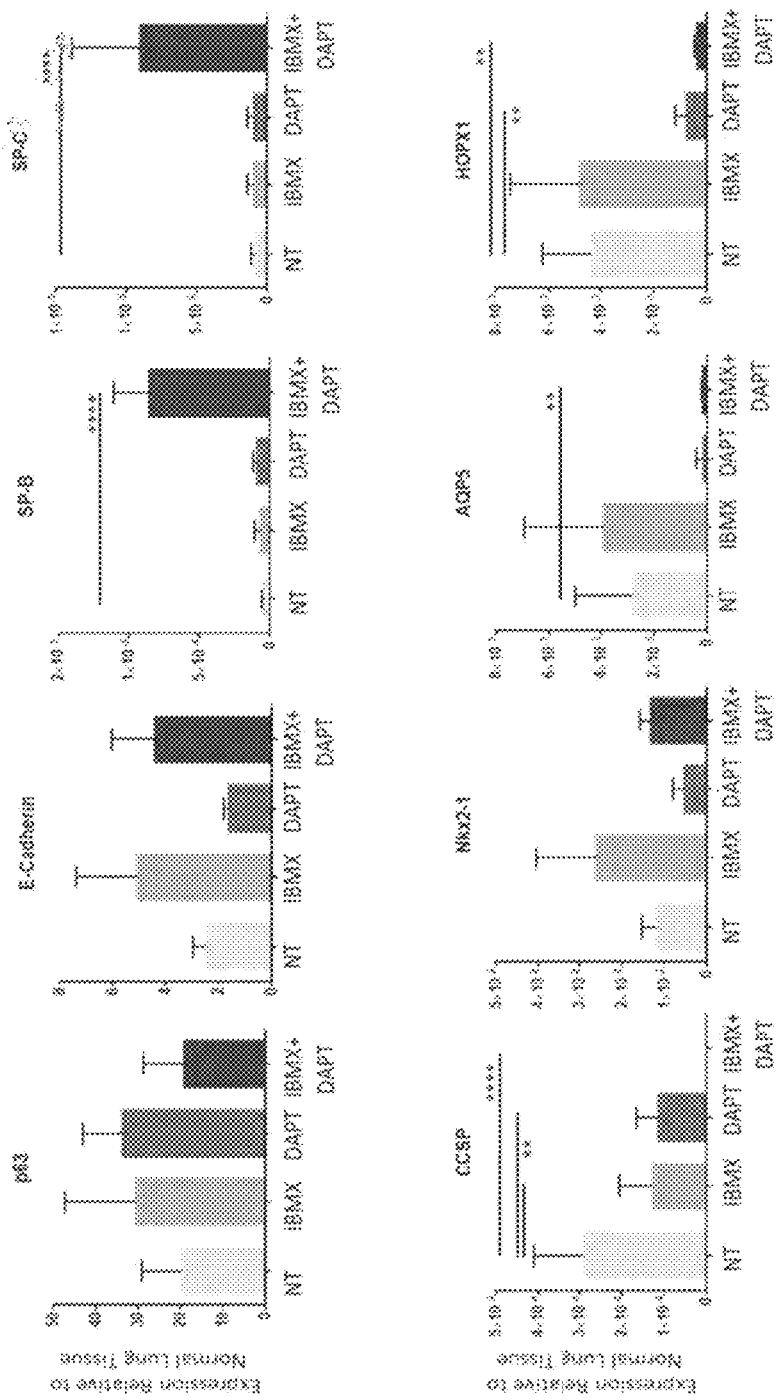
Figure 3D:
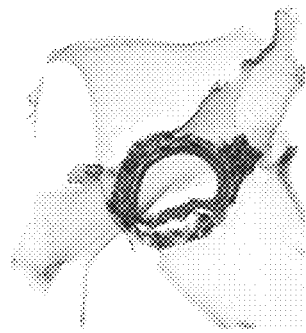
Figure 3D:
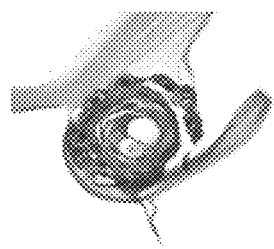
Figure 3D:
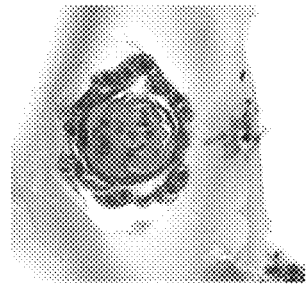
Figure 11:
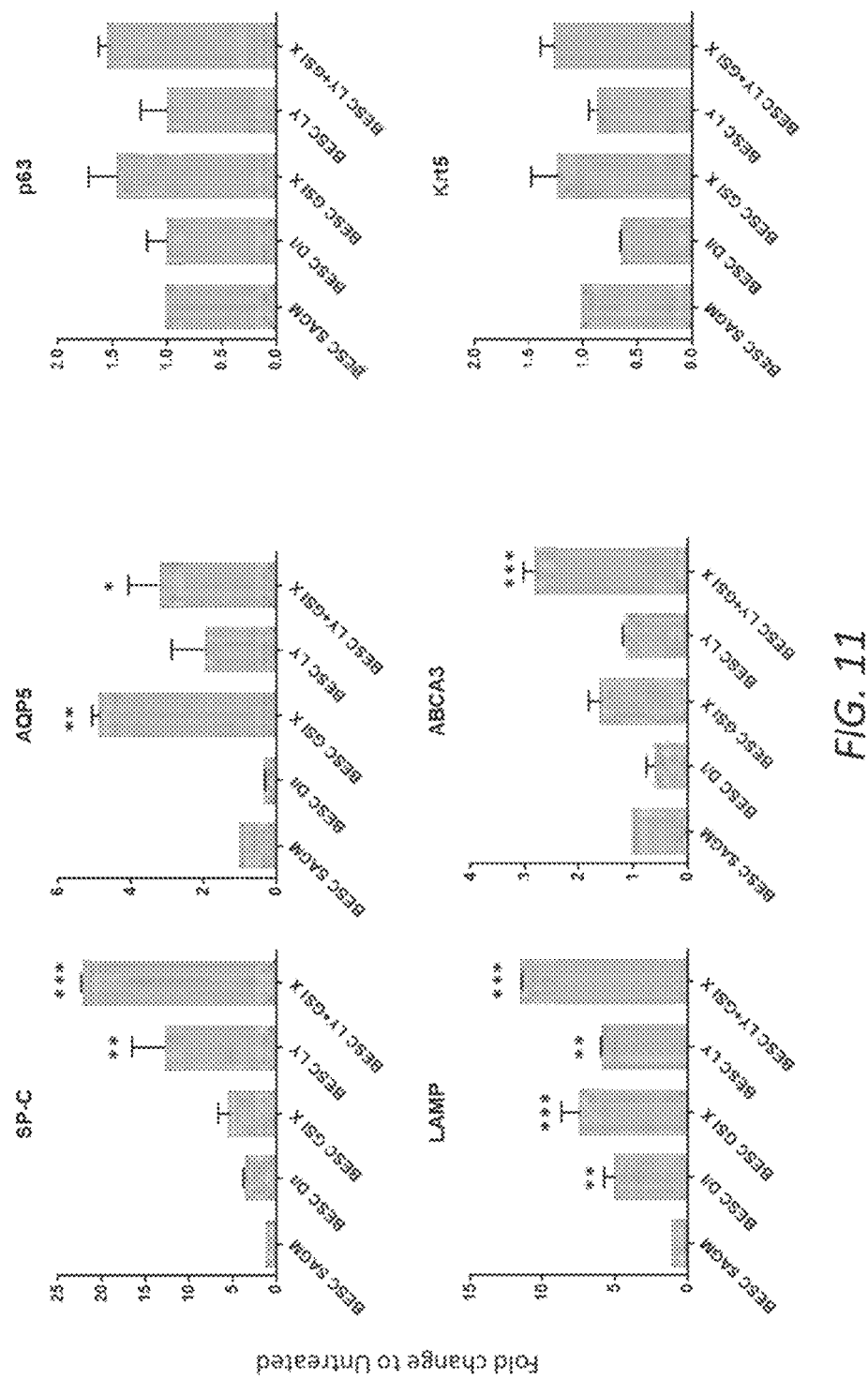
FIG. 11. Direct Inhibition of the Notch signal pathway using dual small molecules (in this figure, LY411575 and GSI-X) targeting gamma-secretase efficiently directed tissue-derived BESCs toward a distal pneumocyte fate in vitro. Quantitative PCR analysis of gene expression at the end of in vitro treatment (Day 5). Data from n=3 independent wells, analyzed in experimental replicate is shown. Expression normalized to β-Actin expression and fold-change calculated compared to untreated cells (SAGM). With this treatment, Type1 pneumocyte marker AQP5 was also increased, which was again not found with DAPT/IBMX treatment (as in FIG. 3).

Next cell plasticity was examined by inhibiting Notch signaling through γ-secretase activity. Although the results with single agents were somewhat variable depending on the donor cells, treatment with a combination of Notch inhibitors IBMX and DAPT to passage 3 cells in vitro induced both nuclear Nkx2.1 and cytoplasmic proSP-C expression (FIG. 3A). This was further confirmed by gene expression analysis demonstrating a significant increase in the type II pneumocyte markers surfactant protein-B (SP-B) and SP-C (22.06±0.29-fold increase following Notch inhibition, while preserving the basal stem cell population (p63) (FIG. 3B). A loss of type 1 pneumocyte markers Aquaporin 5 (AQP5) and HOPX1, and a loss of secretory cell marker expression (CCSP) was also quantified following Notch signal inhibition. Surfactant Protein-C production was also increased when measured in the conditioned media by ELISA (0.33±1.13 pg/ml untreated vs 1.13±0.09 pg/ml following Notch inhibition treatment). Treatment with GSI X and LY411575 also increased AQP5 expression (which is a marker of Type 1 cells not Type 2 cells, but Type 2 cells differentiate to Type 1 cells), but the IBMX+DAPT treatment did not support AQP5 expression (See FIG. 3 and FIG. 11).

Figure 3C:
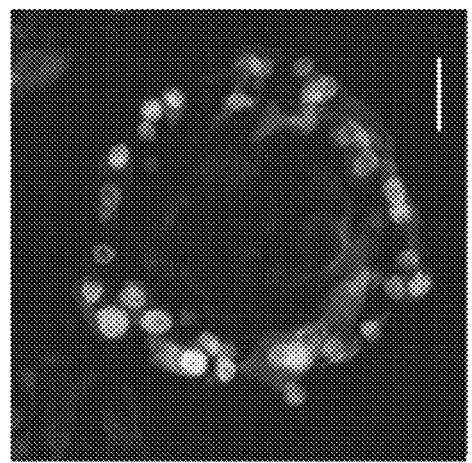
Figure 3F:
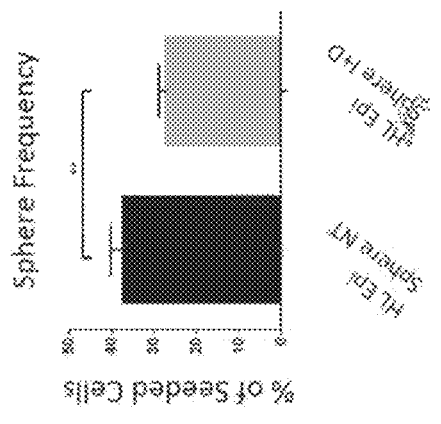
Figure 3E:
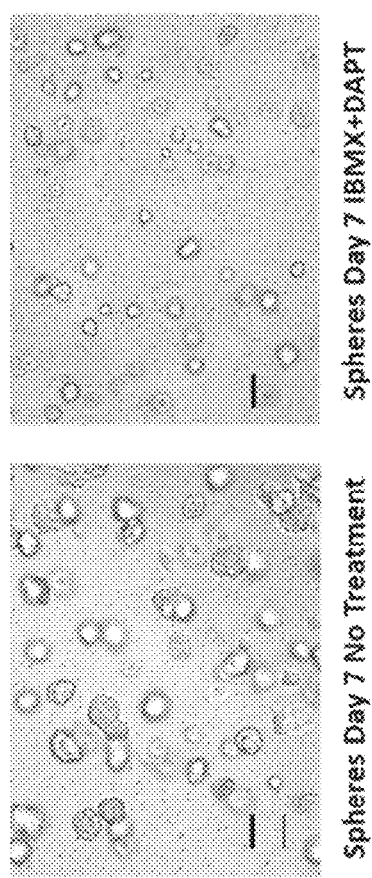
Figure 3G:
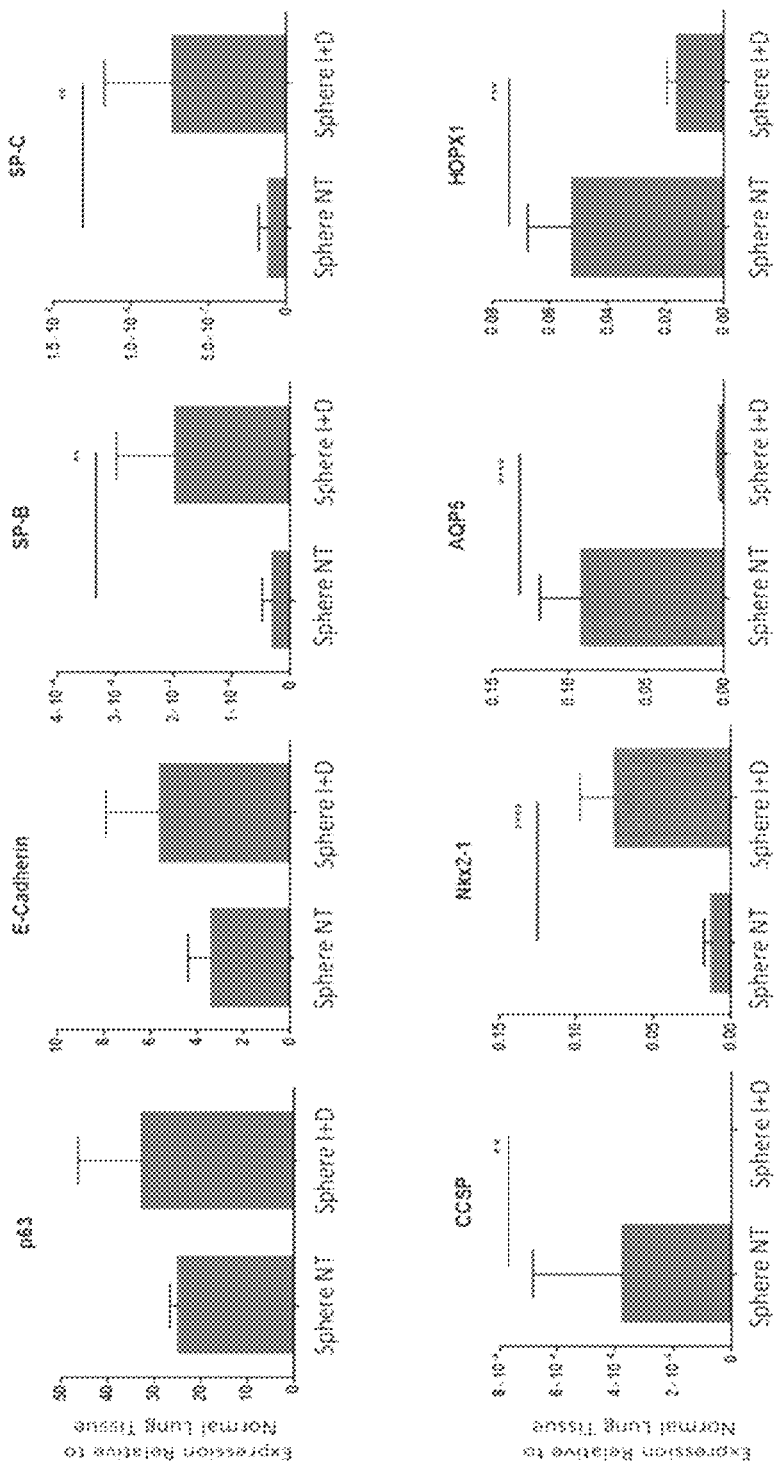
Figure 3H:
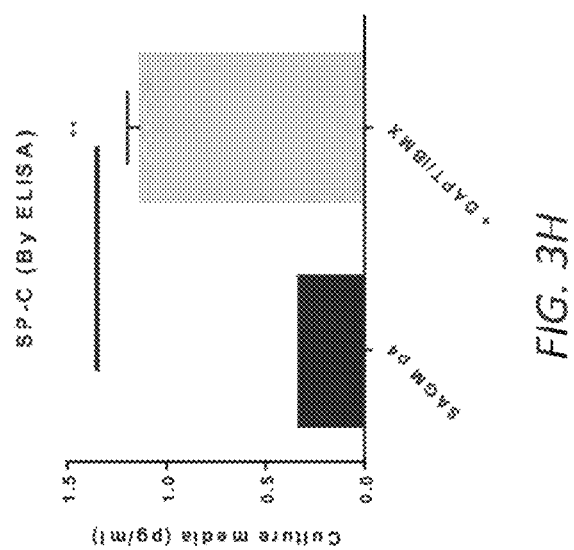

Single epithelial cells cultured in matrix support (Matrigel) could form 3D spheres over 7 days in vitro, with lumen development (FIG. 3D) and evidence of epithelial polarity (FIG. 3C). Cultures treated with dual Notch inhibition (IBMX+DAPT) formed significantly fewer spheres (FIG. 3E-F). Gene expression analysis further confirmed that inhibiting the Notch signaling pathway in 3D culture can promote a transition towards a type II pneumocyte population (SP-B, SP-C), a loss of type I pneumocytes (AQP5, HOPX1), loss of club cells (CCSP), and no significant change in basal stem cell marker expression (p63) (FIG. 3G).

Figure 4A:
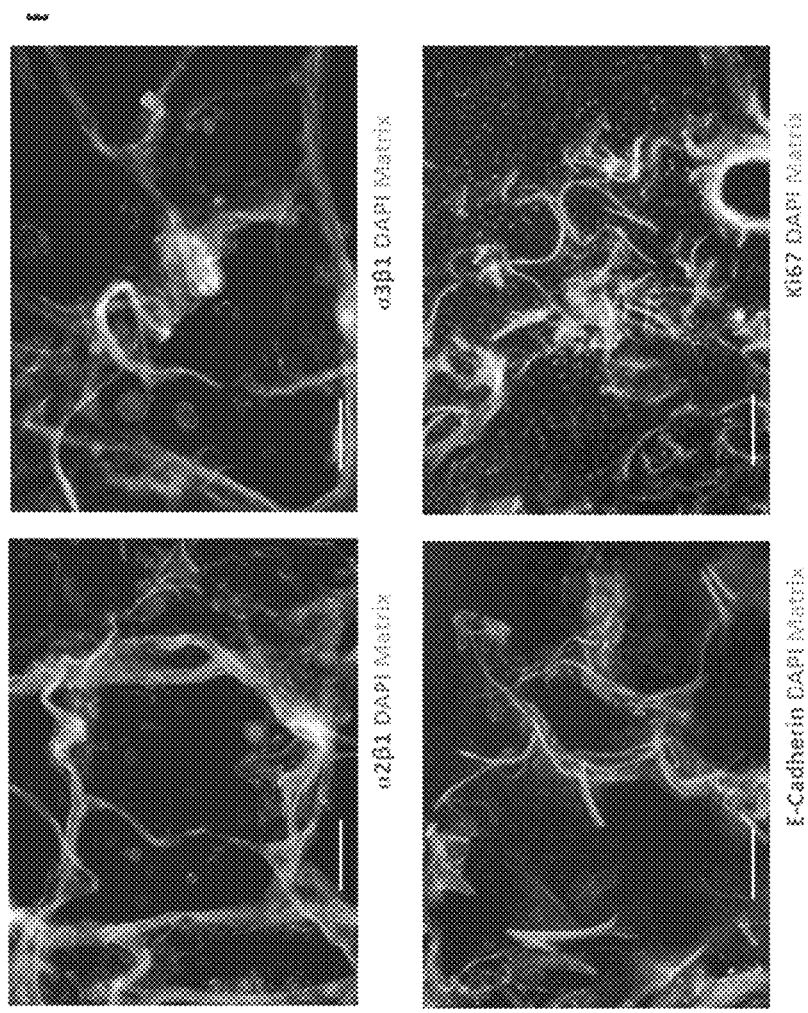
FIGS. 4A-E. Induction of primary basal airway stem cells to distal type II pneumocyte phenotype in decellularized lung scaffold culture. (A) Co-culture of basal epithelial stem cells with human decellularized lung slices for 5 days demonstrating cell attachment to lung matrix via integrin α2β1 and α3β1, the formation of tight junctions along areas of matrix attachment (E-Cadherin), and continued proliferation (Ki67+). Scale bar=100 µm. (B) Quantitative PCR analysis of gene expression in cell-matrix culture with or without Notch inhibition (IBMX+DAPT) for 5 days, demonstrating the induction of SP-B and SP-C, and loss of Club Cell Secretory Protein (CCSP expression after treatment. Data from 2 separate experiments shown, with cells seeded to matrix derived from two different lung donors (n=3 to HL30 and n=3 to HL38), analyzed in experimental duplicate. Normalized to β-actin expression and relative to normal cadaveric lung tissue control. Analyzed by T-test (IBMX+DAPT vs. NT). Error bars represent standard deviation. (C) Biomimetic culture of lungs recellularized with primary basal stem cells (20×10$^6$) plus IBMX+DAPT treatment. (D) Quantitative PCR analysis of gene expression in recellularized lungs treated with IBMX+DAPT for 5 days in constant perfusion culture compared to No Treatment lung (Day 5). n=3 independent tissue samples analyzed per lung, in experimental triplicates. Normalized to β-actin expression and relative to normal cadaveric lung tissue control. Analyzed by T-test (IBMX+DAPT vs. NT). Error bars represent standard deviation. (E) Immunofluorescent images of recellularized lungs at Day 5 (No Treatment vs IBMX+DAPT Notch inhibition), confirming the maintenance of Krt5/p63+ basal cell population, an increase tight junction intensity (E-Cadherin), an increase in SP-C positive cells, and a loss of Aquaporin-5 positive cells. Scale bars=50 µm FIGS. 5A-K. Recellularization and culture of whole decellularized human lung scaffolds with primary human lung basal stem cells. (A) Schematic of exemplary lung bioreactor capable of constant organ perfusion and negative pressure ventilation. (B) Single human decellularized lung lobe in bioreactor with access ports for pulmonary vein, airway, and pulmonary artery highlighted. Lobes were seeded with primary PAECs (pulmonary artery endothelial cells, 160-240×106) and BESCs (basal epithelial stem cells, 220-280×106, n=3) and maintained under constant media perfusion plus periodic negative pressure ventilation. (C) Pulmonary artery pressure over 8 days of recellularized lung perfusion culture, n=3 recellularized lungs. Data represents mean pressure+/−SD. (D-E) Change in (D) Glucose measurements in media sampled from the lung culture media. Media was changed every 48-hours, and values represent the change in glucose concentration (mg/dL) and (E) lactate concentration (mmol/L) after 48-hours of organ perfusion, compared to fresh media. Data shown represent n=2 independent lung cultures per time point. Error bars represent standard error. (F) Representative pressure traces during negative pressure ventilation (breath rate of 6/min). Pressures are simultaneously recorded in the organ chamber, pulmonary artery, PEEP chamber, airway, and pulmonary vein. (G) Peak transmural pressure (mmHg) during ventilation. (H) Calculated tidal volume (mL) during ventilation. Box plots represent median, plus the first and third quartile. Whiskers represent the range of data. Outliers (points greater than 1.5×IQR of the box plot) are represented by a plus sign (+). (I) Representative pressure-volume loop generated during negative pressure ventilation in the bioreactor. Traced loop t=0 is represented as Blue and t=final is represented as Red (J) Endpoint positive pressure ventilation challenge of a single lower lobe. (K) Representative measurement of pH, $pO_2$, $pCO_2$, and $HCO_3$ of perfusate during positive pressure ventilation challenge. Lobe was recellularized and cultured for 7 days prior to testing and functional challenge was with 21% and 100% FiO2.
Figure 4B:
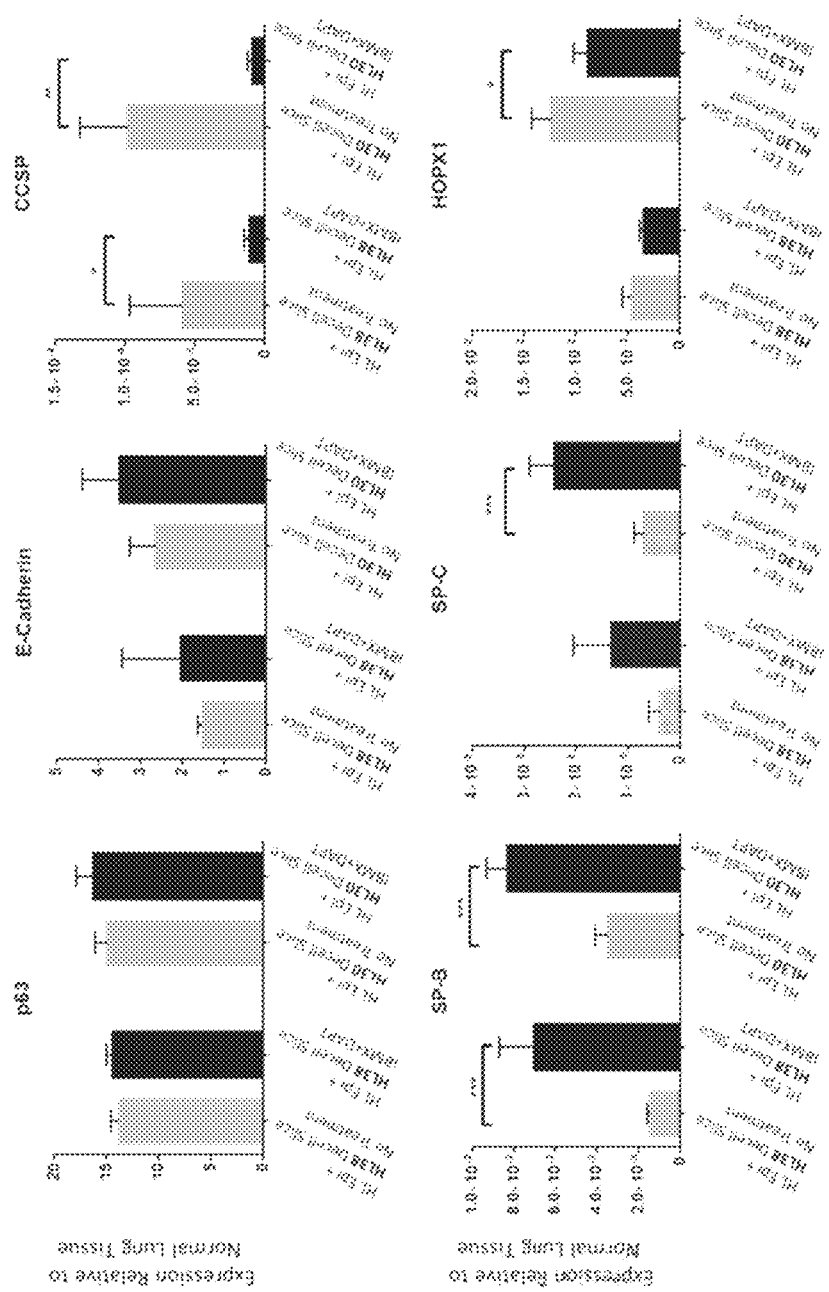
Figure 4C:
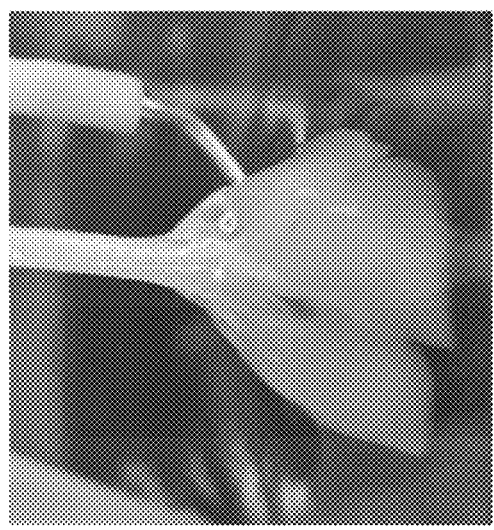
Figure 4D:
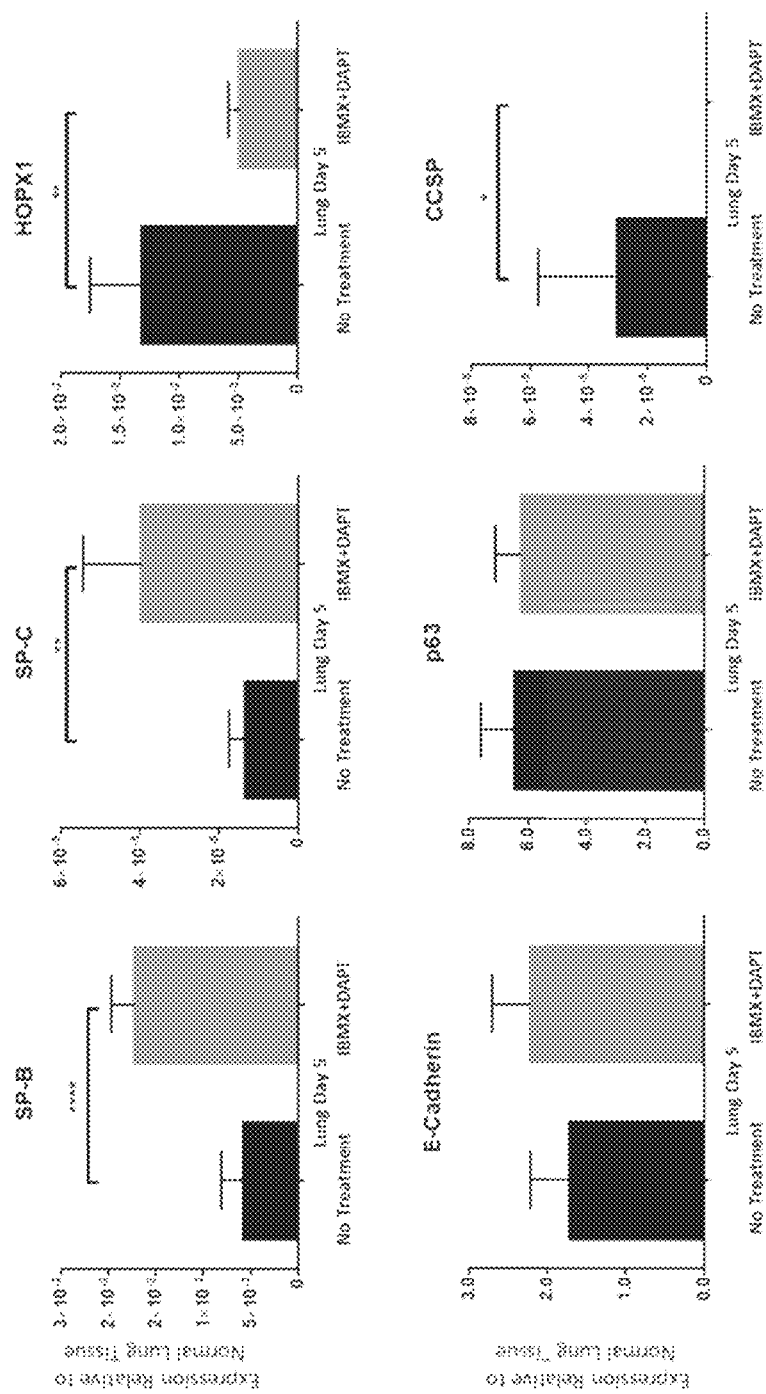
Figure 4E:
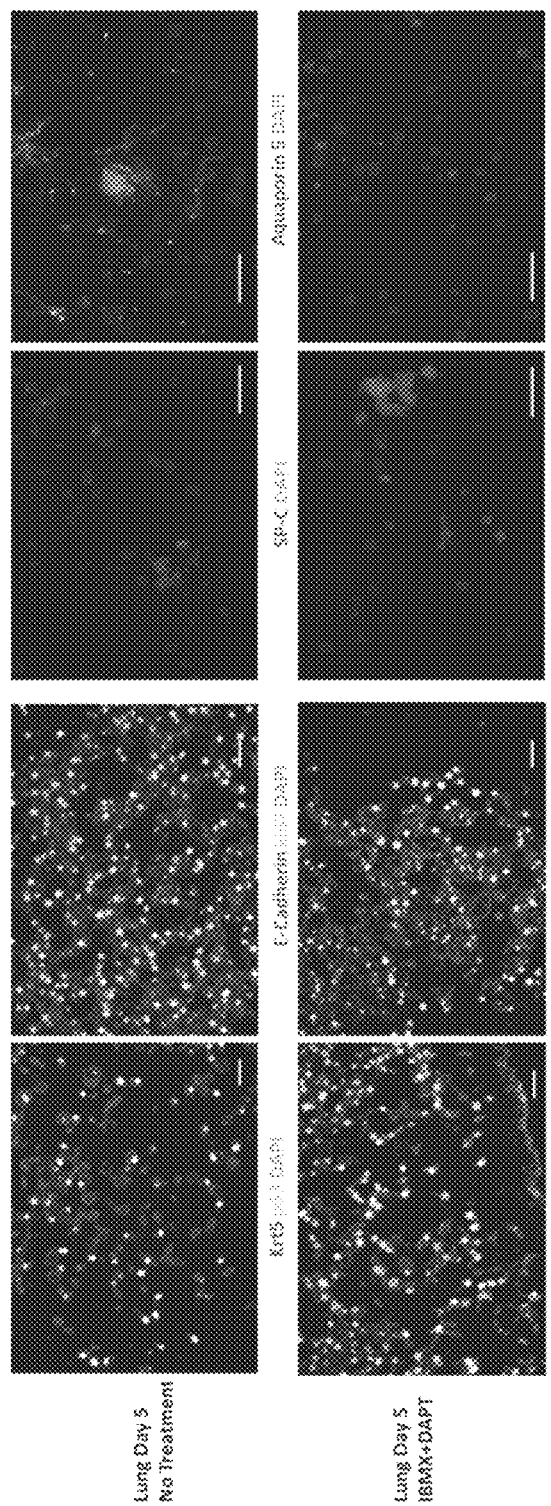

Cells seeded to human decellularized lung slices in vitro demonstrated specific cell attachment to the matrix via integrin α2β1 and α3β1, the formation of tight junctions along areas of matrix attachment (E-Cadherin), and continued global proliferation (Ki67⁺) (FIG. 4A). Gene expression following Notch inhibition was analyzed in cells seeded onto lung matrix from a neonatal donor (HL38, aged 3 days) and from a healthy adult lung (HL30) were analyzed. Induction of a type II pneumocyte population was found in both cultures treated with Notch inhibitors (FIG. 4B). Scaling-up to whole rodent lung re-epithelialization and culture (FIG. 4C), the transition toward a type II pneumocyte population was also demonstrated following 5 days of continuous media perfusion with Notch inhibitors vs lungs perfused with media alone (FIG. 4D-E).

Figure 5B:
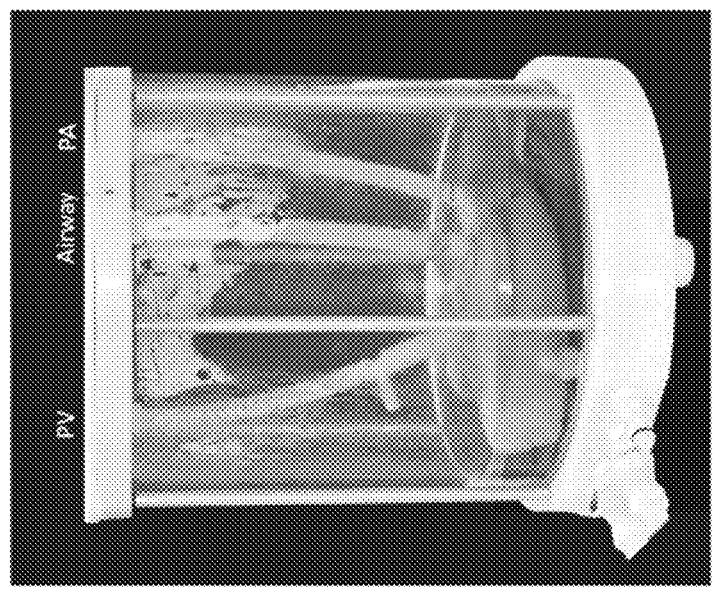
Figure 5A:
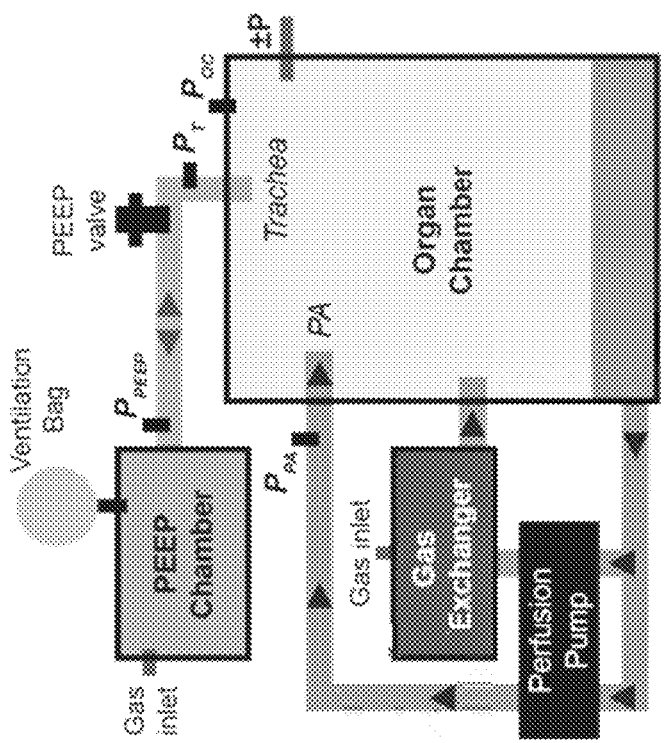
Figures 5J, 5K:
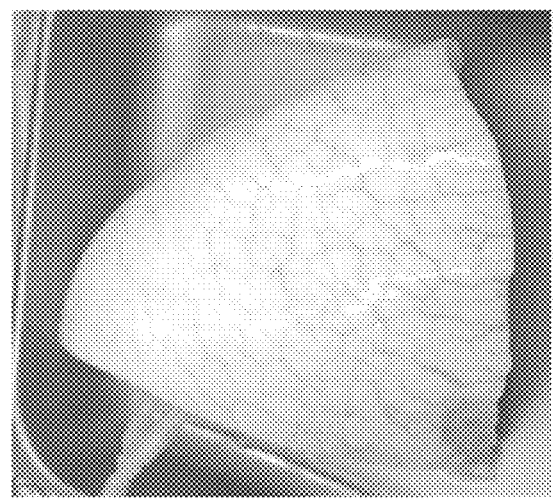

To enable large-scale whole organ culture, the present isolated lung bioreactor system was adapted for the recellularization of intact human lung scaffolds (55) (FIG. 5A). The expanded basal stem cell population was delivered to the airways of the human lung scaffold, and in addition, primary human lung-derived endothelial cells (CD31⁺) were delivered to the vascular compartment (FIG. 5B). The bioreactor maintained a physiologic perfusion range (mean=21.39±4.53 mmHg) of the ex vivo regenerating organ (FIG. 5C), while cell survival and metabolic activity were monitored in a non-invasive manner for 7-10 days. Increasing glucose consumption and lactic acid production in the perfusate was measured every 48 hours (FIG. 5D-E). Negative pressure ventilation of the lung construct was achieved at 6 breaths/minute by oscillating between set chamber pressure targets (FIG. 5F), resulting in a median peak trans-mural pressure of 15.88 mmHg (14.42-21.73 mmHg, n=2447 breaths), and a median tidal volume of 138.08 ml/breath (78.08-183.32 ml, n=2447 breaths) (FIG. 5G-I). Positive pressure ventilation was performed as an end-point test of potential organ function (FIG. 5J) and oxygenation transfer to the perfusate media was measured following ventilation at $FiO_2$ of 21% and 100% for 10 minutes. A resulting $pO_2$ of 72 mmHg ($PaO_2/FiO_2$=343 mmHg) was measured, which increased to 412 mmHg ($PaO_2/FiO_2$=412 mmHg), with a corresponding $pCO_2$ of 17.5 mmHg and 24.9 mmHg, respectively (FIG. 5K). This suggests that the regenerated human lung construct can support minimal organ function and gas transfer following recellularization and culture.

Figure 6C:
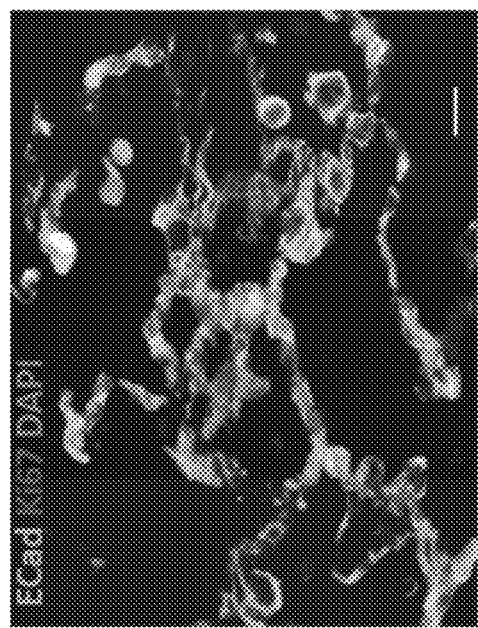
Figure 6D:
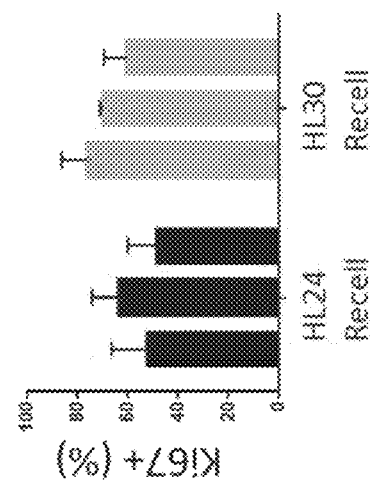
Figure 6E:
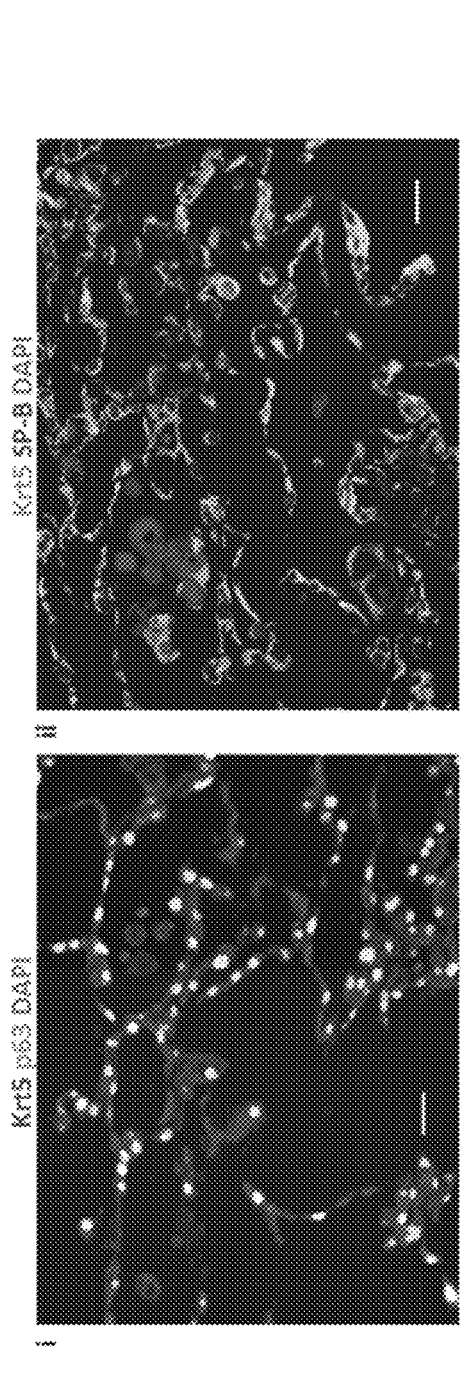
Figure 6F:
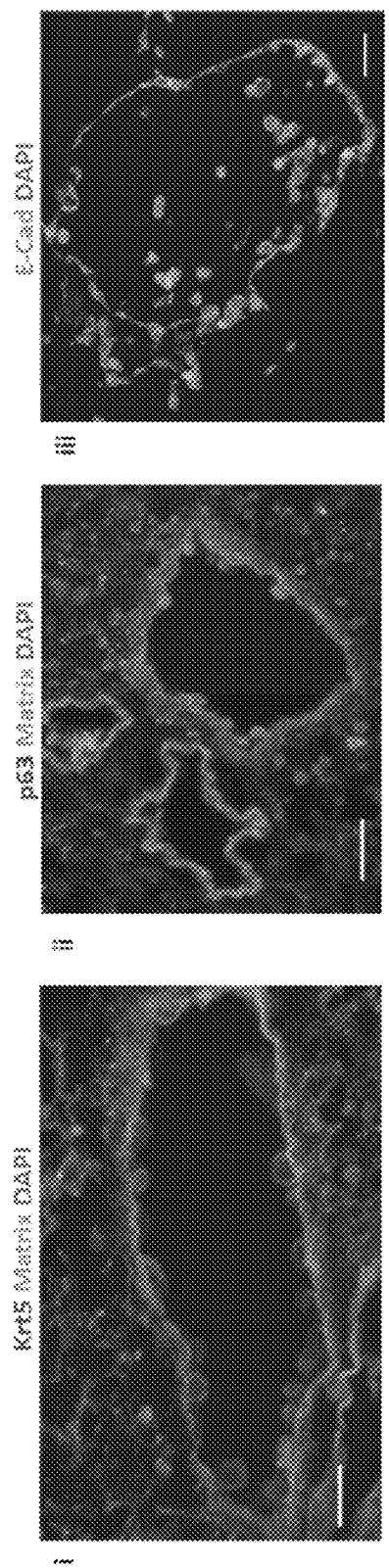
Figure 6G:
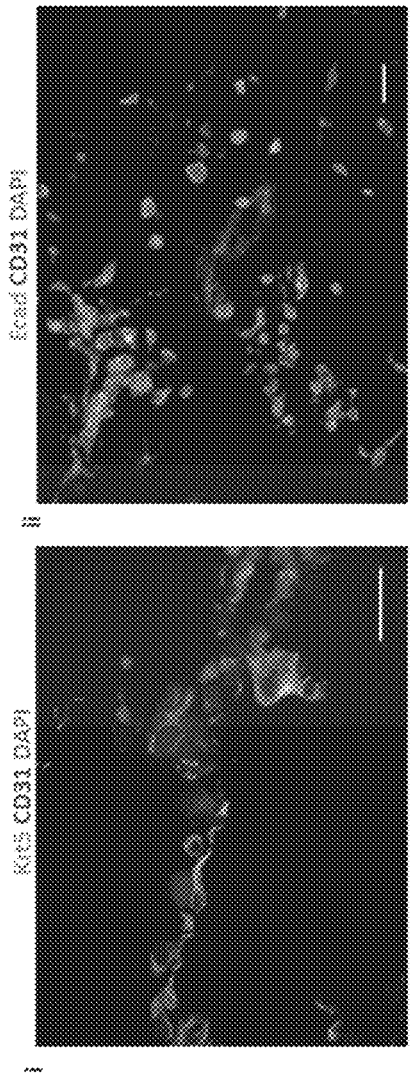
Figure 6H:
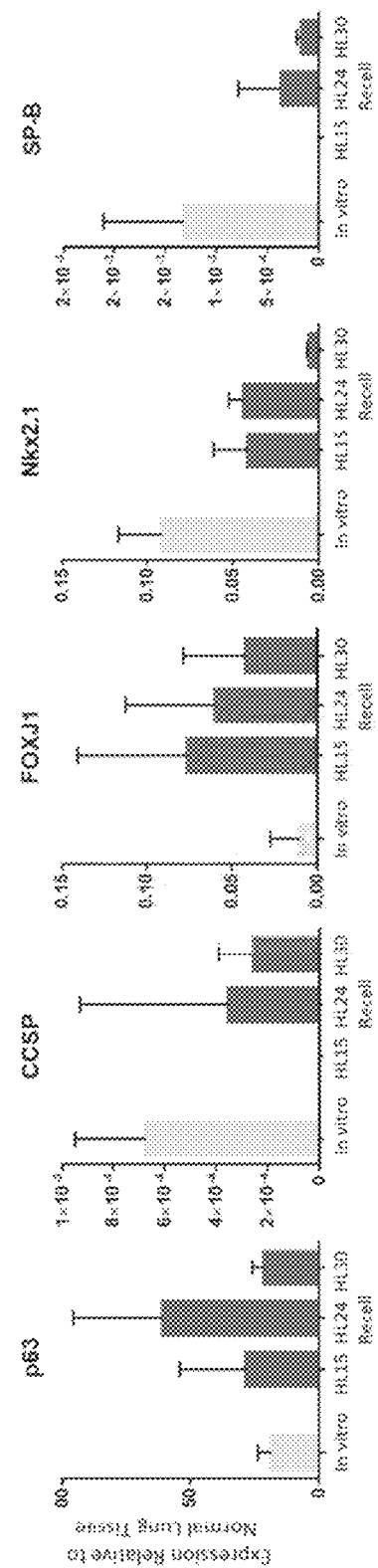
Figures 9A, 9B:
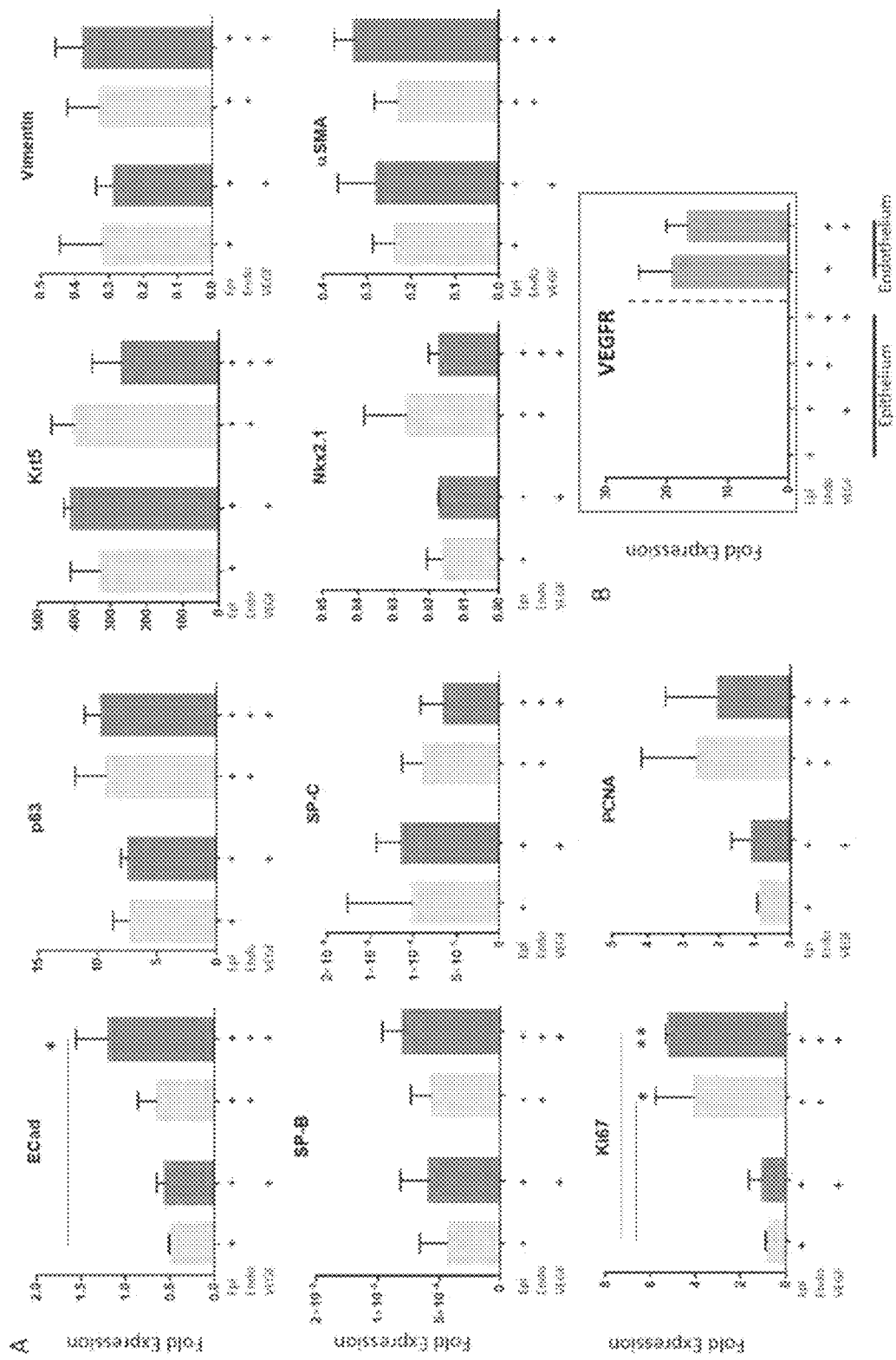
FIGS. 9A-B: Effect of Endothelium Cell Co-Culture on Basal Cell Population. (A) qPCR gene expression analysis of primary epithelial basal cells (passage 4) in co-culture with primary lung endothelial cells. Data represents the basal cell population (Epi+) plus the culture on endothelial cells on transwell inserts (Endo+), with or without the addition of VEGF in the culture media (VEGF+, 40/ml). (B) Expression of VEGF receptor by treated and untreated epithelium (undetected) and endothelium. Expression level is normalized to β-Actin and expressed relative to normal lung tissue. n=3 replicates analyzed in duplicate. Error bar=standard deviation. Analyzed by 1-way ANOVA with Dunnet post-test to Epi+ untreated group.

Tissue recellularization and cell viability was visually assessed following metabolism of Resazurin-containing perfusate, noting the metabolism to pink colour by viable cells (FIG. 6B). Extent of coverage and cell morphology was investigated by histologic staining across multiple areas of each lung (FIG. 6B). Broad cell distribution throughout the repopulated scaffold, from the upper airways to the distal lung region with cell alignment in accordance with the preserved matrix architecture was found. The ability of reintroduced cells to continue expansion within the matrix was confirmed. Up to 75% of cells were proliferating (61.7%±10.4) at the end of organ culture (FIG. 6C-D). Co-culture of the basal stem cell population with endothelial cells was found to increase epithelial proliferation in vitro (FIGS. 9A-B), which supports the effect in whole lung culture. A robust Krt5⁺p63⁺ basal stem cell phenotype was observed throughout the regenerated lung tissue (FIG. 6Ei), with a very minor contribution of non-adherent proSP-B⁺ cells identified (FIG. 6Eii). Epithelial cell attachment to large airways was also observed in both rat and lung whole lung culture (FIG. 6F). Heterogeneous endothelial cell coverage was observed throughout the vascular compartment, which corresponded with the expected distribution based on the initial cell number seeded. Rudimentary gas exchange units could be identified, represented by single layer endothelial and epithelial cells lining the alveolar-capillary interface (FIG. 6Gi) and repopulated vascular conduits were found (FIG. 6Gii). The epithelial cell population retained within the cultured lung was further analyzed for gene expression, confirming the maintenance of the basal stem cell population (p63 expression greater than 25-fold higher than normal cadaveric lung tissue), and very low expression levels of other mature lung epithelial lineages (CCSP, FOXJ1, Nkx2.1, and SP-B), relative to normal lung (FIG. 6H).

Figure 10A:
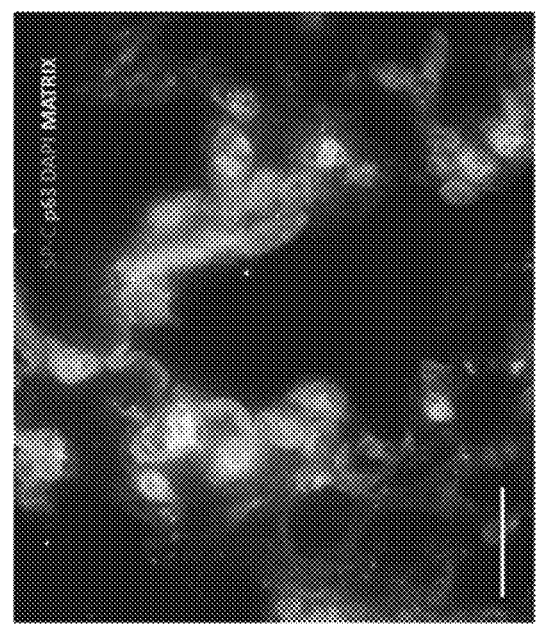
FIGS. 10A-B. BESCs were pre-treated with DAPT (50 nM) in vitro for 5 days, then delivered to rat lung scaffolds ($20 \times 10^6$), and maintained a distal type2-like fate, without continued inhibitor treatment. (A) Quantitative PCR analysis of gene expression at the end of in vitro treatment (Day 5), and following delivery to rat lung scaffold and ex vivo culture for 5 additional days without inhibitors. Data from 3 independent well (in vitro) or 3 independent tissue pieces (ex vivo) is shown. Expression normalized to β-actin and relative to normal cadaveric lung tissue control. (B) Immunofluorescent staining for surfactant protein C and p63, in recellularized lung tissue on day 5 of ex vivo culture. 50 um scale bar.
Figure 10B:
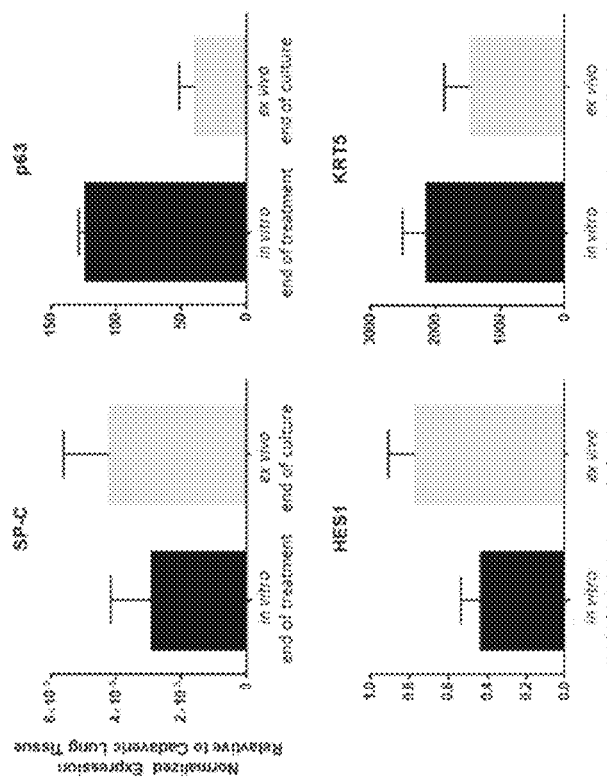

In addition, induction of a distal Type2 pneumocyte fate was confirmed following delivery of BESCs to the airways of acellular rat lung scaffolds and ex vivo biomimetic culture, with delivery of the inhibitors DAPT+IBMX through the vascular perfusate for 5 days (13.08±1. 15-fold increase in SP-C expression), see FIGS. 4A-B and E. BESCs could also be pre-differentiated in vitro prior to recellularization, and then shown to maintain a sustained distal fate after lung scaffold regeneration and inhibitor withdrawal, see FIG. 10A. Analysis of the regenerated lung tissue confirmed extensive alveolar recellularization with organized tissue architecture and morphology, see FIG. 10B.

Example 2. Enhanced Epithelial Regeneration on Native Human Scaffolds by Tenascin-C and Fibrillin-2

Typically, organ engineering based on native matrix scaffolds involves combining regenerative cell populations with corresponding biological matrices to form functional grafts on-demand. The extracellular matrix (ECM) that is retained following lung decellularization provides essential structure and biophysical cues for whole organ regeneration after recellularization. The unique ECM composition in the early post-natal lung, during active alveolargenesis, may possess distinct signals that can aid in driving cell adhesion, survival, and proliferation.

Methods

The following materials and methods were used in Example 2.

Study Approval.

Human donor lungs otherwise unsuitable for transplantation were obtained from the New England Organ Bank (see Table 1), following informed consent. Experiments were approved by the Massachusetts General Hospital Internal Review Board and Animal Utilization Protocol. Donor demographics are listed in Table 1.

TABLE 1

Donor demographics. Age in Day (D, neonatal) and Years (adult). Gestation listed in weeks (neonatal, not applicable (N/A) to adult donors). Gender listed as Male (M) or Female (F). Body Mass Index (BMI) listed for both group.

|  | Neonatal (n = 3) | | | Adult (n = 3) | | |
| --- | --- | --- | --- | --- | --- | --- |
| Age | 7 D | 2 D | 6 D | 48 | 64 | 47 |
| Gender | M | F | M | M | F | M |
| BMI | 11 | 9 | 14 | 24 | 48 | 21 |

Cell Isolation and Expansion.

Epithelial cells were isolated from adult donor lung peripheral tissue as described above, and maintained in vitro on human Collagen IV (Sigma-Aldrich, C7521)-coated flasks in Small Airway Growth Media (SAGM, Lonza, CC-3118) until used for experiments at passage 3.

Lung Decellularization.

Rat and human donor lungs were decellularized as previously described (Gilpin et al., The Journal of heart and lung transplantation: the official publication of the International Society for Heart Transplantation. 2014; 33(3):298-308; Guyette et al., Nature protocols. 2014; 9(6):1451-68). Briefly, cadaveric rat lungs were explanted from male Sprague-Dawley rats (250-300 g, >8 weeks of age, Charles River Laboratories) and decellularized by perfusion of 0.1% SDS solution through the pulmonary artery at 40 mmHg, followed by washing. Human lung decellularization was performed by perfusion of 0.5% SDS solution through the pulmonary artery at a constant pressure between 30 mmHg and 60 mmHg.

Lung ECM Digestion for In Vitro Coating and Culture.

Tissue samples from decellularized lungs (neonatal, n=3 and adult, n=3) were lyophilized and mechanically homogenized in pepsin buffer at (1 mg of pepsin per mL of 0.1 M sterile HCl) at 10 mg/mL for 24 h at room temperature. Before coating, pepsin digested tissue was diluted 1:100 in 0.1M acetic acid to a final conc. of 0.1 mg/mL. The coating was added to tissue culture plates and centrifuged at 300×g for 5 min. A total of 1×10$^6$ BESCs (identified by p63 and Krt5 expression) were added to each well of a 24-well plate, and cultured for 7 d in SAGM.

Cytotoxicity assay was performed in a 96-well plate, coated with ECM as described above, with a total of 1×10$^5$ BESCs added to each well. After 5 days of culture, Multi-Tox-Fluor Multiplex Cytotoxicity Assay (Promega) was performed per manufacturer's instructions, and live-cell fluorescence read at 400Ex/505Em; dead-cell fluorescence measured at 485Ex/520Em.

Proteomic Sample Preparation.

Decellularized neonatal and adult lung tissues were prepared for proteomic analyses as previously described (Li et al., Biomaterials. 2016; 75:37-46; Li et al. Biomaterials. 2016; 81:104-13). Approximately 90 mg of each tissue was minced on ice, and ground with disposable pellet pestles for 1 min in 1.5-mL tubes, followed by addition of 300 µL SDT solution—4% SDS, 0.1 M Tris-HCl (pH 7.6) and 0.1 M dithiothreitol (DTT) (all reagents from Sigma-Aldrich, St. Louis, Mo.). Samples were then heated at 95° C. for 7 min and sonicated on ice with a probe sonicator (Misonix XL2015, Misonix microtip PN/418, Farmingdale, N.Y.)— alternating 20 seconds on and 20 seconds off for 6 min, followed by centrifugation at 22° C. for 5 min at 16,100×g. Aliquots (2×30 µL) of the sample supernatant were mixed with 2×200 µL of 8M urea/0.1 M Tris buffer (pH 8.0) in a 30K MW Vivacon 500 filter (Sartorius, Bohemia, N.Y.). The sample was washed, alkylated with iodoacetamide, washed further, then digested with trypsin (Promega, Madison, Wis.; protein:enzyme ratio of 50:1 (w/w)) overnight at 37° C., and the digested peptides were collected by centrifugation. Digestion was then quenched with 10% trifluoroacetic acid (TFA) to a final concentration of 0.5% TFA.

The quenched digests were subjected to high pH fractionation on an HPLC system (Shimadzu, Columbia, Md.) using a Kinetex® C18 column (5 µm, 100 Å, 250×4.6 mm, Phenomenex, Torrance, Calif.). Mobile phase A was aqueous 20 mM ammonium formate and mobile phase B was 20 mM ammonium formate in 70% acetonitrile (ACN); the gradient of 0-100% mobile phase B occurred over 20 min. The HPLC flow rate was 1 mL/min and the eluent was collected and combined into 6 fractions, each of which was evaporated to dryness in the SpeedVac and reconstituted in 5% ACN, 2% formic acid (FA).

Proteomic Analysis with Liquid Chromatography-Tandem Mass Spectrometry (LC-MS/MS).

Reconstituted peptide solution was injected into a Waters nanoAcquity HPLC coupled to an ESI ion-trap/Orbitrap mass spectrometer (LTQ Orbitrap Velos, Thermo Scientific, Waltham, Mass.). Peptides were separated on a 100 µm inner diameter column packed with 20 cm of 1.7 μm BEH C18 particles (Waters, Milford, Mass.), and eluted at 0.3 μL/min in 0.1% FA with a gradient of increasing ACN over 2.5 h. A heater cartridge was used to keep the capillary column at 60° C. A full-mass scan (300-1500 m/z) was performed in the Orbitrap at a resolution of 60,000. The ten most intense peaks were selected for fragmentation by higher-energy collisional dissociation (HCD) at 42% collision energy, then analyzed with a resolution of 7,500 and an isolation width of 2.5 m/z. Dynamic exclusion was enabled with a repeat count of 1 over 30 s and an exclusion duration of 120 s.

Proteomic Data Analysis.

The acquired raw files were analyzed by MaxQuant version 1.5.2.8 (Cox et al., Nat Biotech. 2008; 26(12):1367-72). The UniProt database used contained 20,278 reviewed sequences from *Homo sapiens* downloaded on Dec. 5, 2013, supplemented with 262 common contaminants. Precursor and fragment ion mass tolerances were set to 4.5 ppm and 20 ppm, respectively. Static cysteine carbamidomethylation (+57.0215 Da) and up to 7 variable methionine and proline oxidations (+15.9949 Da) were specified. A false discovery rate of 1% at both the peptide and the protein level was allowed. Up to two missed cleavages were allowed and a minimum of two unique peptides per protein was required. Protein groups containing matches to proteins from the reversed database or contaminants were discarded. Only unique and razor peptides were used for quantification and a minimum count of two was required. Relative abundances of proteins within each sample were measured by intensity-based absolute quantification (iBAQ), and the label-free quantification (LFQ) algorithm embedded in the MaxQuant software package was employed for comparing the abundances of proteins between different samples. Perseus software (version 1.5.0.15) was used for downstream data processing. Proteins were filtered by requiring at least two valid values in at least one sample group (neonatal or adult). The corrected intensities were log 2 transformed and missing values were replaced using data imputation by employing a width of 0.3 and a downshift of 0.9. Two-sample t-tests with Benjamini-Hochberg correction were performed to statistically compare the LFQ values of individual proteins in the neonatal and adult tissues.

In Vitro Culture and Migration Assay.

24-well plates were pre-coated with human Collagen IV (10 μg/ml) Sigma-Aldrich C7521) for 2 h at 37° C. After removal of the collagen solution, TN-C (10 μg/ml, R&D 3358-TC-050) or the recombinant N-terminal half (FBN-2-N) or C-terminal half (FBN-2-C) of human FBN-2 (10 μg/ml) (Lin et al., The Journal of biological chemistry. 2002; 277(52):50795-804) were then added to select wells, and incubated for 2 h at 37° C. A total of $1 \times 10^5$ BESC were subsequently plated to each well and cultured for 7 d in SAGM.

For migration assay, after coating as above, a small inset (MIDI) was added to the wells prior to cell seeding. A total of $1 \times 10^4$ cells were seeded within the insert and incubated for 12 h, before the insert was removed. Bright-field images were taken every 30 min for 180 min to track cell migration. Images were analyzed with ImageJ software (Schneider et al., Nature methods. 2012; 9(7):671-5) to quantify the change in cell-free area.

Ex Vivo Rat Lung Recellularization and Culture.

Decellularized lung scaffolds were pre-coated with (A) PBS control, (B) TN-C, 10 μg/ml, (C) FBN-2, (10 μg/ml each of N- and C-terminal fragment of FBN-2), or (D) TN-C+FBN-2 (10 μg/ml each of TN-C and of N- and C-terminal fragment of FBN-2), by delivery through the trachea. Solution was recycled to the trachea for 90 min at 37° C. A total of $20 \times 10^6$ primary lung epithelial cells (passage 3) were then delivered to the scaffold airways in 20 ml of SAGM by gravity. Constant media perfusion of SAGM through the pulmonary artery was maintained at 4 ml/min (pressure 15-20 mmHg) and changed daily. Recellularized lungs were maintained in culture for 7 days, with the right lung removed on Day 3 for time point analysis.

Quantitative PCR.

mRNA was isolated (Qiagen RNeasy Plus Kit) and transcribed to cDNA (Invitrogen SuperScript III). Gene expression was analyzed using Taqman probes and the OneStep Plus system (Applied Biosystems). Each biological sample was analyzed in experimental replicate (n=2 repeated wells of the qPCR reaction) and the Ct value of each replicate was averaged and handed as n=1 unique biologic sample. Expression for each sample was normalized to β-Actin (ACTA1) gene expression (ΔCt) and relative to cadaveric peripheral lung tissue control samples (ΔΔCt), with fold change calculated by 2-ΔΔCt (Livak and Schmittgen, Methods. 2001; 25(4):402-8). A total of n=3 unique biological samples were analyzed for each reported experiment.

Immunostaining.

After de-paraffinization and rehydration, 5 μm tissue section were permeabilized with 0.1% Triton X-100 for intracellular antigens, when appropriate. Cells in culture were fixed with ice-cold methanol prior to staining. All samples were blocked with 1% donkey serum for 1 hour. Primary antibodies all 1:100 diluted: p63 (Biocare Medica, CM163A), Krt5 (Abcam, ab24647), E-cadherin (BD Biosciences, 610181), Ki67 (Abcam, ab16667). Secondary antibodies all 1:400 diluted: Donkey anti-Mouse, Rabbit, or Goat, conjugated to Alexa Fluor 488 or 594 (Life Technologies). Samples were stained with 4',6-diamidino-2-phenylindole (DAPI) to visualize the nucleus and imaged using a Nikon Ti-Eclipse microscope.

Figure 18:
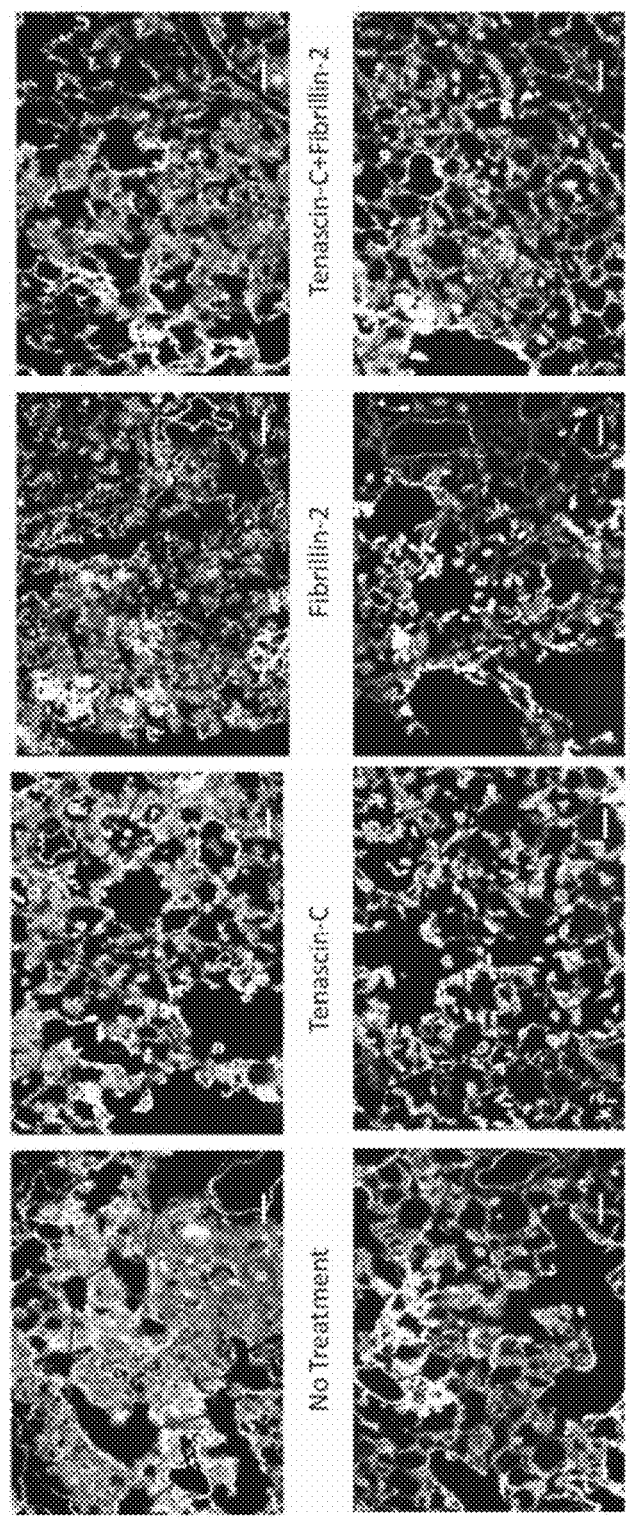
FIG. 18. Representative Measurement of Septal Thickness. Red lines indicate measured areas (n=5/image). Scale bar (white)=50 μm.

Image analysis was performed using ImageJ software (NIH), and septal thickness was measured on n=3 unique sections, with n=5 areas measured per section (see FIG. 18).

Statistical Analysis.

For all experiments, the n value stated represent an independent biological sample. Data were analyzed by 1-way or 2-way ANOVA, as appropriate, using GraphPad Software. All statistical significance is reported accordingly. *=p<0.05, =p<0.01, *=p<0.001.

Results

Figure 17A:
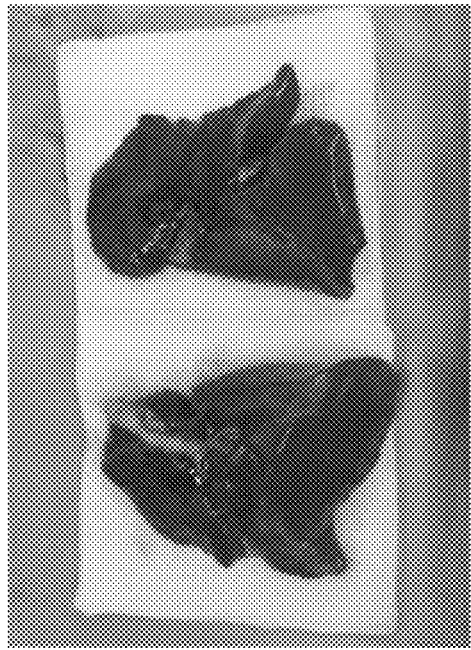
FIGS. 17A-C. Decellularization of Neonatal Human Lung. (A) Donor left and right Lung. (B) Cannulation of donor lungs. Scale bar=5 cm. (C) Decellularization of neonatal donor lung by perfusion decellularization of 0.5% Sodium Dodecyl Sulfate (SDS) solution.
Figure 17B:
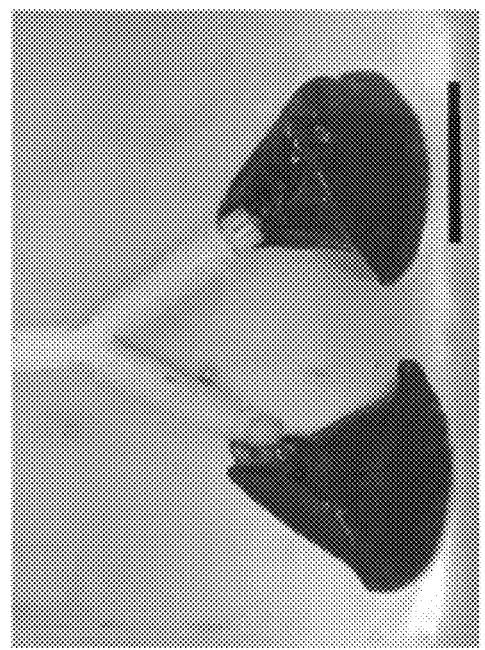
Figure 17C:
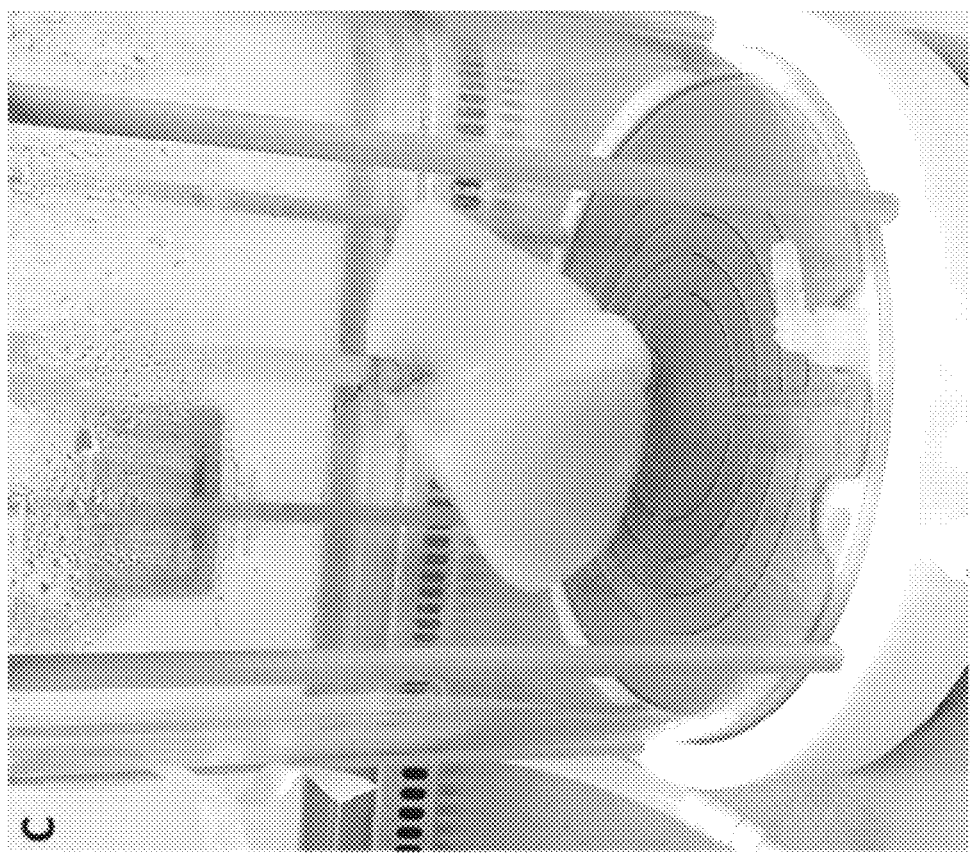

Donated human lungs deemed otherwise unsuitable for clinical transplantation were first decellularized by constant-pressure vascular perfusion of 0.5% sodium dodecyl sulfate (SDS) solution (see FIGS. 17A-B), followed by extensive washing to remove residual detergent and cellular components, to generate an extracellular matrix protein scaffold (previously described in Gilpin et al., The Journal of heart and lung transplantation: the official publication of the International Society for Heart Transplantation. 2014; 33(3): 298-308; Guyette et al., Nature protocols. 2014; 9(6):1451-68). A total of n=3 neonatal (less than 1 week of life) lung scaffolds and n=3 adult lung scaffolds were prepared in this manner for subsequent analyses (See Table 1).

Figure 12A:
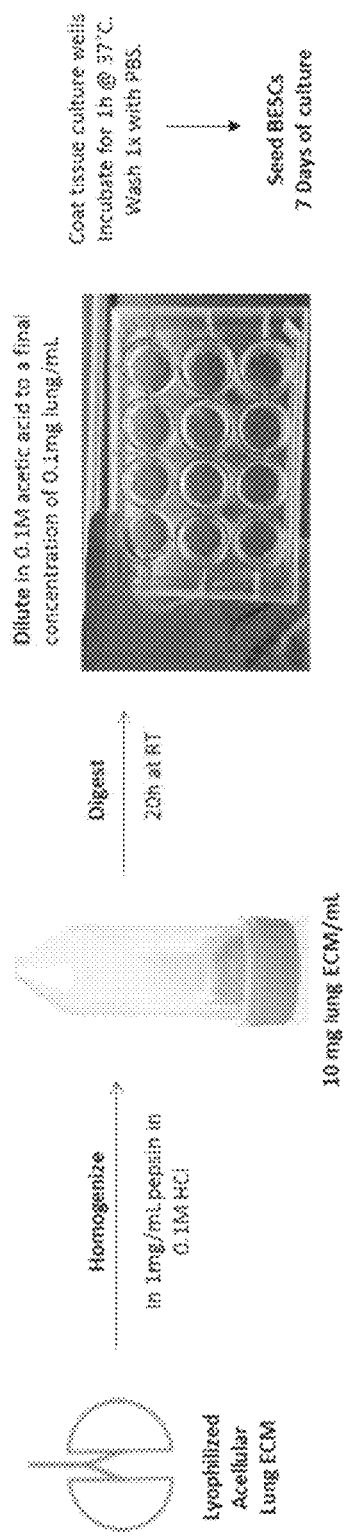
FIGS. 12A-C. Epithelial Culture on Isolated Human ECM. (A) Method for preparation of matrix coating for in vitro culture. (B) Quantitative gene expression analysis of BESCs grown on neonatal (N1-N3) and adult (A1-A3) matrix coating. Expression normalized to B-Actin, and expressed relative to normal adult lung tissue. (C) Cytotoxicity assay measuring total live and dead cell fluorescence on Day 7.
Figure 12B:
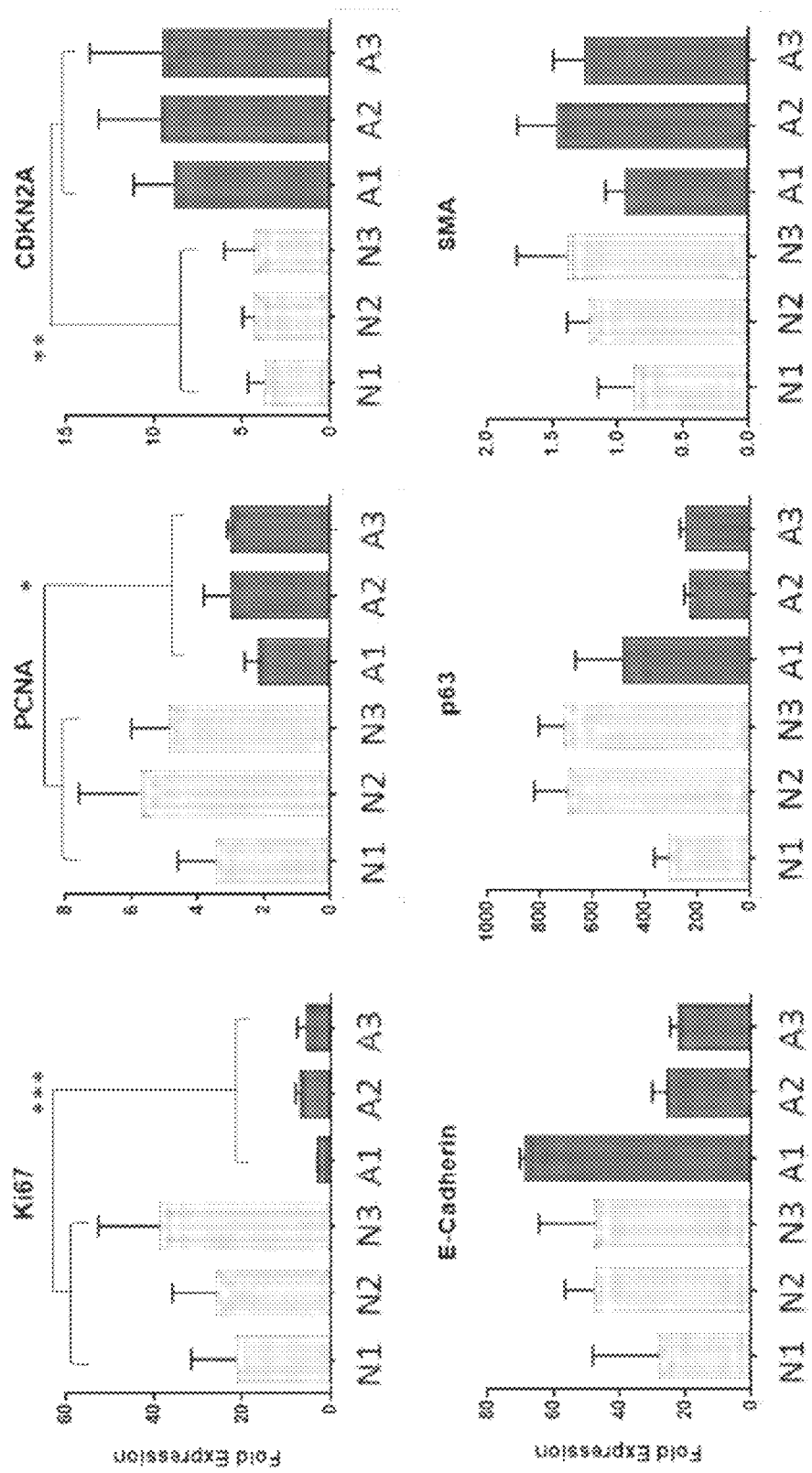
Figure 12C:
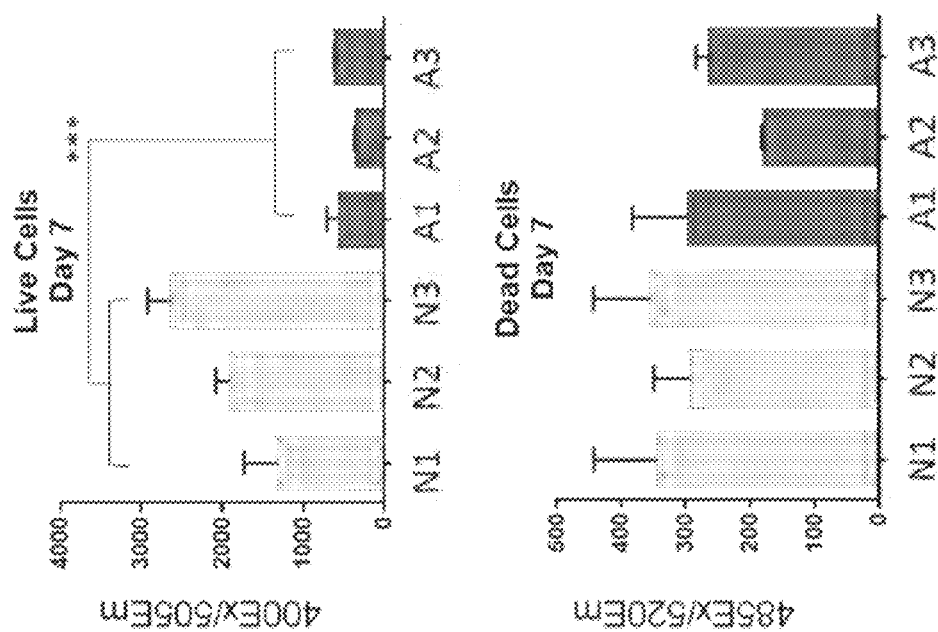

We first aimed to evaluate the response of primary donor tissue-derived basal epithelial stem cells (BESCs) when cultured on ECM derived from neonatal versus adult lungs. To this end, acellular lung ECM from each neonatal and adult donor was prepared as a coating for in vitro epithelial cell culture (FIG. 12A). After culture of BESCs on each substrate for 7 d, it was found that cells on neonatal ECM were significantly more proliferative (Ki67 and PCNA expression), and less senescent (CDKN2A expression) compared to cells grown on adult lung ECM (FIG. 12B). No significant differences in epithelial phenotype were found (E-Cadherin, p63 expression), and no increase in expression of the mesenchymal marker smooth muscle actin (SMA) was observed. By total cell assessment, significantly more live cells engrafted on neonatal ECM coating than on adult lung ECM, by 7 d of culture, while no difference in the number of dead cells was found (FIG. 12C).

Figure 13A:
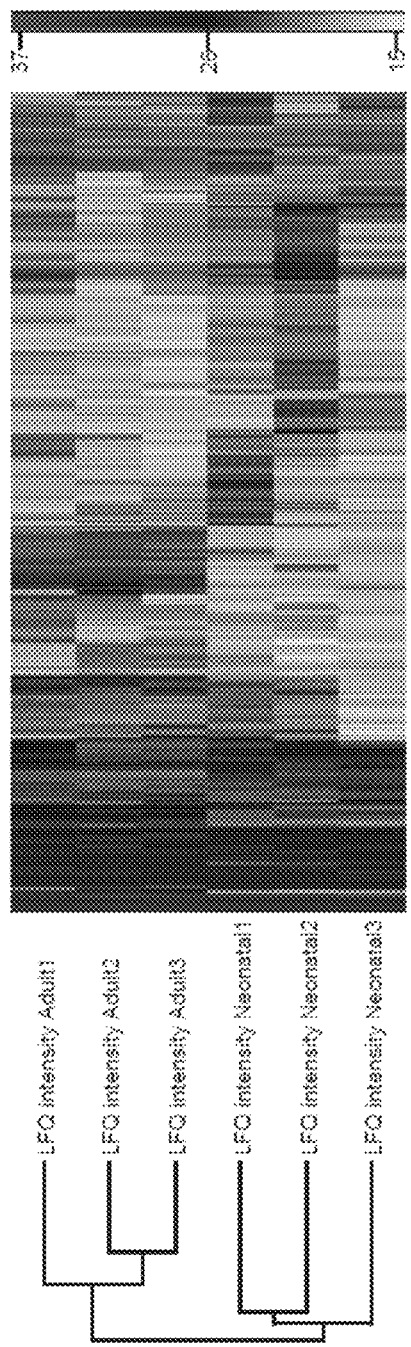
FIGS. 13A-B. Neonatal and Adult Lung Composition by Proteomic Analysis. (A) Heat map of detected proteins in each sample. (B) Summary matrisome composition in neonatal vs adult matrix (n=3/group).
Figure 13B:
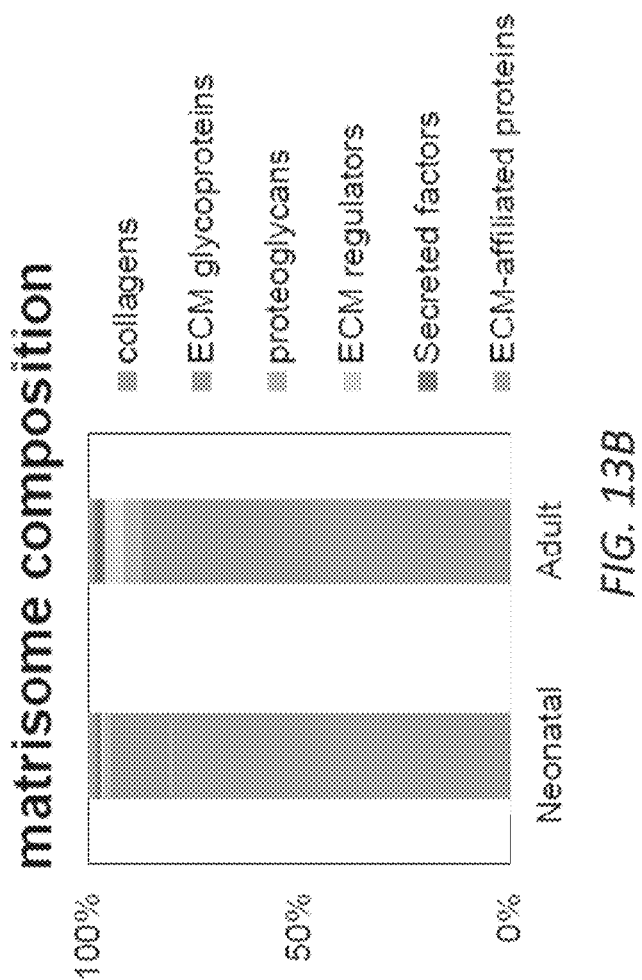

To then investigate the difference in protein composition that may be mediating this effect, we evaluated acellular lung scaffolds from neonatal versus adult donor lungs by proteomic analysis with liquid chromatography-tandem mass spectrometry (LC-MS/MS). The heat map in FIG. 13A shows the change in abundance of each protein, from each biological sample. In both groups, many low-abundance proteins were measured (green), in addition to a smaller number of high-abundance proteins (red). Further analysis of the subcategories of the matrisome (FIG. 13B) showed that neonatal lung scaffolds contained a larger number of collagens, while the other subcategories (glycoproteins, proteoglycans, ECM regulators, etc.) are more abundant in the adult scaffolds.

Figure 14A:
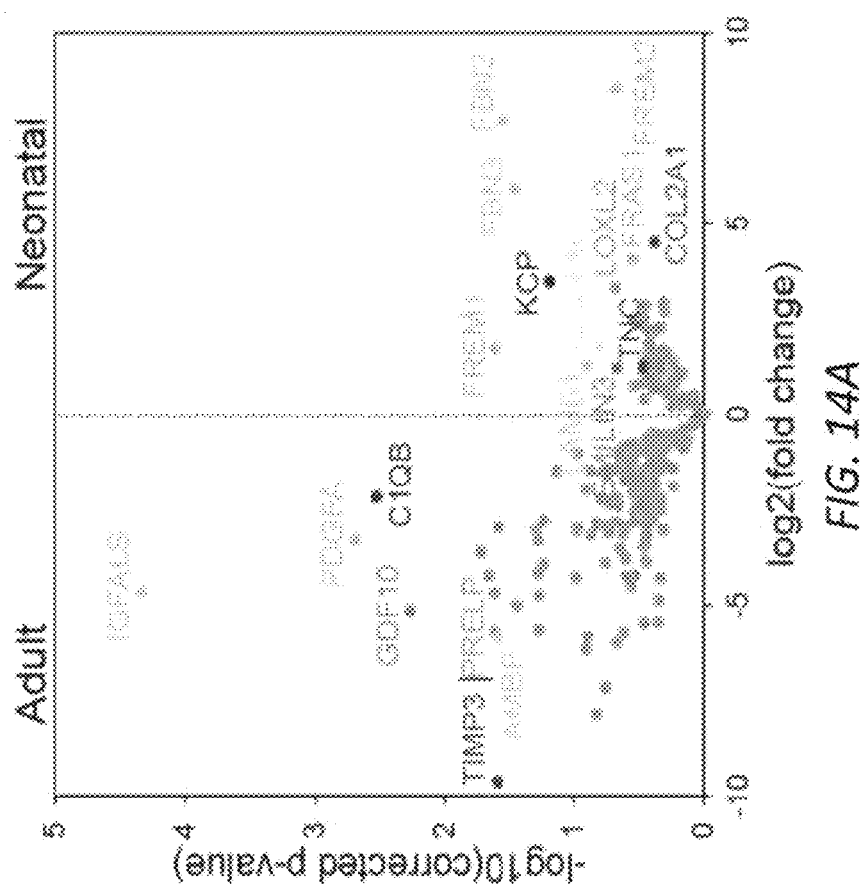

The measured abundance of each individual matrix protein was then compared in the neonatal versus adult scaffolds. A volcano plot was generated, showing fold change in protein abundance (adult versus neonatal) plotted against statistical p-values. Selected proteins that are enriched in neonatal or adult scaffolds are highlighted in FIG. 14A and listed with details in FIG. 14B.

Fibrillin 2 and 3 were found to be enriched in the neonatal scaffold, relative to the adult samples (Fibrillin-2=202.74-fold change, $p=2.8 \times 10^{-2}$). Fibrillins are glycoproteins that are essential for the deposition of elastin and the formation of elastic fibers, which supports alveolar development and structure (Peirce et al., Ciba Foundation symposium. 1995; 192(199-212; discussion -4). Specifically, the expression pattern of FBN-2 is largely restricted to developing fetal tissues (Zhang et al., The Journal of cell biology. 1994; 124(5):855-6). In addition, FBN-2 has been shown to interact with TN-C, both in development and in tissue repair (Brinckmann et al., Laboratory investigation; a journal of technical methods and pathology. 2010; 90(5):739-52). TN-C is also found in the post-natal lung ECM and has been shown to aid the process of branching morphogenesis (Young et al., Developmental biology. 1994; 161(2):615-25). Enrichment of these two proteins in the neonatal lung scaffolds prompted us to further analyze their role as potential mediators of the enhanced epithelial repair response found on neonatal lung ECM coating.

Figure 15A:
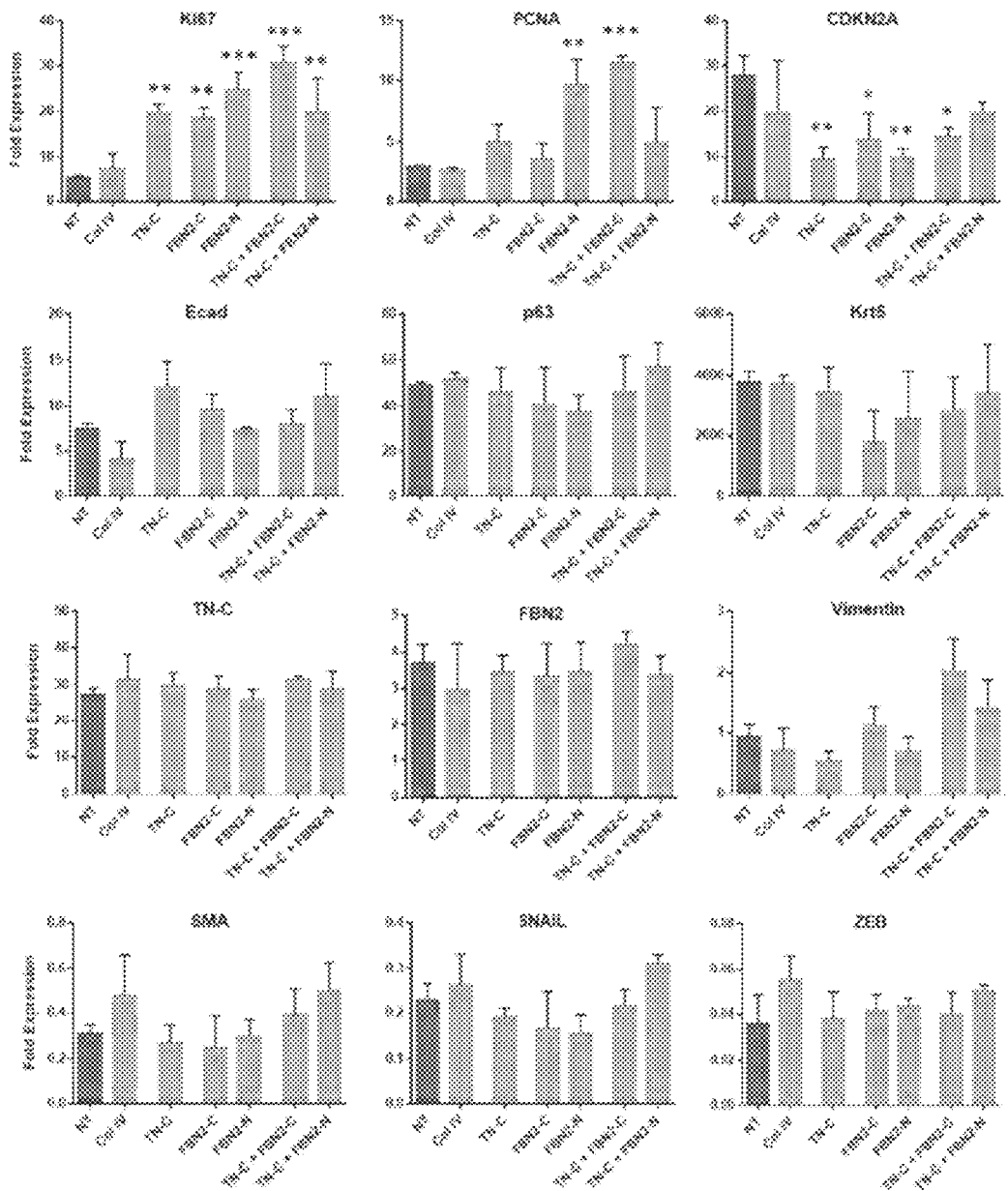
Figure 15C:
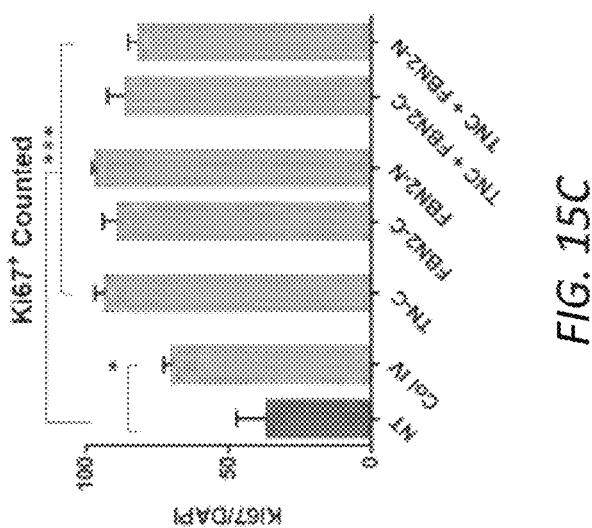
Figures 15D, 15E:
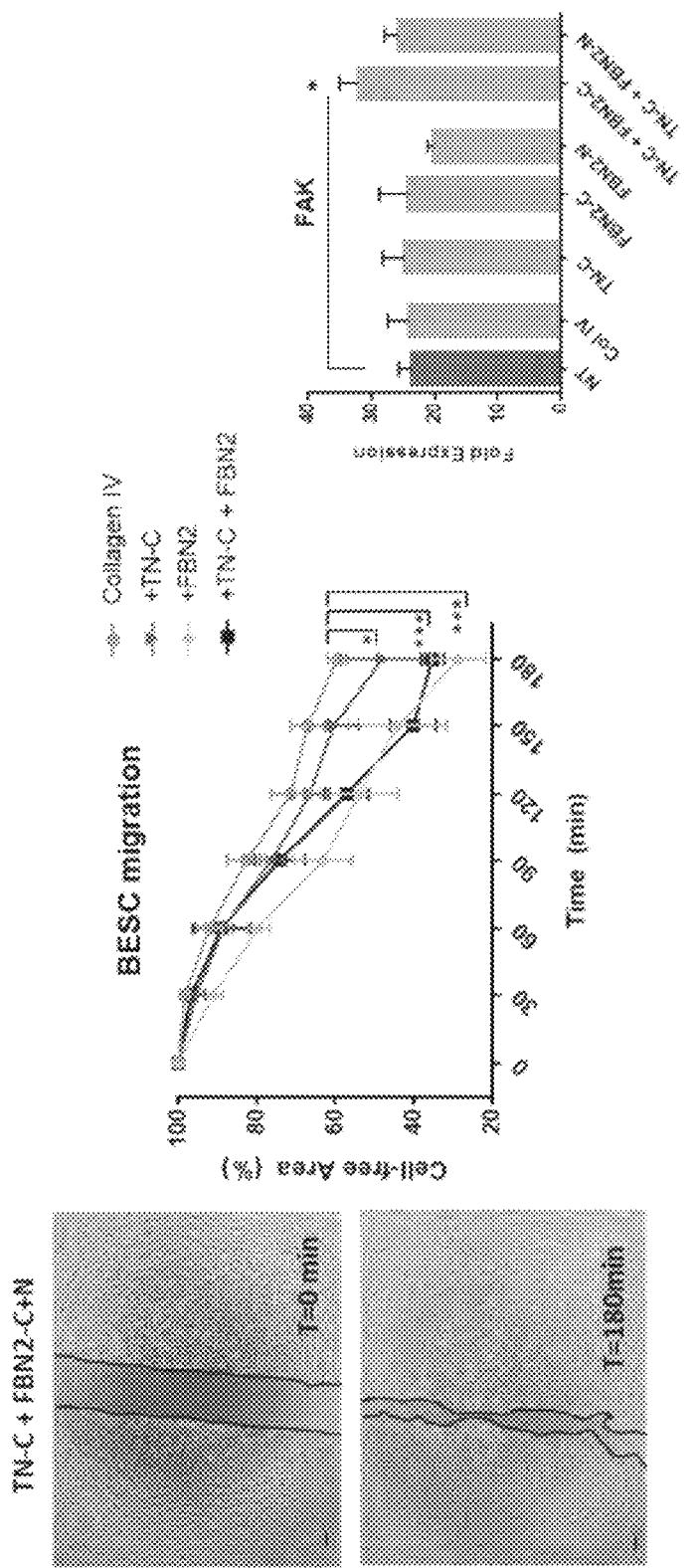

We tested if these individual proteins could recapitulate the beneficial effects of neonatal ECM on BESC in vitro. BESCs were cultured on plates first coated with Collagen IV, and then supplemented with TN-C and/or FBN-2 recombinant N- and C-terminal halves, and compared this to culture on uncoated wells (FIG. 15A). As observed when BESC were cultured on isolated neonatal ECM coating, we found significantly greater proliferation and less senescence by BESCs grown on FBN-2 and TN-C coated plates, with the most significant response measured on TN-C+FBN-2-C-terminal half coating. No differences in epithelial phenotype was found, when compared to uncoated or Collagen IV coated wells. No significant changes in TN-C, FBN-2, or Vimentin expression was detected in response to the different protein coatings (FIG. 15A). Also, no evidence of epithelial-to-mesenchymal transition (EMT) was identified on the different coatings, as assessed by smooth muscle actin (SMA) expression and the transcription factors SNAIL and ZEB (FIG. 15A). Immunofluorescent staining of BESCs grown the different ECM coatings confirmed the findings of the gene expression analysis, and when Ki67 expression was quantified, a significant difference was found on FBN-2 and TN-C coated plates (FIGS. 15B-C). BESC migration was also investigated on the various protein coatings, by quantifying the cell migration assay. A mixture of the N- and C-terminal halves of FBN-2 was used for the migration assay. Significantly higher rates of BESC migration were identified on FBN-2 and TN-C coated plates over 3 h, when compared to Collagen IV coating alone (p<0.001, FIG. 15D). In addition, gene expression of Focal Adhesion Kinase (FAK), an additional indicator of cell migration (Mitra et al., Nature reviews Molecular cell biology. 2005; 6(1):56-6), was measured on the various coatings, with a significantly higher expression level in BESC grown on TN-C+FBN-2 C-terminal fragment coated plates (FIG. 15E).

To ultimately assess these findings in the context of whole lung epithelial tissue regeneration, we evaluated the effect of FBN-2 (mixed N and C-terminal fragment) and TN-C pretreatment of the acellular lung scaffold prior to epithelial recellularization. After pre-coating and BESC re-epithelialization, the lungs were maintained in ex vivo biomimetic culture for 7 d, with the right lung removed on Day 3 for time-point analysis.

Figure 16A:
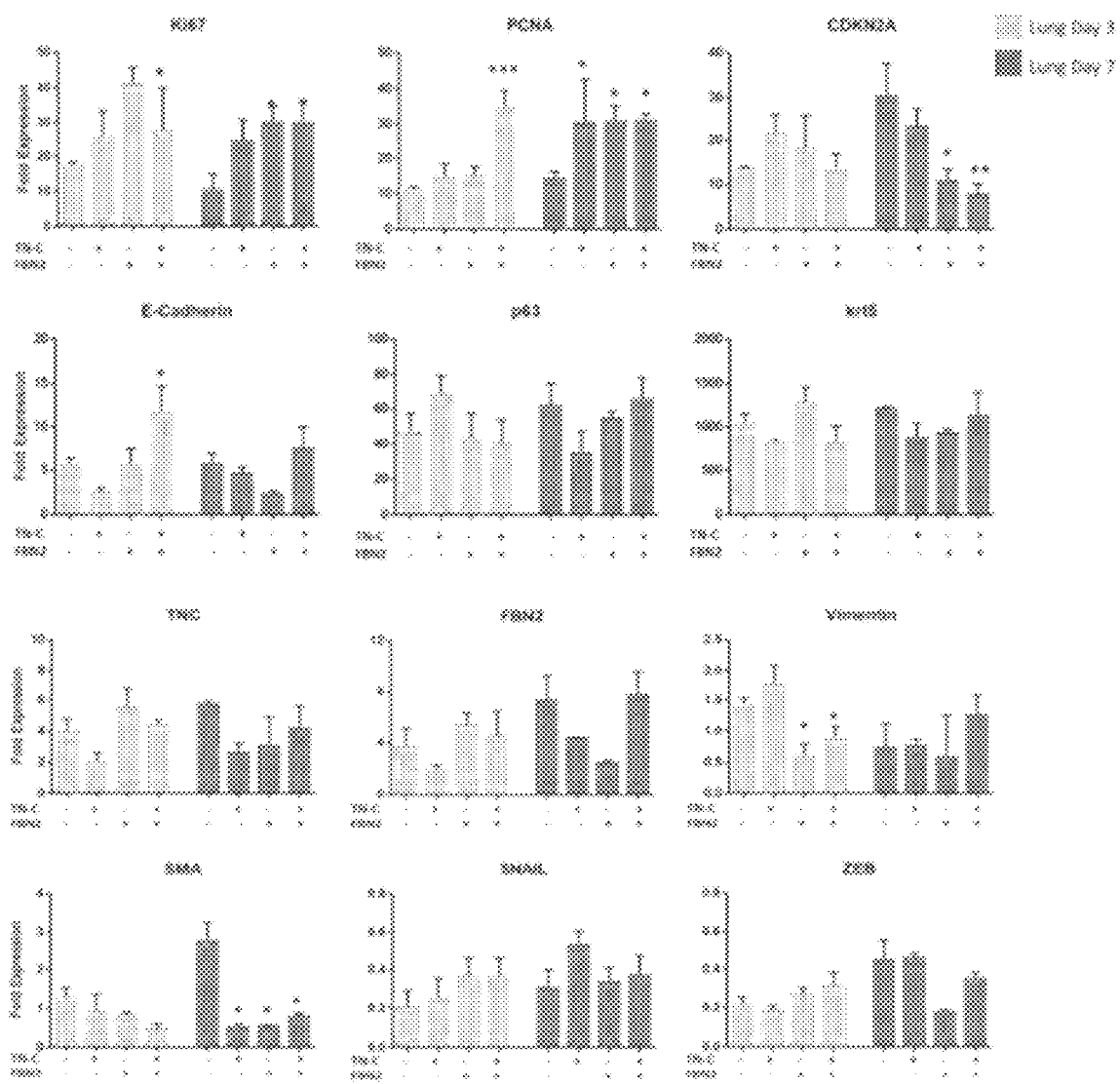
FIGS. 16A-E. Ex vivo lung epithelial regeneration on pre-treated matrices. (A) Quantitative gene expression of re-epithelialized lung scaffolds (B) Hematoxylin and eosin assessment of lung tissue. Scale bar=50 μm. (C) Immunofluorescent staining of lung tissue on Day 3 and 7 of regeneration. Scale bar=50 μm. (D) Quantification of Ki67 positive cells on Day 3 and 7 of lung epithelial regeneration. (E) Quantification of tissue morphology by septal thickness.
Figure 16B:
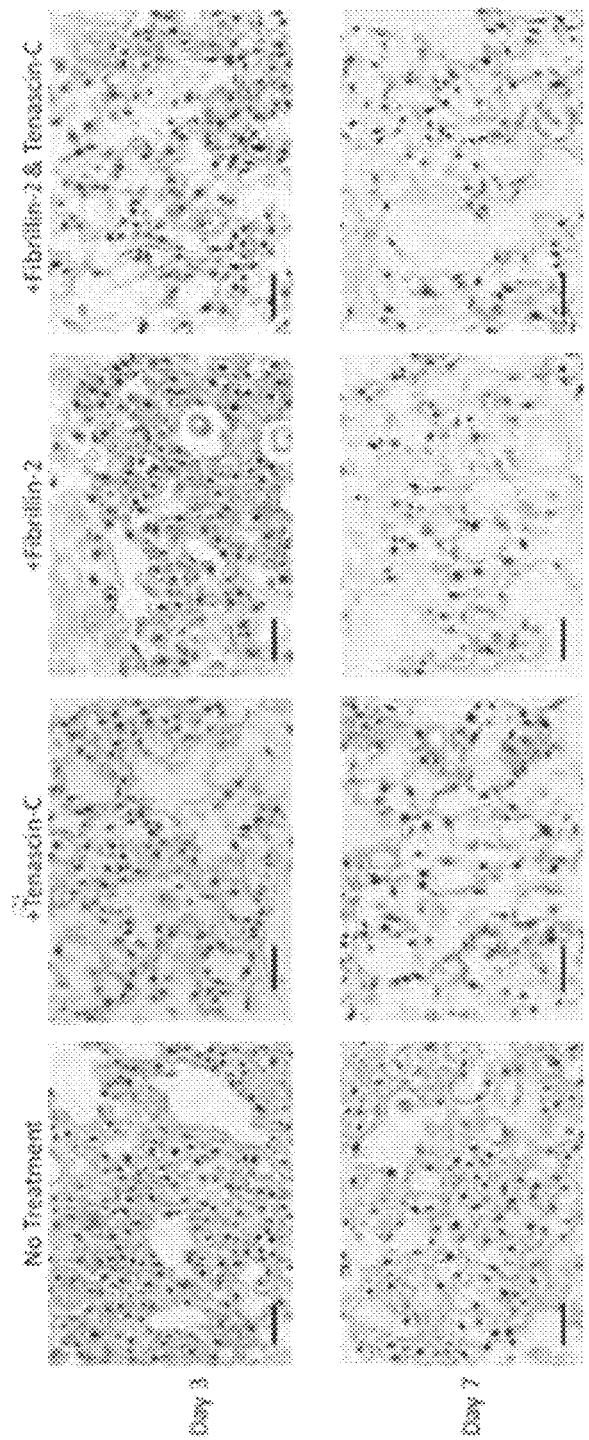

Tissue analysis again identified significantly more epithelial proliferation, on both Day 3 and 7 of regeneration, with scaffold pre-treatment (FIG. 16A). The increase in cellular senescence on Day 7 of culture was significantly reduced by FBN-2+TN-C scaffold coating. An increase in E-Cadherin expression was measured on Day 3 following FBN-2+TN-C treatment, but otherwise epithelial fate was unchanged by scaffold coating. Neither FBN-2 nor TN-C were upregulated by the treatment. No increase in mesenchymal phenotype or EMT-associated transcription factor expression was noted. Gross morphologic analysis of the re-epithelialized lung tissue by hematoxylin and eosin staining revealed improved tissue structure, cell alignment to the matrix, and less cell hypertrophy in the coated lungs, when compared to untreated (FIG. 16B). These observations were most apparent at Day 7 of culture.

Figure 16C:
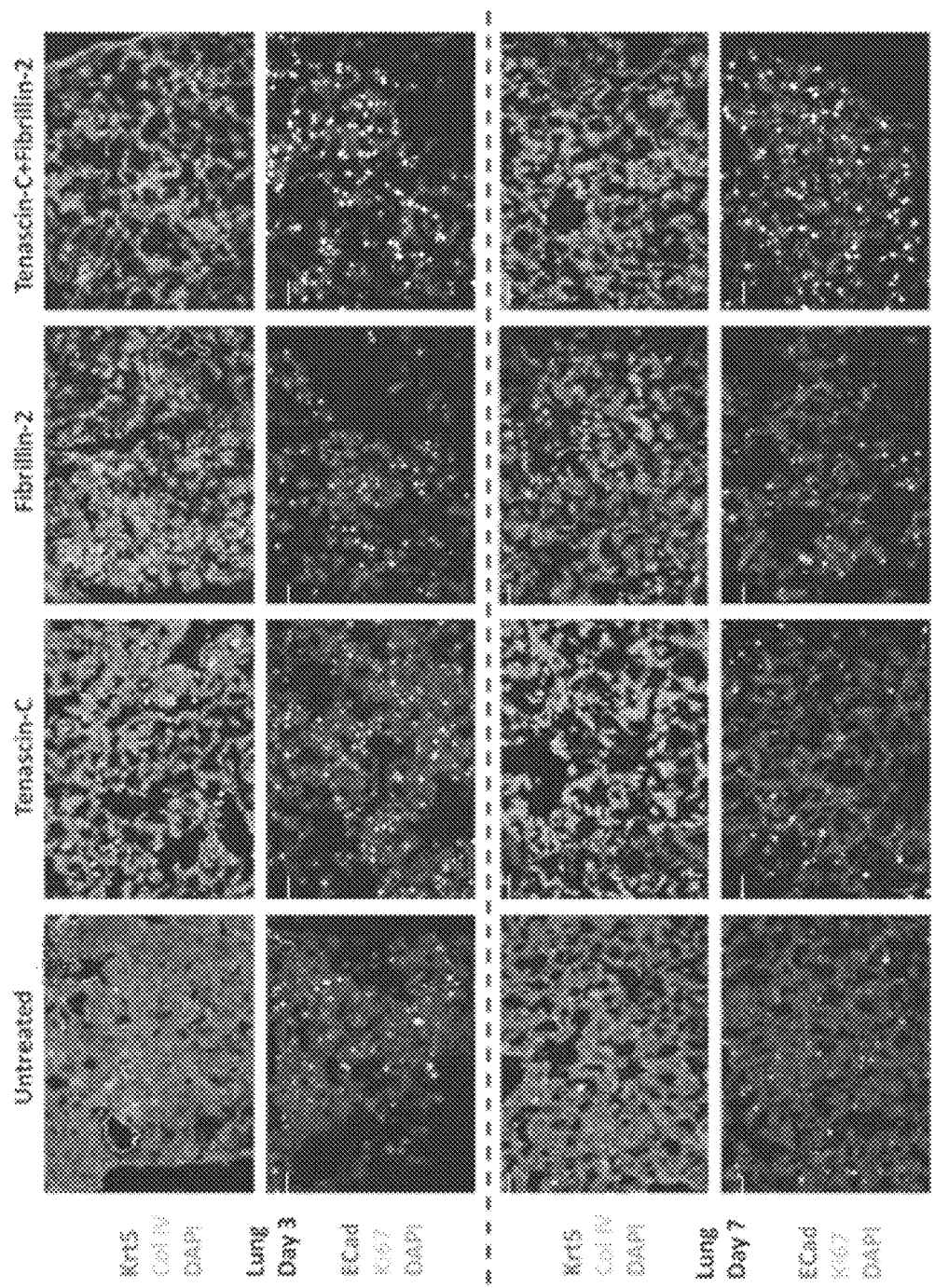

Immunofluorescent staining was performed to assess epithelial fate and proliferation. Quantification of Ki67 expression of Krt5+ BESCs confirmed a significant increase in proliferation when lung scaffolds were pre-coated with FBN-2 and TN-C, with the greatest cellular response found when both proteins were combined for scaffold coating (FIGS. 16C-D).

Figure 16E:
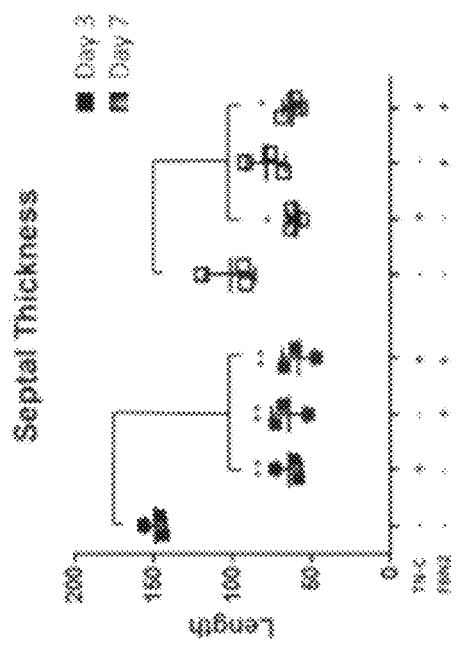
Figure 16D:
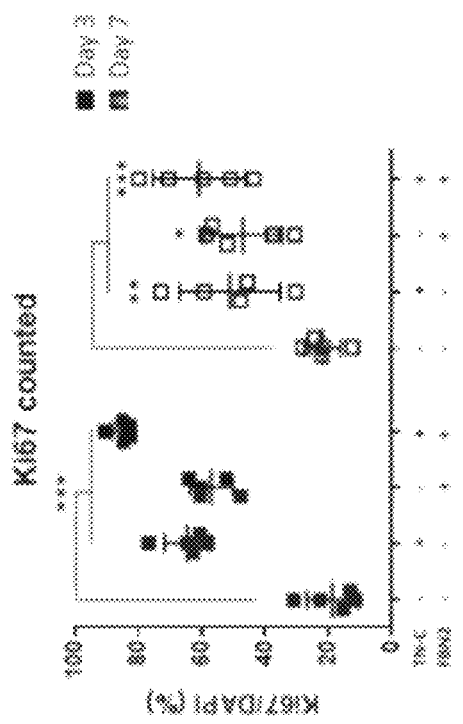

Quantification of tissue morphology by measurement of septal thickness, also confirmed the observation that pre-coating of the scaffolds resulted in more cell alignment and less septal thickening in the regenerated lung tissue (FIG. 16E and FIG. 18). This resulted in an alveolar structure with an appearance more similar to native lung tissue, in both size and structure.

Together, these results demonstrate that the treatment of acellular lung matrices with FBN-2 and TN-C proteins can enhance basal epithelial stem cell migration, proliferation, and aid lung tissue repair.

REFERENCES

1. Badylak S F, Taylor D, Uygun K. Whole-organ tissue engineering: decellularization and recellularization of 1. three-dimensional matrix scaffolds. Annual review of biomedical engineering 2011; 13: 27-53.
2. Guyette J P, Gilpin S E, Charest J M, Tapias L F, Ren X, Ott H C. Perfusion decellularization of whole organs. Nature protocols 2014; 9: 1451-1468.
3. Ott H C, Matthiesen T S, Goh S K, Black L D, Kren S M, Netoff T I, Taylor D A. Perfusion-decellularized matrix: using nature's platform to engineer a bioartificial heart. Nature medicine 2008; 14: 213-221.
4. Ott H C, Clippinger B, Conrad C, Schuetz C, Pomerantseva I, Ikonomou L, Kotton D, Vacanti J P. Regeneration and orthotopic transplantation of a bioartificial lung. Nature medicine 2010; 16: 927-933.
5. Petersen T H, Calle E A, Zhao L, Lee E J, Gui L, Raredon M B, Gavrilov K, Yi T, Zhuang Z W, Breuer C, Herzog E, Niklason L E. Tissue-engineered lungs for in vivo implantation. Science 2010; 329: 538-541.
6. Gilpin S E, Guyette J P, Gonzalez G, Ren X, Asara J M, Mathisen D J, Vacanti J P, Ott H C. Perfusion decellularization of human and porcine lungs: bringing the matrix to clinical scale. J Heart Lung Transplant 2014; 33: 298-308.
7. Wagner D E, Bonenfant N R, Parsons C S, Sokocevic D, Brooks E M, Borg Z D, Lathrop M J, Wallis J D, Daly A B, Lam Y W, Deng B, DeSarno M J, Ashikaga T, Loi R, Weiss D J. Comparative decellularization and recellularization of normal versus emphysematous human lungs. Biomaterials 2014; 35: 3281-3297.
8. Gilpin S E, Ott H C. Using Nature's Platform to Engineer Bio-Artificial Lungs. Annals of the American Thoracic Society 2015; 12 Suppl 1: S45-49.
9. Longmire T A, Ikonomou L, Hawkins F, Christodoulou C, Cao Y, Jean J C, Kwok L W, Mou H, Rajagopal J, Shen S S, Dowton A A, Serra M, Weiss D J, Green M D, Snoeck H W, Ramirez M I, Kotton D N. Efficient derivation of purified lung and thyroid progenitors from embryonic stem cells. Cell stem cell 2012; 10: 398-411.
10. Mou H, Zhao R, Sherwood R, Ahfeldt T, Lapey A, Wain J, Sicilian L, Izvolsky K, Musunuru K, Cowan C, Rajagopal J. Generation of multipotent lung and airway progenitors from mouse ESCs and patient-specific cystic fibrosis iPSCs. Cell stem cell 2012; 10: 385-397.
11. Huang S X, Green M D, de Carvalho A T, Mumau M, Chen Y W, D'Souza S L, Snoeck H W. The in vitro generation of lung and airway progenitor cells from human pluripotent stem cells. Nature protocols 2015; 10: 413-425.
12. Kotton D N, Morrisey E E. Lung regeneration: mechanisms, applications and emerging stem cell populations. Nature medicine 2014; 20: 822-832.
13. Rock J R, Randell S H, Hogan B L. Airway basal stem cells: a perspective on their roles in epithelial homeostasis and remodeling. Disease models & mechanisms 2010; 3: 545-556.
14. Rawlins E L, Hogan B L. Epithelial stem cells of the lung: privileged few or opportunities for many? Development 2006; 133: 2455-2465.
15. Mercer R R, Russell M L, Roggli V L, Crapo J D. Cell number and distribution in human and rat airways. American journal of respiratory cell and molecular biology 1994; 10: 613-624.
16. Inayama Y, Hook G E, Brody A R, Cameron G S, Jetten A M, Gilmore L B, Gray T, Nettesheim P. The differentiation potential of tracheal basal cells. Laboratory investigation; a journal of technical methods and pathology 1988; 58: 706-717.
17. Rock J R, Onaitis M W, Rawlins E L, Lu Y, Clark C P, Xue Y, Randell S H, Hogan B L. Basal cells as stem cells of the mouse trachea and human airway epithelium. Proceedings of the National Academy of Sciences of the United States of America 2009; 106: 12771-12775.
18. Hackett N R, Shaykhiev R, Walters M S, Wang R, Zwick R K, Ferris B, Witover B, Salit J, Crystal R G. The human airway epithelial basal cell transcriptome. PloS one 2011; 6: e18378.
19. Davidson D J, Gray M A, Kilanowski F M, Tarran R, Randell S H, Sheppard D N, Argent B E, Dorin J R. Murine epithelial cells: isolation and culture. Journal of cystic fibrosis: official journal of the European Cystic Fibrosis Society 2004; 3 Suppl 2: 59-62.
20. Fulcher M L, Randell S H. Human nasal and tracheobronchial respiratory epithelial cell culture. Methods in molecular biology 2013; 945: 109-121.
21. Hong K U, Reynolds S D, Watkins S, Fuchs E, Stripp B R. In vivo differentiation potential of tracheal basal cells: evidence for multipotent and unipotent subpopulations. American journal of physiology Lung cellular and molecular physiology 2004; 286: L643-649.
22. Evans M J, Shami S G, Cabral-Anderson L J, Dekker N P. Role of nonciliated cells in renewal of the bronchial epithelium of rats exposed to NO2. The American journal of pathology 1986; 123: 126-133.
23. Teixeira V H, Nadarajan P, Graham T A, Pipinikas C P, Brown J M, Falzon M, Nye E, Poulsom R, Lawrence D, Wright N A, McDonald S, Giangreco A, Simons B D, Janes S M. Stochastic homeostasis in human airway epithelium is achieved by neutral competition of basal cell progenitors. eLife 2013; 2: e00966.
24. Wansleeben C, Barkauskas C E, Rock J R, Hogan B L. Stem cells of the adult lung: their development and role in homeostasis, regeneration, and disease. Wiley interdisciplinary reviews Developmental biology 2013; 2: 131-148.
25. O'Koren E G, Hogan B L, Gunn M D. Loss of basal cells precedes bronchiolitis obliterans-like pathological changes in a murine model of chlorine gas inhalation. American journal of respiratory cell and molecular biology 2013; 49: 788-797.
26. Staudt M R, Buro-Auriemma L J, Walters M S, Salit J, Vincent T, Shaykhiev R, Mezey J G, Tilley A E, Kaner R J, Ho M W, Crystal R G. Airway Basal stem/progenitor cells have diminished capacity to regenerate airway epithelium in chronic obstructive pulmonary disease. American journal of respiratory and critical care medicine 2014; 190: 955-958.
27. Vaughan A E, Brumwell A N, Xi Y, Gotts J E, Brownfield D G, Treutlein B, Tan K, Tan V, Liu F C, Looney M R, Matthay M A, Rock J R, Chapman H A. Lineage-negative progenitors mobilize to regenerate lung epithelium after major injury. Nature 2015; 517: 621-625.
28. Watson J K, Rulands S, Wilkinson A C, Wuidart A, Ousset M, Van Keymeulen A, Gottgens B, Blanpain C, Simons B D, Rawlins E L. Clonal Dynamics Reveal Two Distinct Populations of Basal Cells in Slow-Turnover Airway Epithelium. Cell reports 2015; 12: 90-101.
29. Rosen C, Shezen E, Aronovich A, Klionsky Y Z, Yaakov Y, Assayag M, Biton I E, Tal O, Shakhar G, Ben-Hur H, Shneider D, Vaknin Z, Sadan O, Evron S, Freud E, Shoseyov D, Wilschanski M, Berkman N, Fibbe W E, Hagin D, Hillel-Karniel C, Krentsis I M, Bachar-Lustig E, Reisner Y. Preconditioning allows engraftment of mouse and human embryonic lung cells, enabling lung repair in mice. Nature medicine 2015; 21: 869-879.

30. Stripp B R, Reynolds S D. Maintenance and repair of the bronchiolar epithelium. Proceedings of the American Thoracic Society 2008; 5: 328-333.
31. Zahm J M, Kaplan H, Herard A L, Doriot F, Pierrot D, Somelette P, Puchelle E. Cell migration and proliferation during the in vitro wound repair of the respiratory epithelium. Cell motility and the cytoskeleton 1997; 37: 33-43.
32. Evans M J, Van Winkle L S, Fanucchi M V, Plopper C G. Cellular and molecular characteristics of basal cells in airway epithelium. Experimental lung research 2001; 27: 401-415.
33. Crosby L M, Waters C M. Epithelial repair mechanisms in the lung. American journal of physiology Lung cellular and molecular physiology 2010; 298: L715-731.
34. Dupuit F, Gaillard D, Hinnrasky J, Mongodin E, de Bentzmann S, Copreni E, Puchelle E. Differentiated and functional human airway epithelium regeneration in tracheal xenografts. American journal of physiology Lung cellular and molecular physiology 2000; 278: L165-176.
35. Pezzulo A A, Starner T D, Scheetz T E, Traver G L, Tilley A E, Harvey B G, Crystal R G, McCray P B, Jr., Zabner J. The air-liquid interface and use of primary cell cultures are important to recapitulate the transcriptional profile of in vivo airway epithelia. American journal of physiology Lung cellular and molecular physiology 2011; 300: L25-31.
36. Zuo W, Zhang T, Wu D Z, Guan S P, Liew A A, Yamamoto Y, Wang X, Lim S J, Vincent M, Lessard M, Crum C P, Xian W, McKeon F. p63(+)Krt5(+) distal airway stem cells are essential for lung regeneration. Nature 2015; 517: 616-620.
37. Xu K, Moghal N, Egan S E. Notch signaling in lung development and disease. Advances in experimental medicine and biology 2012; 727: 89-98.
38. Guseh J S, Bores S A, Stanger B Z, Zhou Q, Anderson W J, Melton D A, Rajagopal J. Notch signaling promotes airway mucous metaplasia and inhibits alveolar development. Development 2009; 136: 1751-1759.
39. Rock J R, Gao X, Xue Y, Randell S H, Kong Y Y, Hogan B L. Notch-dependent differentiation of adult airway basal stem cells. Cell stem cell 2011; 8: 639-648.
40. Gomi K, Arbelaez V, Crystal R G, Walters Miss. Activation of NOTCH1 or NOTCH3 signaling skews human airway basal cell differentiation toward a secretory pathway. PloS one 2015; 10: e0116507.
41. Gordon W R, Zimmerman B, He L, Miles L J, Huang J, Tiyanont K, McArthur D G, Aster J C, Perrimon N, Loparo J J, Blacklow S C. Mechanical Allostery: Evidence for a Force Requirement in the Proteolytic Activation of Notch. Developmental cell 2015; 33: 729-736.
42. Polacheck W J, Charest J L, Kamm R D. Interstitial flow influences direction of tumor cell migration through competing mechanisms. Proceedings of the National Academy of Sciences of the United States of America 2011; 108: 11115-11120.
43. Musah S, Chen J, Hoyle G W. Repair of tracheal epithelium by basal cells after chlorine-induced injury. Respiratory research 2012; 13: 107.
44. Hong K U, Reynolds S D, Watkins S, Fuchs E, Stripp B R. Basal cells are a multipotent progenitor capable of renewing the bronchial epithelium. The American journal of pathology 2004; 164: 577-588.
45. Evans M J, Cabral L J, Stephens R J, Freeman G. Renewal of alveolar epithelium in the rat following exposure to NO2. The American journal of pathology 1973; 70: 175-198.
46. Barkauskas C E, Cronce M J, Rackley C R, Bowie E J, Keene D R, Stripp B R, Randell S H, Noble P W, Hogan B L. Type 2 alveolar cells are stem cells in adult lung. The Journal of clinical investigation 2013; 123: 3025-3036.
47. Kim C F, Jackson E L, Woolfenden A E, Lawrence S, Babar I, Vogel S, Crowley D, Bronson R T, Jacks T. Identification of bronchioalveolar stem cells in normal lung and lung cancer. Cell 2005; 121: 823-835.
48. Desai T J, Brownfield D G, Krasnow M A. Alveolar progenitor and stem cells in lung development, renewal and cancer. Nature 2014; 507: 190-194.
49. Jain R, Barkauskas C E, Takeda N, Bowie E J, Aghajanian H, Wang Q, Padmanabhan A, Manderfield L J, Gupta M, Li D, Li L, Trivedi C M, Hogan B L, Epstein J A. Plasticity of Hopx(+) type I alveolar cells to regenerate type II cells in the lung. Nature communications 2015; 6: 6727.
50. Balestrini J L, Niklason L E. Extracellular matrix as a driver for lung regeneration. Annals of biomedical engineering 2015; 43: 568-576.
51. Daley W P, Peters S B, Larsen M. Extracellular matrix dynamics in development and regenerative medicine. Journal of cell science 2008; 121: 255-264.
52. Karp P H, Moninger T O, Weber S P, Nesselhauf T S, Launspach J L, Zabner J, Welsh M J. An in vitro model of differentiated human airway epithelia. Methods for establishing primary cultures. Methods in molecular biology 2002; 188: 115-137.
53. Liu X, Ory V, Chapman S, Yuan H, Albanese C, Kallakury B, Timofeeva O A, Nealon C, Dakic A, Simic V, Haddad B R, Rhim J S, Dritschilo A, Riegel A, McBride A, Schlegel R. ROCK inhibitor and feeder cells induce the conditional reprogramming of epithelial cells. The American journal of pathology 2012; 180: 599-607.
54. Sharpless N E, Sherr C J. Forging a signature of in vivo senescence. Nature reviews Cancer 2015; 15: 397-408.
55. Charest J M, Okamoto T, Kitano K, Yasuda A, Gilpin S E, Mathisen D J, Ott H C. Design and validation of a clinical-scale bioreactor for long-term isolated lung culture. Biomaterials 2015; 52: 79-87.
56. Gilpin S E, Guyette J P, Gonzalez G, et al. Perfusion decellularization of human and porcine lungs: bringing the matrix to clinical scale. The Journal of heart and lung transplantation: the official publication of the International Society for Heart Transplantation 2014; 33:298-308.
57. Midwood K S, Orend G. The role of tenascin-C in tissue injury and tumorigenesis. Journal of cell communication and signaling 2009; 3:287-310.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of providing a bioartificial lung organ, the method comprising:

providing a population of proliferative basal stem cells from a human donor wherein the cells are Krt5$^+$p63$^+$ cells;

maintaining and expanding the cells in culture for up to five passages, and wherein the cells are passaged at 60-100%, confluency;

providing a cell-free lung tissue matrix including an airway and vasculature, wherein the lung tissue matrix comprises one or both of exogenously added tenascin-c or exogenously added fibrillin-2;

seeding the lung tissue matrix with the stem cells through the airway, and with endothelial cells through the vasculature; and maintaining the matrix in an organ chamber under conditions comprising providing the lung tissue matrix with wet ventilation using a liquid media comprising a notch inhibitor, for a time sufficient for a pre-selected degree of organ maturation to occur.

2. The method of claim 1, in which the organ chamber comprises a chamber pressure sensor and a bi-directional drainage chamber pump each controlled by a control module that controls the bi-directional drainage pump in response to data transmitted by the chamber pressure sensor.

3. The method of claim 1, further comprising preventing a transpulmonary pressure gradient by equilibrating a pressure level in a venous line that is connected to a pulmonary vein of the lung tissue matrix with a pressure level in a media reservoir.

4. The method of claim 1, in which the organ chamber further comprises a pneumatic pressure control module connected to the organ chamber, wherein the pneumatic pressure control module:

generates negative pressure in the organ chamber during an inspiration phase;

maintains the organ chamber pressure for a plateau phase; and generates positive pressure in the organ chamber during an expiration phase.

5. The method of claim 1, in which wet ventilation comprises:

connecting a tracheal line that is also connected to the airway of the lung tissue matrix to a media reservoir, in which the tracheal line includes a bi-directional tracheal pump connected to the controller;

inflating the lung tissue matrix with media using the bi-directional tracheal pump; and deflating the lung tissue matrix using the bi-directional tracheal pump to withdraw media from the lung tissue matrix, wherein the media is continuously refreshed during wet ventilation.

6. The method of claim 1, in which the wet ventilation comprises:

connecting a tracheal line that is also connected to the airway of the lung tissue matrix to a media reservoir, in which the tracheal line includes a first pump and a second pump each connected to the controller;

inflating the lung tissue matrix with media using the first pump; and deflating the lung tissue matrix using the second pump to withdraw media from the lung tissue matrix, wherein the media is continuously refreshed during wet ventilation.

7. The method of claim 6, in which the controller controls the bi-directional tracheal pump in response to data transmitted by a tracheal pressure sensor connected to the tracheal line.

8. The method of claim 1, comprising providing wet ventilation using a liquid media comprising a notch inhibitor for at least 2, 5, 7, or 10 days, optionally followed by additional wet ventilation using a liquid media not comprising a notch inhibitor.

9. The method of claim 1, comprising contacting the lung tissue matrix with one or both of tenascin-c or fibrillin-2 prior to seeding.

10. A functional lung produced by the method of claim 1.

11. The functional lung of claim 10, wherein the organ is a full lung or a vascularized portion thereof.

12. A method of treating a subject having impaired or reduced lung capacity, the method comprising transplanting the lung of claim 10 into the subject.

13. The method of claim 1, wherein the Krt5+p63+ cells are obtained from the airway of the donor.

14. The method of claim 1, wherein the cells are passaged at 80% confluency.

15. The method of claim 1, wherein the Notch inhibitor is a gamma secretase inhibitor.

16. The method of claim 1, wherein the cells are passaged in culture in the absence of a ROCK inhibitor prior to seeding the lung tissue matrix.

* * * * *

UNITED STATES PATENT AND TRADEMARK OFFICE
CERTIFICATE OF CORRECTION

PATENT NO. : 10,624,992 B2
APPLICATION NO. : 15/595464
DATED : April 21, 2020
INVENTOR(S) : Harald C. Ott and Sarah E. Gilpin Page 1 of 1

It is certified that error appears in the above-identified patent and that said Letters Patent is hereby corrected as shown below:

In the Claims

In Column 73, Line 9, Claim 1, delete "60-100%, confluency" and insert -- 60-100% confluency --

Signed and Sealed this
Thirteenth Day of October, 2020

Andrei Iancu
*Director of the United States Patent and Trademark Office*

SEQUENCE LISTING

<160> NUMBER OF SEQ ID NOS: 2

<210> SEQ ID NO 1
<211> LENGTH: 2201
<212> TYPE: PRT
<213> ORGANISM: Homo sapiens

<400> SEQUENCE: 1

| | | | | | | | | | | | | | | |
|---|---|---|---|---|---|---|---|---|---|---|---|---|---|---|
| Met | Gly | Ala | Met | Thr | Gln | Leu | Leu | Ala | Gly | Val | Phe | Leu | Ala | Phe | Leu |
| 1 | | | | 5 | | | | | 10 | | | | | 15 | |
| Ala | Leu | Ala | Thr | Glu | Gly | Gly | Val | Leu | Lys | Lys | Val | Ile | Arg | His | Lys |
| | | | 20 | | | | | 25 | | | | | 30 | | |
| Arg | Gln | Ser | Gly | Val | Asn | Ala | Thr | Leu | Pro | Glu | Glu | Asn | Gln | Pro | Val |
| | | | 35 | | | | 40 | | | | | 45 | | | |
| Val | Phe | Asn | His | Val | Tyr | Asn | Ile | Lys | Leu | Pro | Val | Gly | Ser | Gln | Cys |
| | 50 | | | | | 55 | | | | | 60 | | | | |
| Ser | Val | Asp | Leu | Glu | Ser | Ala | Ser | Gly | Glu | Lys | Asp | Leu | Ala | Pro | Pro |
| 65 | | | | | 70 | | | | | 75 | | | | | 80 |
| Ser | Glu | Pro | Ser | Glu | Ser | Phe | Gln | Glu | His | Thr | Val | Asp | Gly | Glu | Asn |
| | | | | 85 | | | | | 90 | | | | | 95 | |
| Gln | Ile | Val | Phe | Thr | His | Arg | Ile | Asn | Ile | Pro | Arg | Arg | Ala | Cys | Gly |
| | | | | 100 | | | | | 105 | | | | | 110 | |
| Cys | Ala | Ala | Ala | Pro | Asp | Val | Lys | Glu | Leu | Leu | Ser | Arg | Leu | Glu | Glu |
| | | | 115 | | | | | 120 | | | | | 125 | | |
| Leu | Glu | Asn | Leu | Val | Ser | Ser | Leu | Arg | Glu | Gln | Cys | Thr | Ala | Gly | Ala |
| | 130 | | | | | 135 | | | | | 140 | | | | |
| Gly | Cys | Cys | Leu | Gln | Pro | Ala | Thr | Gly | Arg | Leu | Asp | Thr | Arg | Pro | Phe |
| 145 | | | | | 150 | | | | | 155 | | | | | 160 |
| Cys | Ser | Gly | Arg | Gly | Asn | Phe | Ser | Thr | Glu | Gly | Cys | Gly | Cys | Val | Cys |
| | | | | 165 | | | | | 170 | | | | | 175 | |
| Glu | Pro | Gly | Trp | Lys | Gly | Pro | Asn | Cys | Ser | Glu | Pro | Gly | Cys | Pro | Gly |
| | | | 180 | | | | | 185 | | | | | 190 | | |
| Asn | Cys | His | Leu | Arg | Gly | Arg | Cys | Ile | Asp | Gly | Gln | Cys | Ile | Cys | Asp |
| | | | | 195 | | | | | 200 | | | | | 205 | |
| Asp | Gly | Phe | Thr | Gly | Glu | Asp | Cys | Ser | Gln | Leu | Ala | Cys | Pro | Ser | Asp |
| | 210 | | | | | 215 | | | | | 220 | | | | |
| Cys | Asn | Asp | Gln | Gly | Lys | Cys | Val | Asn | Gly | Val | Cys | Ile | Cys | Phe | Glu |
| 225 | | | | | 230 | | | | | 235 | | | | | 240 |
| Gly | Tyr | Ala | Gly | Ala | Asp | Cys | Ser | Arg | Glu | Ile | Cys | Pro | Val | Pro | Cys |
| | | | | 245 | | | | | 250 | | | | | 255 | |
| Ser | Glu | Glu | His | Gly | Thr | Cys | Val | Asp | Gly | Leu | Cys | Val | Cys | His | Asp |
| | | | 260 | | | | | 265 | | | | | 270 | | |
| Gly | Phe | Ala | Gly | Asp | Asp | Cys | Asn | Lys | Pro | Leu | Cys | Leu | Asn | Asn | Cys |
| | | | | 275 | | | | | 280 | | | | | 285 | |
| Tyr | Asn | Arg | Gly | Arg | Cys | Val | Glu | Asn | Glu | Cys | Val | Cys | Asp | Glu | Gly |
| | 290 | | | | | 295 | | | | | 300 | | | | |
| Phe | Thr | Gly | Glu | Asp | Cys | Ser | Glu | Leu | Ile | Cys | Pro | Asn | Asp | Cys | Phe |
| 305 | | | | | 310 | | | | | 315 | | | | | 320 |
| Asp | Arg | Gly | Arg | Cys | Ile | Asn | Gly | Thr | Cys | Tyr | Cys | Glu | Glu | Gly | Phe |
| | | | | 325 | | | | | 330 | | | | | 335 | |
| Thr | Gly | Glu | Asp | Cys | Gly | Lys | Pro | Thr | Cys | Pro | His | Ala | Cys | His | Thr |
| | | | 340 | | | | | 345 | | | | | 350 | | |
| Gln | Gly | Arg | Cys | Glu | Glu | Gly | Gln | Cys | Val | Cys | Asp | Glu | Gly | Phe | Ala |
| | | | | 355 | | | | | 360 | | | | | 365 | |

-continued

Gly Val Asp Cys Ser Glu Lys Arg Cys Pro Ala Asp Cys His Asn Arg
370                 375                 380

Gly Arg Cys Val Asp Gly Arg Cys Glu Cys Asp Asp Gly Phe Thr Gly
385                 390                 395                 400

Ala Asp Cys Gly Glu Leu Lys Cys Pro Asn Gly Cys Ser Gly His Gly
                405                 410                 415

Arg Cys Val Asn Gly Gln Cys Val Cys Asp Glu Gly Tyr Thr Gly Glu
            420                 425                 430

Asp Cys Ser Gln Leu Arg Cys Pro Asn Asp Cys His Ser Arg Gly Arg
        435                 440                 445

Cys Val Glu Gly Lys Cys Val Cys Glu Gln Gly Phe Lys Gly Tyr Asp
    450                 455                 460

Cys Ser Asp Met Ser Cys Pro Asn Asp Cys His Gln His Gly Arg Cys
465                 470                 475                 480

Val Asn Gly Met Cys Val Cys Asp Asp Gly Tyr Thr Gly Glu Asp Cys
                485                 490                 495

Arg Asp Arg Gln Cys Pro Arg Asp Cys Ser Asn Arg Gly Leu Cys Val
                500                 505                 510

Asp Gly Gln Cys Val Cys Glu Asp Gly Phe Thr Gly Pro Asp Cys Ala
            515                 520                 525

Glu Leu Ser Cys Pro Asn Asp Cys His Gly Gln Gly Arg Cys Val Asn
        530                 535                 540

Gly Gln Cys Val Cys His Glu Gly Phe Met Gly Lys Asp Cys Lys Glu
545                 550                 555                 560

Gln Arg Cys Pro Ser Asp Cys His Gly Gln Gly Arg Cys Val Asp Gly
                565                 570                 575

Gln Cys Ile Cys His Glu Gly Phe Thr Gly Leu Asp Cys Gly Gln His
            580                 585                 590

Ser Cys Pro Ser Asp Cys Asn Asn Leu Gly Gln Cys Val Ser Gly Arg
        595                 600                 605

Cys Ile Cys Asn Glu Gly Tyr Ser Gly Glu Asp Cys Ser Glu Val Ser
    610                 615                 620

Pro Pro Lys Asp Leu Val Val Thr Glu Val Thr Glu Thr Val Asn
625                 630                 635                 640

Leu Ala Trp Asp Asn Glu Met Arg Val Thr Glu Tyr Leu Val Val Tyr
                645                 650                 655

Thr Pro Thr His Glu Gly Gly Leu Glu Met Gln Phe Arg Val Pro Gly
            660                 665                 670

Asp Gln Thr Ser Thr Ile Ile Gln Glu Leu Glu Pro Gly Val Glu Tyr
        675                 680                 685

Phe Ile Arg Val Phe Ala Ile Leu Glu Asn Lys Lys Ser Ile Pro Val
    690                 695                 700

Ser Ala Arg Val Ala Thr Tyr Leu Pro Ala Pro Glu Gly Leu Lys Phe
705                 710                 715                 720

Lys Ser Ile Lys Glu Thr Ser Val Glu Val Glu Trp Asp Pro Leu Asp
                725                 730                 735

Ile Ala Phe Glu Thr Trp Glu Ile Ile Phe Arg Asn Met Asn Lys Glu
            740                 745                 750

Asp Glu Gly Glu Ile Thr Lys Ser Leu Arg Arg Pro Glu Thr Ser Tyr
        755                 760                 765

Arg Gln Thr Gly Leu Ala Pro Gly Gln Glu Tyr Glu Ile Ser Leu His
    770                 775                 780

Ile Val Lys Asn Asn Thr Arg Gly Pro Gly Leu Lys Arg Val Thr Thr

```
            785                 790                 795                 800
        Thr Arg Leu Asp Ala Pro Ser Gln Ile Glu Val Lys Asp Val Thr Asp
                        805                 810                 815

Thr Thr Ala Leu Ile Thr Trp Phe Lys Pro Leu Ala Glu Ile Asp Gly
                        820                 825                 830

Ile Glu Leu Thr Tyr Gly Ile Lys Asp Val Pro Gly Asp Arg Thr Thr
                        835                 840                 845

Ile Asp Leu Thr Glu Asp Glu Asn Gln Tyr Ser Ile Gly Asn Leu Lys
                        850                 855                 860

Pro Asp Thr Glu Tyr Glu Val Ser Leu Ile Ser Arg Arg Gly Asp Met
        865                 870                 875                 880

Ser Ser Asn Pro Ala Lys Glu Thr Phe Thr Thr Gly Leu Asp Ala Pro
                        885                 890                 895

Arg Asn Leu Arg Arg Val Ser Gln Thr Asp Asn Ser Ile Thr Leu Glu
                        900                 905                 910

Trp Arg Asn Gly Lys Ala Ala Ile Asp Ser Tyr Arg Ile Lys Tyr Ala
                        915                 920                 925

Pro Ile Ser Gly Gly Asp His Ala Glu Val Asp Val Pro Lys Ser Gln
                        930                 935                 940

Gln Ala Thr Thr Lys Thr Thr Leu Thr Gly Leu Arg Pro Gly Thr Glu
        945                 950                 955                 960

Tyr Gly Ile Gly Val Ser Ala Val Lys Glu Asp Lys Glu Ser Asn Pro
                        965                 970                 975

Ala Thr Ile Asn Ala Ala Thr Glu Leu Asp Thr Pro Lys Asp Leu Gln
                        980                 985                 990

Val Ser Glu Thr Ala Glu Thr Ser Leu Thr Leu Leu Trp Lys Thr Pro
                        995                 1000                1005

Leu Ala Lys Phe Asp Arg Tyr Arg Leu Asn Tyr Ser Leu Pro Thr
                        1010                1015                1020

Gly Gln Trp Val Gly Val Gln Leu Pro Arg Asn Thr Thr Ser Tyr
                        1025                1030                1035

Val Leu Arg Gly Leu Glu Pro Gly Gln Glu Tyr Asn Val Leu Leu
                        1040                1045                1050

Thr Ala Glu Lys Gly Arg His Lys Ser Lys Pro Ala Arg Val Lys
                        1055                1060                1065

Ala Ser Thr Glu Gln Ala Pro Glu Leu Glu Asn Leu Thr Val Thr
                        1070                1075                1080

Glu Val Gly Trp Asp Gly Leu Arg Leu Asn Trp Thr Ala Ala Asp
                        1085                1090                1095

Gln Ala Tyr Glu His Phe Ile Ile Gln Val Gln Glu Ala Asn Lys
                        1100                1105                1110

Val Glu Ala Ala Arg Asn Leu Thr Val Pro Gly Ser Leu Arg Ala
                        1115                1120                1125

Val Asp Ile Pro Gly Leu Lys Ala Ala Thr Pro Tyr Thr Val Ser
                        1130                1135                1140

Ile Tyr Gly Val Ile Gln Gly Tyr Arg Thr Pro Val Leu Ser Ala
                        1145                1150                1155

Glu Ala Ser Thr Gly Glu Thr Pro Asn Leu Gly Glu Val Val Val
                        1160                1165                1170

Ala Glu Val Gly Trp Asp Ala Leu Lys Leu Asn Trp Thr Ala Pro
                        1175                1180                1185

Glu Gly Ala Tyr Glu Tyr Phe Phe Ile Gln Val Gln Glu Ala Asp
                        1190                1195                1200
```

```
Thr Val Glu Ala Ala Gln Asn Leu Thr Val Pro Gly Gly Leu Arg
1205                 1210                1215

Ser Thr Asp Leu Pro Gly Leu Lys Ala Ala Thr His Tyr Thr Ile
1220                 1225                1230

Thr Ile Arg Gly Val Thr Gln Asp Phe Ser Thr Thr Pro Leu Ser
1235                 1240                1245

Val Glu Val Leu Thr Glu Val Pro Asp Met Gly Asn Leu Thr
1250                 1255                1260

Val Thr Glu Val Ser Trp Asp Ala Leu Arg Leu Asn Trp Thr Thr
1265                 1270                1275

Pro Asp Gly Thr Tyr Asp Gln Phe Thr Ile Gln Val Gln Glu Ala
1280                 1285                1290

Asp Gln Val Glu Glu Ala His Asn Leu Thr Val Pro Gly Ser Leu
1295                 1300                1305

Arg Ser Met Glu Ile Pro Gly Leu Arg Ala Gly Thr Pro Tyr Thr
1310                 1315                1320

Val Thr Leu His Gly Glu Val Arg Gly His Ser Thr Arg Pro Leu
1325                 1330                1335

Ala Val Glu Val Val Thr Glu Asp Leu Pro Gln Leu Gly Asp Leu
1340                 1345                1350

Ala Val Ser Glu Val Gly Trp Asp Gly Leu Arg Leu Asn Trp Thr
1355                 1360                1365

Ala Ala Asp Asn Ala Tyr Glu His Phe Val Ile Gln Val Gln Glu
1370                 1375                1380

Val Asn Lys Val Glu Ala Ala Gln Asn Leu Thr Leu Pro Gly Ser
1385                 1390                1395

Leu Arg Ala Val Asp Ile Pro Gly Leu Glu Ala Ala Thr Pro Tyr
1400                 1405                1410

Arg Val Ser Ile Tyr Gly Val Ile Arg Gly Tyr Arg Thr Pro Val
1415                 1420                1425

Leu Ser Ala Glu Ala Ser Thr Ala Lys Glu Pro Glu Ile Gly Asn
1430                 1435                1440

Leu Asn Val Ser Asp Ile Thr Pro Glu Ser Phe Asn Leu Ser Trp
1445                 1450                1455

Met Ala Thr Asp Gly Ile Phe Glu Thr Phe Thr Ile Glu Ile Ile
1460                 1465                1470

Asp Ser Asn Arg Leu Leu Glu Thr Val Glu Tyr Asn Ile Ser Gly
1475                 1480                1485

Ala Glu Arg Thr Ala His Ile Ser Gly Leu Pro Pro Ser Thr Asp
1490                 1495                1500

Phe Ile Val Tyr Leu Ser Gly Leu Ala Pro Ser Ile Arg Thr Lys
1505                 1510                1515

Thr Ile Ser Ala Thr Ala Thr Thr Glu Ala Leu Pro Leu Leu Glu
1520                 1525                1530

Asn Leu Thr Ile Ser Asp Ile Asn Pro Tyr Gly Phe Thr Val Ser
1535                 1540                1545

Trp Met Ala Ser Glu Asn Ala Phe Asp Ser Phe Leu Val Thr Val
1550                 1555                1560

Val Asp Ser Gly Lys Leu Leu Asp Pro Gln Glu Phe Thr Leu Ser
1565                 1570                1575

Gly Thr Gln Arg Lys Leu Glu Leu Arg Gly Leu Ile Thr Gly Ile
1580                 1585                1590
```

```
Gly Tyr Glu Val Met Val Ser Gly Phe Thr Gln Gly His Gln Thr
    1595                1600                1605

Lys Pro Leu Arg Ala Glu Ile Val Thr Glu Ala Glu Pro Glu Val
    1610                1615                1620

Asp Asn Leu Leu Val Ser Asp Ala Thr Pro Asp Gly Phe Arg Leu
    1625                1630                1635

Ser Trp Thr Ala Asp Glu Gly Val Phe Asp Asn Phe Val Leu Lys
    1640                1645                1650

Ile Arg Asp Thr Lys Lys Gln Ser Glu Pro Leu Glu Ile Thr Leu
    1655                1660                1665

Leu Ala Pro Glu Arg Thr Arg Asp Ile Thr Gly Leu Arg Glu Ala
    1670                1675                1680

Thr Glu Tyr Glu Ile Glu Leu Tyr Gly Ile Ser Lys Gly Arg Arg
    1685                1690                1695

Ser Gln Thr Val Ser Ala Ile Ala Thr Thr Ala Met Gly Ser Pro
    1700                1705                1710

Lys Glu Val Ile Phe Ser Asp Ile Thr Glu Asn Ser Ala Thr Val
    1715                1720                1725

Ser Trp Arg Ala Pro Thr Ala Gln Val Glu Ser Phe Arg Ile Thr
    1730                1735                1740

Tyr Val Pro Ile Thr Gly Gly Thr Pro Ser Met Val Thr Val Asp
    1745                1750                1755

Gly Thr Lys Thr Gln Thr Arg Leu Val Lys Leu Ile Pro Gly Val
    1760                1765                1770

Glu Tyr Leu Val Ser Ile Ile Ala Met Lys Gly Phe Glu Glu Ser
    1775                1780                1785

Glu Pro Val Ser Gly Ser Phe Thr Thr Ala Leu Asp Gly Pro Ser
    1790                1795                1800

Gly Leu Val Thr Ala Asn Ile Thr Asp Ser Glu Ala Leu Ala Arg
    1805                1810                1815

Trp Gln Pro Ala Ile Ala Thr Val Asp Ser Tyr Val Ile Ser Tyr
    1820                1825                1830

Thr Gly Glu Lys Val Pro Glu Ile Thr Arg Thr Val Ser Gly Asn
    1835                1840                1845

Thr Val Glu Tyr Ala Leu Thr Asp Leu Glu Pro Ala Thr Glu Tyr
    1850                1855                1860

Thr Leu Arg Ile Phe Ala Glu Lys Gly Pro Gln Lys Ser Ser Thr
    1865                1870                1875

Ile Thr Ala Lys Phe Thr Thr Asp Leu Asp Ser Pro Arg Asp Leu
    1880                1885                1890

Thr Ala Thr Glu Val Gln Ser Glu Thr Ala Leu Leu Thr Trp Arg
    1895                1900                1905

Pro Pro Arg Ala Ser Val Thr Gly Tyr Leu Leu Val Tyr Glu Ser
    1910                1915                1920

Val Asp Gly Thr Val Lys Glu Val Ile Val Gly Pro Asp Thr Thr
    1925                1930                1935

Ser Tyr Ser Leu Ala Asp Leu Ser Pro Ser Thr His Tyr Thr Ala
    1940                1945                1950

Lys Ile Gln Ala Leu Asn Gly Pro Leu Arg Ser Asn Met Ile Gln
    1955                1960                1965

Thr Ile Phe Thr Thr Ile Gly Leu Leu Tyr Pro Phe Pro Lys Asp
    1970                1975                1980

Cys Ser Gln Ala Met Leu Asn Gly Asp Thr Thr Ser Gly Leu Tyr
```

```
            1985                1990                1995
Thr Ile Tyr Leu Asn Gly Asp Lys Ala Glu Ala Leu Glu Val Phe
            2000                2005                2010

Cys Asp Met Thr Ser Asp Gly Gly Gly Trp Ile Val Phe Leu Arg
            2015                2020                2025

Arg Lys Asn Gly Arg Glu Asn Phe Tyr Gln Asn Trp Lys Ala Tyr
            2030                2035                2040

Ala Ala Gly Phe Gly Asp Arg Arg Glu Glu Phe Trp Leu Gly Leu
            2045                2050                2055

Asp Asn Leu Asn Lys Ile Thr Ala Gln Gly Gln Tyr Glu Leu Arg
            2060                2065                2070

Val Asp Leu Arg Asp His Gly Glu Thr Ala Phe Ala Val Tyr Asp
            2075                2080                2085

Lys Phe Ser Val Gly Asp Ala Lys Thr Arg Tyr Lys Leu Lys Val
            2090                2095                2100

Glu Gly Tyr Ser Gly Thr Ala Gly Asp Ser Met Ala Tyr His Asn
            2105                2110                2115

Gly Arg Ser Phe Ser Thr Phe Asp Lys Asp Thr Asp Ser Ala Ile
            2120                2125                2130

Thr Asn Cys Ala Leu Ser Tyr Lys Gly Ala Phe Trp Tyr Arg Asn
            2135                2140                2145

Cys His Arg Val Asn Leu Met Gly Arg Tyr Gly Asp Asn Asn His
            2150                2155                2160

Ser Gln Gly Val Asn Trp Phe His Trp Lys Gly His Glu His Ser
            2165                2170                2175

Ile Gln Phe Ala Glu Met Lys Leu Arg Pro Ser Asn Phe Arg Asn
            2180                2185                2190

Leu Glu Gly Arg Arg Lys Arg Ala
            2195                2200

<210> SEQ ID NO 2
<211> LENGTH: 2912
<212> TYPE: PRT
<213> ORGANISM: Homo sapiens

<400> SEQUENCE: 2

Met Gly Arg Arg Arg Arg Leu Cys Leu Gln Leu Tyr Phe Leu Trp Leu
1               5                   10                  15

Gly Cys Val Val Leu Trp Ala Gln Gly Thr Ala Gly Gln Pro Gln Pro
                20                  25                  30

Pro Pro Pro Lys Pro Pro Arg Pro Gln Pro Pro Gln Gln Val Arg
            35                  40                  45

Ser Ala Thr Ala Gly Ser Glu Gly Gly Phe Leu Ala Pro Glu Tyr Arg
50                  55                  60

Glu Glu Gly Ala Ala Val Ala Ser Arg Val Arg Arg Gly Gln Gln
65                  70                  75                  80

Asp Val Leu Arg Gly Pro Asn Val Cys Gly Ser Arg Phe His Ser Tyr
                85                  90                  95

Cys Cys Pro Gly Trp Lys Thr Leu Pro Gly Gly Asn Gln Cys Ile Val
            100                 105                 110

Pro Ile Cys Arg Asn Ser Cys Gly Asp Gly Phe Cys Ser Arg Pro Asn
        115                 120                 125

Met Cys Thr Cys Ser Ser Gly Gln Ile Ser Ser Thr Cys Gly Ser Lys
    130                 135                 140
```

```
Ser Ile Gln Gln Cys Ser Val Arg Cys Met Asn Gly Gly Thr Cys Ala
145                 150                 155                 160

Asp Asp His Cys Gln Cys Gln Lys Gly Tyr Ile Gly Thr Tyr Cys Gly
            165                 170                 175

Gln Pro Val Cys Glu Asn Gly Cys Gln Asn Gly Gly Arg Cys Ile Gly
            180                 185                 190

Pro Asn Arg Cys Ala Cys Val Tyr Gly Phe Thr Gly Pro Gln Cys Glu
            195                 200                 205

Arg Asp Tyr Arg Thr Gly Pro Cys Phe Thr Gln Val Asn Asn Gln Met
210                 215                 220

Cys Gln Gly Gln Leu Thr Gly Ile Val Cys Thr Lys Thr Leu Cys Cys
225                 230                 235                 240

Ala Thr Ile Gly Arg Ala Trp Gly His Pro Cys Glu Met Cys Pro Ala
            245                 250                 255

Gln Pro Gln Pro Cys Arg Arg Gly Phe Ile Pro Asn Ile Arg Thr Gly
            260                 265                 270

Ala Cys Gln Asp Val Asp Glu Cys Gln Ala Ile Pro Gly Ile Cys Gln
            275                 280                 285

Gly Gly Asn Cys Ile Asn Thr Val Gly Ser Phe Glu Cys Arg Cys Pro
290                 295                 300

Ala Gly His Lys Gln Ser Glu Thr Thr Gln Lys Cys Glu Asp Ile Asp
305                 310                 315                 320

Glu Cys Ser Ile Ile Pro Gly Ile Cys Glu Thr Gly Glu Cys Ser Asn
            325                 330                 335

Thr Val Gly Ser Tyr Phe Cys Val Cys Pro Arg Gly Tyr Val Thr Ser
            340                 345                 350

Thr Asp Gly Ser Arg Cys Ile Asp Gln Arg Thr Gly Met Cys Phe Ser
            355                 360                 365

Gly Leu Val Asn Gly Arg Cys Ala Gln Glu Leu Pro Gly Arg Met Thr
            370                 375                 380

Lys Met Gln Cys Cys Glu Pro Gly Arg Cys Trp Gly Ile Gly Thr
385                 390                 395                 400

Ile Pro Glu Ala Cys Pro Val Arg Gly Ser Glu Glu Tyr Arg Arg Leu
            405                 410                 415

Cys Met Asp Gly Leu Pro Met Gly Ile Pro Gly Ser Ala Gly Ser
            420                 425                 430

Arg Pro Gly Gly Thr Gly Asn Gly Phe Ala Pro Ser Gly Asn Gly
            435                 440                 445

Asn Gly Tyr Gly Pro Gly Gly Thr Gly Phe Ile Pro Ile Pro Gly Gly
            450                 455                 460

Asn Gly Phe Ser Pro Gly Val Gly Gly Ala Gly Val Gly Ala Gly Gly
465                 470                 475                 480

Gln Gly Pro Ile Ile Thr Gly Leu Thr Ile Leu Asn Gln Thr Ile Asp
            485                 490                 495

Ile Cys Lys His His Ala Asn Leu Cys Leu Asn Gly Arg Cys Ile Pro
            500                 505                 510

Thr Val Ser Ser Tyr Arg Cys Glu Cys Asn Met Gly Tyr Lys Gln Asp
            515                 520                 525

Ala Asn Gly Asp Cys Ile Asp Val Asp Glu Cys Thr Ser Asn Pro Cys
            530                 535                 540

Thr Asn Gly Asp Cys Val Asn Thr Pro Gly Ser Tyr Tyr Cys Lys Cys
545                 550                 555                 560

His Ala Gly Phe Gln Arg Thr Pro Thr Lys Gln Ala Cys Ile Asp Ile
```

```
                         565                 570                 575
Asp Glu Cys Ile Gln Asn Gly Val Leu Cys Lys Asn Gly Arg Cys Val
                580                 585                 590
Asn Thr Asp Gly Ser Phe Gln Cys Ile Cys Asn Ala Gly Phe Glu Leu
                595                 600                 605
Thr Thr Asp Gly Lys Asn Cys Val Asp His Asp Glu Cys Thr Thr Thr
            610                 615                 620
Asn Met Cys Leu Asn Gly Met Cys Ile Asn Glu Asp Gly Ser Phe Lys
625                 630                 635                 640
Cys Ile Cys Lys Pro Gly Phe Val Leu Ala Pro Asn Gly Arg Tyr Cys
                645                 650                 655
Thr Asp Val Asp Glu Cys Gln Thr Pro Gly Ile Cys Met Asn Gly His
            660                 665                 670
Cys Ile Asn Ser Glu Gly Ser Phe Arg Cys Asp Cys Pro Pro Gly Leu
            675                 680                 685
Ala Val Gly Met Asp Gly Arg Val Cys Val Asp Thr His Met Arg Ser
            690                 695                 700
Thr Cys Tyr Gly Gly Ile Lys Lys Gly Val Cys Val Arg Pro Phe Pro
705                 710                 715                 720
Gly Ala Val Thr Lys Ser Glu Cys Cys Ala Asn Pro Asp Tyr Gly
                725                 730                 735
Phe Gly Glu Pro Cys Gln Pro Cys Pro Ala Lys Asn Ser Ala Glu Phe
                740                 745                 750
His Gly Leu Cys Ser Ser Gly Val Gly Ile Thr Val Asp Gly Arg Asp
            755                 760                 765
Ile Asn Glu Cys Ala Leu Asp Pro Asp Ile Cys Ala Asn Gly Ile Cys
            770                 775                 780
Glu Asn Leu Arg Gly Ser Tyr Arg Cys Asn Cys Asn Ser Gly Tyr Glu
785                 790                 795                 800
Pro Asp Ala Ser Gly Arg Asn Cys Ile Asp Ile Asp Glu Cys Leu Val
                805                 810                 815
Asn Arg Leu Leu Cys Asp Asn Gly Leu Cys Arg Asn Thr Pro Gly Ser
                820                 825                 830
Tyr Ser Cys Thr Cys Pro Pro Gly Tyr Val Phe Arg Thr Glu Thr Glu
            835                 840                 845
Thr Cys Glu Asp Ile Asn Glu Cys Glu Ser Asn Pro Cys Val Asn Gly
            850                 855                 860
Ala Cys Arg Asn Asn Leu Gly Ser Phe Asn Cys Glu Cys Ser Pro Gly
865                 870                 875                 880
Ser Lys Leu Ser Ser Thr Gly Leu Ile Cys Ile Asp Ser Leu Lys Gly
                885                 890                 895
Thr Cys Trp Leu Asn Ile Gln Asp Ser Arg Cys Glu Val Asn Ile Asn
                900                 905                 910
Gly Ala Thr Leu Lys Ser Glu Cys Cys Ala Thr Leu Gly Ala Ala Trp
            915                 920                 925
Gly Ser Pro Cys Glu Arg Cys Glu Leu Asp Thr Ala Cys Pro Arg Gly
            930                 935                 940
Leu Ala Arg Ile Lys Gly Val Thr Cys Glu Asp Val Asn Glu Cys Glu
945                 950                 955                 960
Val Phe Pro Gly Val Cys Pro Asn Gly Arg Cys Val Asn Ser Lys Gly
                965                 970                 975
Ser Phe His Cys Glu Cys Pro Glu Gly Leu Thr Leu Asp Gly Thr Gly
            980                 985                 990
```

```
Arg Val Cys Leu Asp Ile Arg Met Glu Gln Cys Tyr Leu Lys Trp Asp
        995                 1000                1005

Glu Asp Glu Cys Ile His Pro Val Pro Gly Lys Phe Arg Met Asp
    1010                1015                1020

Ala Cys Cys Cys Ala Val Gly Ala Ala Trp Gly Thr Glu Cys Glu
    1025                1030                1035

Glu Cys Pro Lys Pro Gly Thr Lys Glu Tyr Glu Thr Leu Cys Pro
    1040                1045                1050

Arg Gly Ala Gly Phe Ala Asn Arg Gly Asp Val Leu Thr Gly Arg
    1055                1060                1065

Pro Phe Tyr Lys Asp Ile Asn Glu Cys Lys Ala Phe Pro Gly Met
    1070                1075                1080

Cys Thr Tyr Gly Lys Cys Arg Asn Thr Ile Gly Ser Phe Lys Cys
    1085                1090                1095

Arg Cys Asn Ser Gly Phe Ala Leu Asp Met Glu Glu Arg Asn Cys
    1100                1105                1110

Thr Asp Ile Asp Glu Cys Arg Ile Ser Pro Asp Leu Cys Gly Ser
    1115                1120                1125

Gly Ile Cys Val Asn Thr Pro Gly Ser Phe Glu Cys Glu Cys Phe
    1130                1135                1140

Glu Gly Tyr Glu Ser Gly Phe Met Met Met Lys Asn Cys Met Asp
    1145                1150                1155

Ile Asp Glu Cys Glu Arg Asn Pro Leu Leu Cys Arg Gly Gly Thr
    1160                1165                1170

Cys Val Asn Thr Glu Gly Ser Phe Gln Cys Asp Cys Pro Leu Gly
    1175                1180                1185

His Glu Leu Ser Pro Ser Arg Glu Asp Cys Val Asp Ile Asn Glu
    1190                1195                1200

Cys Ser Leu Ser Asp Asn Leu Cys Arg Asn Gly Lys Cys Val Asn
    1205                1210                1215

Met Ile Gly Thr Tyr Gln Cys Ser Cys Asn Pro Gly Tyr Gln Ala
    1220                1225                1230

Thr Pro Asp Arg Gln Gly Cys Thr Asp Ile Asp Glu Cys Met Ile
    1235                1240                1245

Met Asn Gly Gly Cys Asp Thr Gln Cys Thr Asn Ser Glu Gly Ser
    1250                1255                1260

Tyr Glu Cys Ser Cys Ser Glu Gly Tyr Ala Leu Met Pro Asp Gly
    1265                1270                1275

Arg Ser Cys Ala Asp Ile Asp Glu Cys Glu Asn Asn Pro Asp Ile
    1280                1285                1290

Cys Asp Gly Gly Gln Cys Thr Asn Ile Pro Gly Glu Tyr Arg Cys
    1295                1300                1305

Leu Cys Tyr Asp Gly Phe Met Ala Ser Met Asp Met Lys Thr Cys
    1310                1315                1320

Ile Asp Val Asn Glu Cys Asp Leu Asn Ser Asn Ile Cys Met Phe
    1325                1330                1335

Gly Glu Cys Glu Asn Thr Lys Gly Ser Phe Ile Cys His Cys Gln
    1340                1345                1350

Leu Gly Tyr Ser Val Lys Lys Gly Thr Thr Gly Cys Thr Asp Val
    1355                1360                1365

Asp Glu Cys Glu Ile Gly Ala His Asn Cys Asp Met His Ala Ser
    1370                1375                1380
```

```
Cys Leu Asn Ile Pro Gly Ser Phe Lys Cys Ser Cys Arg Glu Gly
    1385                1390                1395

Trp Ile Gly Asn Gly Ile Lys Cys Ile Asp Leu Asp Glu Cys Ser
    1400                1405                1410

Asn Gly Thr His Gln Cys Ser Ile Asn Ala Gln Cys Val Asn Thr
    1415                1420                1425

Pro Gly Ser Tyr Arg Cys Ala Cys Ser Glu Gly Phe Thr Gly Asp
    1430                1435                1440

Gly Phe Thr Cys Ser Asp Val Asp Glu Cys Ala Glu Asn Ile Asn
    1445                1450                1455

Leu Cys Glu Asn Gly Gln Cys Leu Asn Val Pro Gly Ala Tyr Arg
    1460                1465                1470

Cys Glu Cys Glu Met Gly Phe Thr Pro Ala Ser Asp Ser Arg Ser
    1475                1480                1485

Cys Gln Asp Ile Asp Glu Cys Ser Phe Gln Asn Ile Cys Val Phe
    1490                1495                1500

Gly Thr Cys Asn Asn Leu Pro Gly Met Phe His Cys Ile Cys Asp
    1505                1510                1515

Asp Gly Tyr Glu Leu Asp Arg Thr Gly Gly Asn Cys Thr Asp Ile
    1520                1525                1530

Asp Glu Cys Ala Asp Pro Ile Asn Cys Val Asn Gly Leu Cys Val
    1535                1540                1545

Asn Thr Pro Gly Arg Tyr Glu Cys Asn Cys Pro Pro Asp Phe Gln
    1550                1555                1560

Leu Asn Pro Thr Gly Val Gly Cys Val Asp Asn Arg Val Gly Asn
    1565                1570                1575

Cys Tyr Leu Lys Phe Gly Pro Arg Gly Asp Gly Ser Leu Ser Cys
    1580                1585                1590

Asn Thr Glu Ile Gly Val Gly Val Ser Arg Ser Ser Cys Cys Cys
    1595                1600                1605

Ser Leu Gly Lys Ala Trp Gly Asn Pro Cys Glu Thr Cys Pro Pro
    1610                1615                1620

Val Asn Ser Thr Glu Tyr Tyr Thr Leu Cys Pro Gly Gly Glu Gly
    1625                1630                1635

Phe Arg Pro Asn Pro Ile Thr Ile Ile Leu Glu Asp Ile Asp Glu
    1640                1645                1650

Cys Gln Glu Leu Pro Gly Leu Cys Gln Gly Gly Asn Cys Ile Asn
    1655                1660                1665

Thr Phe Gly Ser Phe Gln Cys Glu Cys Pro Gln Gly Tyr Tyr Leu
    1670                1675                1680

Ser Glu Asp Thr Arg Ile Cys Glu Asp Ile Asp Glu Cys Phe Ala
    1685                1690                1695

His Pro Gly Val Cys Gly Pro Gly Thr Cys Tyr Asn Thr Leu Gly
    1700                1705                1710

Asn Tyr Thr Cys Ile Cys Pro Pro Glu Tyr Met Gln Val Asn Gly
    1715                1720                1725

Gly His Asn Cys Met Asp Met Arg Lys Ser Phe Cys Tyr Arg Ser
    1730                1735                1740

Tyr Asn Gly Thr Thr Cys Glu Asn Glu Leu Pro Phe Asn Val Thr
    1745                1750                1755

Lys Arg Met Cys Cys Cys Thr Tyr Asn Val Gly Lys Ala Trp Asn
    1760                1765                1770

Lys Pro Cys Glu Pro Cys Pro Thr Pro Gly Thr Ala Asp Phe Lys
```

```
                  1775                1780                1785
Thr Ile Cys Gly Asn Ile Pro Gly Phe Thr Phe Asp Ile His Thr
         1790                1795                1800
Gly Lys Ala Val Asp Ile Asp Glu Cys Lys Glu Ile Pro Gly Ile
         1805                1810                1815
Cys Ala Asn Gly Val Cys Ile Asn Gln Ile Gly Ser Phe Arg Cys
         1820                1825                1830
Glu Cys Pro Thr Gly Phe Ser Tyr Asn Asp Leu Leu Leu Val Cys
         1835                1840                1845
Glu Asp Ile Asp Glu Cys Ser Asn Gly Asp Asn Leu Cys Gln Arg
         1850                1855                1860
Asn Ala Asp Cys Ile Asn Ser Pro Gly Ser Tyr Arg Cys Glu Cys
         1865                1870                1875
Ala Ala Gly Phe Lys Leu Ser Pro Asn Gly Ala Cys Val Asp Arg
         1880                1885                1890
Asn Glu Cys Leu Glu Ile Pro Asn Val Cys Ser His Gly Leu Cys
         1895                1900                1905
Val Asp Leu Gln Gly Ser Tyr Gln Cys Ile Cys His Asn Gly Phe
         1910                1915                1920
Lys Ala Ser Gln Asp Gln Thr Met Cys Met Asp Val Asp Glu Cys
         1925                1930                1935
Glu Arg His Pro Cys Gly Asn Gly Thr Cys Lys Asn Thr Val Gly
         1940                1945                1950
Ser Tyr Asn Cys Leu Cys Tyr Pro Gly Phe Glu Leu Thr His Asn
         1955                1960                1965
Asn Asp Cys Leu Asp Ile Asp Glu Cys Ser Ser Phe Phe Gly Gln
         1970                1975                1980
Val Cys Arg Asn Gly Arg Cys Phe Asn Glu Ile Gly Ser Phe Lys
         1985                1990                1995
Cys Leu Cys Asn Glu Gly Tyr Glu Leu Thr Pro Asp Gly Lys Asn
         2000                2005                2010
Cys Ile Asp Thr Asn Glu Cys Val Ala Leu Pro Gly Ser Cys Ser
         2015                2020                2025
Pro Gly Thr Cys Gln Asn Leu Glu Gly Ser Phe Arg Cys Ile Cys
         2030                2035                2040
Pro Pro Gly Tyr Glu Val Lys Ser Glu Asn Cys Ile Asp Ile Asn
         2045                2050                2055
Glu Cys Asp Glu Asp Pro Asn Ile Cys Leu Phe Gly Ser Cys Thr
         2060                2065                2070
Asn Thr Pro Gly Gly Phe Gln Cys Leu Cys Pro Gly Phe Val
         2075                2080                2085
Leu Ser Asp Asn Gly Arg Arg Cys Phe Asp Thr Arg Gln Ser Phe
         2090                2095                2100
Cys Phe Thr Asn Phe Glu Asn Gly Lys Cys Ser Val Pro Lys Ala
         2105                2110                2115
Phe Asn Thr Thr Lys Ala Lys Cys Cys Cys Ser Lys Met Pro Gly
         2120                2125                2130
Glu Gly Trp Gly Asp Pro Cys Glu Leu Cys Pro Lys Asp Asp Glu
         2135                2140                2145
Val Ala Phe Gln Asp Leu Cys Pro Tyr Gly His Gly Thr Val Pro
         2150                2155                2160
Ser Leu His Asp Thr Arg Glu Asp Val Asn Glu Cys Leu Glu Ser
         2165                2170                2175
```

```
Pro Gly Ile Cys Ser Asn Gly Gln Cys Ile Asn Thr Asp Gly Ser
2180                2185                2190

Phe Arg Cys Glu Cys Pro Met Gly Tyr Asn Leu Asp Tyr Thr Gly
2195                2200                2205

Val Arg Cys Val Asp Thr Asp Glu Cys Ser Ile Gly Asn Pro Cys
2210                2215                2220

Gly Asn Gly Thr Cys Thr Asn Val Ile Gly Ser Phe Glu Cys Asn
2225                2230                2235

Cys Asn Glu Gly Phe Glu Pro Gly Pro Met Met Asn Cys Glu Asp
2240                2245                2250

Ile Asn Glu Cys Ala Gln Asn Pro Leu Leu Cys Ala Phe Arg Cys
2255                2260                2265

Met Asn Thr Phe Gly Ser Tyr Glu Cys Thr Cys Pro Ile Gly Tyr
2270                2275                2280

Ala Leu Arg Glu Asp Gln Lys Met Cys Lys Asp Leu Asp Glu Cys
2285                2290                2295

Ala Glu Gly Leu His Asp Cys Glu Ser Arg Gly Met Met Cys Lys
2300                2305                2310

Asn Leu Ile Gly Thr Phe Met Cys Ile Cys Pro Pro Gly Met Ala
2315                2320                2325

Arg Arg Pro Asp Gly Glu Gly Cys Val Asp Glu Asn Glu Cys Arg
2330                2335                2340

Thr Lys Pro Gly Ile Cys Glu Asn Gly Arg Cys Val Asn Ile Ile
2345                2350                2355

Gly Ser Tyr Arg Cys Glu Cys Asn Glu Gly Phe Gln Ser Ser Ser
2360                2365                2370

Ser Gly Thr Glu Cys Leu Asp Asn Arg Gln Gly Leu Cys Phe Ala
2375                2380                2385

Glu Val Leu Gln Thr Ile Cys Gln Met Ala Ser Ser Ser Arg Asn
2390                2395                2400

Leu Val Thr Lys Ser Glu Cys Cys Cys Asp Gly Gly Arg Gly Trp
2405                2410                2415

Gly His Gln Cys Glu Leu Cys Pro Leu Pro Gly Thr Ala Gln Tyr
2420                2425                2430

Lys Lys Ile Cys Pro His Gly Pro Gly Tyr Thr Thr Asp Gly Arg
2435                2440                2445

Asp Ile Asp Glu Cys Lys Val Met Pro Asn Leu Cys Thr Asn Gly
2450                2455                2460

Gln Cys Ile Asn Thr Met Gly Ser Phe Arg Cys Phe Cys Lys Val
2465                2470                2475

Gly Tyr Thr Thr Asp Ile Ser Gly Thr Ser Cys Ile Asp Leu Asp
2480                2485                2490

Glu Cys Ser Gln Ser Pro Lys Pro Cys Asn Tyr Ile Cys Lys Asn
2495                2500                2505

Thr Glu Gly Ser Tyr Gln Cys Ser Cys Pro Arg Gly Tyr Val Leu
2510                2515                2520

Gln Glu Asp Gly Lys Thr Cys Lys Asp Leu Asp Glu Cys Gln Thr
2525                2530                2535

Lys Gln His Asn Cys Gln Phe Leu Cys Val Asn Thr Leu Gly Gly
2540                2545                2550

Phe Thr Cys Lys Cys Pro Pro Gly Phe Thr Gln His His Thr Ala
2555                2560                2565
```

-continued

```
Cys Ile Asp Asn Asn Glu Cys Gly Ser Gln Pro Ser Leu Cys Gly
    2570                2575                2580

Ala Lys Gly Ile Cys Gln Asn Thr Pro Gly Ser Phe Ser Cys Glu
    2585                2590                2595

Cys Gln Arg Gly Phe Ser Leu Asp Ala Thr Gly Leu Asn Cys Glu
    2600                2605                2610

Asp Val Asp Glu Cys Asp Gly Asn His Arg Cys Gln His Gly Cys
    2615                2620                2625

Gln Asn Ile Leu Gly Gly Tyr Arg Cys Gly Cys Pro Gln Gly Tyr
    2630                2635                2640

Ile Gln His Tyr Gln Trp Asn Gln Cys Val Asp Glu Asn Glu Cys
    2645                2650                2655

Ser Asn Pro Asn Ala Cys Gly Ser Ala Ser Cys Tyr Asn Thr Leu
    2660                2665                2670

Gly Ser Tyr Lys Cys Ala Cys Pro Ser Gly Phe Ser Phe Asp Gln
    2675                2680                2685

Phe Ser Ser Ala Cys His Asp Val Asn Glu Cys Ser Ser Ser Lys
    2690                2695                2700

Asn Pro Cys Asn Tyr Gly Cys Ser Asn Thr Glu Gly Gly Tyr Leu
    2705                2710                2715

Cys Gly Cys Pro Pro Gly Tyr Tyr Arg Val Gly Gln Gly His Cys
    2720                2725                2730

Val Ser Gly Met Gly Phe Asn Lys Gly Gln Tyr Leu Ser Leu Asp
    2735                2740                2745

Thr Glu Val Asp Glu Glu Asn Ala Leu Ser Pro Glu Ala Cys Tyr
    2750                2755                2760

Glu Cys Lys Ile Asn Gly Tyr Ser Lys Lys Asp Ser Arg Gln Lys
    2765                2770                2775

Arg Ser Ile His Glu Pro Asp Pro Thr Ala Val Glu Gln Ile Ser
    2780                2785                2790

Leu Glu Ser Val Asp Met Asp Ser Pro Val Asn Met Lys Phe Asn
    2795                2800                2805

Leu Ser His Leu Gly Ser Lys Glu His Ile Leu Glu Leu Arg Pro
    2810                2815                2820

Ala Ile Gln Pro Leu Asn Asn His Ile Arg Tyr Val Ile Ser Gln
    2825                2830                2835

Gly Asn Asp Asp Ser Val Phe Arg Ile His Gln Arg Asn Gly Leu
    2840                2845                2850

Ser Tyr Leu His Thr Ala Lys Lys Lys Leu Met Pro Gly Thr Tyr
    2855                2860                2865

Thr Leu Glu Ile Thr Ser Ile Pro Leu Tyr Lys Lys Lys Glu Leu
    2870                2875                2880

Lys Lys Leu Glu Glu Ser Asn Glu Asp Asp Tyr Leu Leu Gly Glu
    2885                2890                2895

Leu Gly Glu Ala Leu Arg Met Arg Leu Gln Ile Gln Leu Tyr
    2900                2905                2910
```